US010619145B2

(12) United States Patent
Hoff et al.

(10) Patent No.: US 10,619,145 B2
(45) Date of Patent: Apr. 14, 2020

(54) POLYPEPTIDES HAVING SERINE PROTEASE ACTIVITY AND POLYNUCLEOTIDES ENCODING SAME AND THEIR APPLICATION IN ANIMAL FEED

(71) Applicant: Novozymes A/S, Bagsvaerd (DK)

(72) Inventors: Tine Hoff, Holte (DK); Peter Rahbek Oestergaard, Virum (DK); Katrine Fruergaard Pontoppidan, Lynge (DK)

(73) Assignee: Novozymes A/S, Bagsvaerd (DE)

( * ) Notice: Subject to any disclaimer, the term of this patent is extended or adjusted under 35 U.S.C. 154(b) by 0 days.

(21) Appl. No.: 15/517,236

(22) PCT Filed: Nov. 3, 2015

(86) PCT No.: PCT/EP2015/075512
§ 371 (c)(1),
(2) Date: Apr. 6, 2017

(87) PCT Pub. No.: WO2016/071302
PCT Pub. Date: May 12, 2016

(65) Prior Publication Data
US 2017/0306314 A1    Oct. 26, 2017

(30) Foreign Application Priority Data

Nov. 4, 2014    (EP) ..................................... 14191691

(51) Int. Cl.
| | |
|---|---|
| C12N 9/48 | (2006.01) |
| C12N 15/00 | (2006.01) |
| C12N 9/64 | (2006.01) |
| C12N 9/52 | (2006.01) |
| A23K 20/189 | (2016.01) |
| A23K 10/14 | (2016.01) |
| A23K 20/00 | (2016.01) |
| C12N 9/00 | (2006.01) |

(52) U.S. Cl.
CPC ............ *C12N 9/6424* (2013.01); *A23K 10/14* (2016.05); *A23K 20/189* (2016.05); *C12N 9/52* (2013.01); *A23K 20/00* (2016.05); *C12N 9/00* (2013.01)

(58) Field of Classification Search
None
See application file for complete search history.

(56) References Cited

U.S. PATENT DOCUMENTS

| | | | |
|---|---|---|---|
| 2011/0251116 A1 | 10/2011 | Aehle | |
| 2013/0330307 A1* | 12/2013 | Millan | A23K 1/009 424/93.41 |
| 2015/0026843 A1 | 1/2015 | Hoff | |

FOREIGN PATENT DOCUMENTS

| | | |
|---|---|---|
| EP | 1694847 B1 | 6/2012 |
| WO | 01/58275 A2 | 8/2001 |
| WO | 01/58276 A2 | 8/2001 |
| WO | 2004/034776 A2 | 4/2004 |
| WO | 2004/072221 A2 | 8/2004 |
| WO | 2004/072279 A2 | 8/2004 |
| WO | 2004/111220 A1 | 12/2004 |
| WO | 2004/111223 A1 | 12/2004 |
| WO | 2005/035747 A1 | 4/2005 |
| WO | 2005/123911 A2 | 12/2005 |
| WO | 2013/026796 A1 | 2/2013 |
| WO | 2013/041689 A1 | 3/2013 |
| WO | 2013/110766 A1 | 8/2013 |
| WO | 2013/189972 A2 | 12/2013 |
| WO | 2014/096259 A1 | 6/2014 |
| WO | 2014/122161 A2 | 8/2014 |

OTHER PUBLICATIONS

Studer Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Thrash. Genome sequence of the Marine Janibacter Sp. Strain HTCC2649. J. Bacteriol. 193:584-585(2011).*
Thrase. A3TJ83. UniProtKB Database. 2013.*
Sambrook et al. Molecular Cloning, 1989, Cold Spring Harbor Laboratory Press, pp. 8.46-8.52 and pp. 11.2-11.19.*
Anonymous, UniParc Accession No. UPI00035CA1D7 (2013).
Hawkins et al., Proteins Structure Function Bioinfomatics, vol. 74, No. 3, pp. 566-582 (2009).
Thrash et al., EMBL Accession No. AAMN01000001 (2006).
Thrash et al., UniProt Accession No. A3TJ83 (2007).
Thrash et al., Journal of Bacteriology, vol. 193, No. 2, pp. 584-585 (2011).
Yoshida et al., UniProt Accession No. K6VM97 (2013).
Yu et al., International Journal of Systematic and Evolutionary Microbiology, vol. 62, No. 2, pp. 384-389 (2011).
Anonymous, NCBI Reference sequence WP_009776702.1 (2013).

* cited by examiner

*Primary Examiner* — Yong D Pak
(74) *Attorney, Agent, or Firm* — Elias Lambiris

(57) ABSTRACT

The present invention relates to animal feed or animal feed additives comprising polypeptides having protease activity and uses thereof. Specifically, the proteases are serine S1 proteases from *Janibacter, Terracoccus and Knoellia*, all belonging to the family Intrasporangiaceae of the suborder Micrococcineae. The proteases have a high activity at a broad pH-range (pH 3-7) and are thus highly active during the entire passage through the digestive tract. It also relates to the methods for producing the proteases and for using the proteases to improve animal performance and the nutritional value of animal feed.

11 Claims, 3 Drawing Sheets

Specification includes a Sequence Listing.

POLYPEPTIDES HAVING SERINE PROTEASE ACTIVITY AND POLYNUCLEOTIDES ENCODING SAME AND THEIR APPLICATION IN ANIMAL FEED

CROSS-REFERENCE TO RELATED APPLICATIONS

This application is a 35 U.S.C. 371 national application of international application no. PCT/EP2015/075512 filed Nov. 3, 2015, which claims priority or the benefit under 35 U.S.C. 119 of European application no. 14191691.6 filed Nov. 4, 2014. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to animal feed or animal feed additives comprising polypeptides having protease activity and uses thereof. It also relates to the methods for producing the proteases and for using the proteases to improve animal performance and the nutritional value of animal feed.

Background of the Invention

In the use of proteases in animal feed (in vivo), and/or the use of such proteases for treating vegetable proteins (in vitro) it is noted that proteins are essential nutritional factors for animals and humans. Most livestock and many human beings get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many types of fish, the stomach is strongly acidic with a pH potentially as low as 1-2, while the intestine has a more neutral pH of around 6-7.5. Apart from the stomach and intestine, poultry also have a crop preceding the stomach. The pH in the crop is mostly determined by the feed ingested and hence typically lies in the range of pH 4-6. Protein digestion by a protease may occur along the entire digestive tract, provided that the protease is active and survives the conditions in the digestive tract. Hence, proteases which are highly acid stable and so can survive in the gastric environment and at the same time are efficiently active at the broad range of physiological pH of the digestive tract in the target animal are especially desirable.

Since animal feed is often formulated in pelleted form, in which steam is applied in the pelleting process, it is also desirable that proteases used in animal feed are capable of remaining active after exposure to said steam treatment.

In order to produce a protease for industrial use, it is important that the protease is produced in high yields making the product available in sufficient quantities in order to be able to provide the protease at a favourable price.

DESCRIPTION OF THE RELATED ART

Proteases from the S1 family are known in the art and for use in animal feed. For example, WO 01/58275 discloses the use of acid stable proteases of the subtilisin family in animal feed. WO 01/58276 discloses the use of acid-stable proteases derived from *Nocardiopsis* sp. NRRL 18262 (a 10R protease), as well as a protease derived from *Nocardiopsis alba* DSM 14010 in animal feed. WO 04/072221, WO 04/111220, WO 04/111223, WO 05/035747 and WO 05/123911 disclose proteases related to the 10R protease and their use in animal feed. WO 04/072279 discloses the use of other proteases in animal feed. WO 04/034776 discloses the use of a subtilisin/keratinase, PWD-1 from *B. Licheniformis*, in the feed of poultry.

Soybean and maize are two highly used protein sources in farming and therefore it is important that the protease has good activity on such substrates. There are a number of disclosures showing activity on soybean-maize meal from proteases from various bacterial sources, such as *Kribbella* species (WO 2013/026796), *Saccharopolyspora erythraea* (WO 2013/110766 and WO 2014/122161), *Saccharomonospora viridis* (WO 2013/189972), *Saccharothrix australiensis* (WO 2013/041689) and *Dactylosporangium* species (WO 2014/096259).

Furthermore, proteases isolated from other bacterial species, such as *Janibacter* sp., are known in the art. Thrash et al. carried out a whole genome shotgun of the bacteria *Janibacter* sp. HTCC2649 as described in "Genome sequence of the Marine *Janibacter* Sp. Strain HTCC2649", 2011, J. Bacteriol. 193:584-585, which has been submitted to the EMBL/GenBank under accession number AAMN01000001. From this genome sequencing, a polypeptide having Uniprot number A3TJ83 (SEQ ID NO: 2 herein) was annotated as a serine protease.

Yoshida et al. carried out a whole genome shotgun of the bacteria *Austwickia chelonae* NBRC 105200 which was submitted to the EMBL/GenBank/DDBJ databases from which a peptidase (Uniprot: K6VM97, SEQ ID NO: 9) was annotated having 62.1% sequence identity to SEQ ID NO: 5 (corresponding to the mature polypeptide of SEQ ID NO: 2 and 4 herein).

Commercial products comprising a protease and marketed for use in animal feed include RONOZYME® ProAct (DSM NP/Novozymes), Axtra® (Du Pont), Avizyme® (Du Pont), Porzyme® (Du Pont), Allzyme™ (Alltech), Versazyme® (BioResources, Int.), Poultrygrow™ (Jefo) and Cibenza® DP100 (Novus).

However, there is still a need to find proteases which demonstrate improved properties within the field of animal feed.

SUMMARY OF THE INVENTION

The present invention relates to an animal feed or animal feed additive comprising one or more polypeptides having protease activity, wherein the polypeptide is selected from the group consisting of:
(a) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;
(b) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 14;
(c) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 20;
(d) a polypeptide encoded by a polynucleotide that hybridizes under low stringency conditions, medium stringency conditions, medium-high stringency conditions, high stringency conditions or very-high stringency conditions with:
  (i) the mature polypeptide coding sequence of SEQ ID NO: 1;
  (ii) the mature polypeptide coding sequence of SEQ ID NO: 10;
  (iii) the mature polypeptide coding sequence of SEQ ID NO: 16; or
  (iv) the full-length complement of (i), (ii) or (iii);
(e) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
(f) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 10;
(g) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 16;
(h) a variant of SEQ ID NO: 5, SEQ ID NO: 14 or SEQ ID NO: 20, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(i) a fragment of the polypeptide of (a), (b), (c), (d), (e), (f), (g) or (h) that has protease activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

The present invention further relates to the use of the protease of the invention in animal feed, methods for preparing an animal feed; methods of improving the nutritional value of an animal feed; methods for the treatment of proteins; methods for increasing digestibility and/or solubility of protein; methods for improving one or more performance parameters in an animal and methods of producing the polypeptides of the invention.

Overview of Sequence Listing

SEQ ID NO: 1 is the DNA sequence of the S1 protease 1 from *Janibacter* sp. HTCC2649.
SEQ ID NO: 2 is the amino acid sequence as deduced from SEQ ID NO: 1.
SEQ ID NO: 3 is the DNA sequence of the recombinant expressed DNA sequence from SEQ ID NO: 1.
SEQ ID NO: 4 is the amino acid sequence as deduced from SEQ ID NO: 3.
SEQ ID NO: 5 is the amino acid sequence of the mature S1 protease 1 from *Janibacter* sp. HTCC2649.
SEQ ID NO: 6 is the *Bacillus clausii* secretion signal.
SEQ ID NO: 7 is the DNA sequence of protease 10R (WO 05/035747, SEQ ID NO: 1).
SEQ ID NO: 8 is the amino acid sequence of protease 10R (WO 05/035747, SEQ ID NO: 2).
SEQ ID NO: 9 is the amino acid sequence of a peptidase from *Austwickia chelonae* NBRC 105200 (Uniprot: K6VM97).
SEQ ID NO: 10 is the DNA sequence of the S1 protease 1 from *Terracoccus* sp.
SEQ ID NO: 11 is the amino acid sequence as deduced from SEQ ID NO: 10.
SEQ ID NO: 12 is the DNA sequence of the recombinant expressed DNA sequence from SEQ ID NO: 10.
SEQ ID NO: 13 the amino acid sequence as deduced from SEQ ID NO: 12.
SEQ ID NO: 14 is the amino acid sequence of the mature S1 protease 1 from *Terracoccus* sp.
SEQ ID NO: 15 is the conserved motif VCG[E/Q] KVGQP.
SEQ ID NO: 16 is the DNA sequence of the S1 protease 1 from *Knoellia flava*.
SEQ ID NO: 17 is the amino acid sequence as deduced from SEQ ID NO: 16 (Uniprot: A0A0A0JF07).
SEQ ID NO: 18 is the DNA sequence of the codon optimized synthetic gene of SEQ ID NO: 16.
SEQ ID NO: 19 is the amino acid sequence as deduced from SEQ ID NO: 18.
SEQ ID NO: 20 is the amino acid sequence of the mature S1 protease 1 from *Knoellia flava*.

DEFINITIONS

Figure 1:
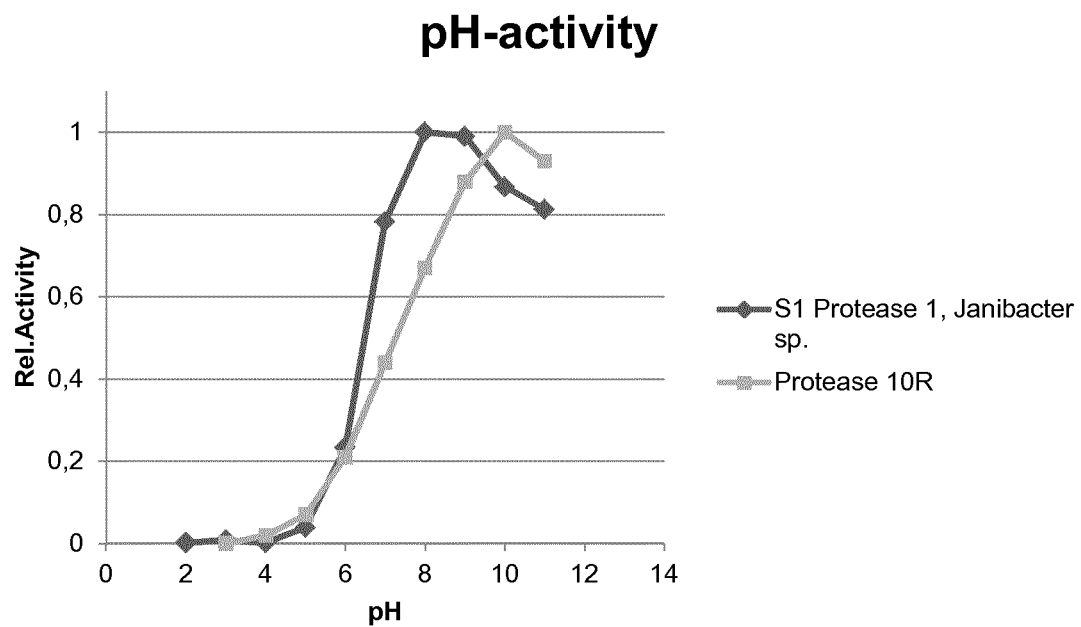
FIG. 1 shows the pH-activity profile of the S1 protease 1 from *Janibacter* sp. HTCC2649 compared to protease 10R on the Suc-AAPF-pNA substrate at 25° C.

Activity of the polypeptide on soybean-maize meal: The term "activity of the polypeptide on soybean-maize meal" means that the protease activity of the enzyme was determined on soybean meal-maize meal mixed in a 30:70 ratio using the o-Phthaldialdehyde (OPA) assay as described herein. Examples of assay-pH-values are pH 3.0, 4.0, 5.0, 6.0 and 7.0. Examples of assay-temperatures are 30, 35, 40, 45 and 50° C. Examples of assay-times are 2, 3 and 4 hours. Examples of enzyme concentrations are 50, 100, 150, 200, 250 and 300 mg enzyme protein/kg dry matter of substrate.

In a preferred embodiment, the activity of the polypeptide on soybean-maize meal was determined by adding soybean meal-maize meal mixed in a 30:70 ratio (1 g) to buffers containing 100 mM succinic acid, 100 mM HEPES, 100 mM CHES, 100 mM CAPS, 1 mM CaCl2, 150 mM KCl, 0.01% Triton X-100 (10 mL) that had been prepared and adjusted using HCl or NaOH to a pH value such that after soybean-maize meal substrate had been mixed with assay buffer, the final pH of the slurry was pH 3.0, 4.0, 5.0, 6.0 or 7.0; then mixing an aliquot of substrate slurry (2 mL) for 30 min; adding protease (200 mg enzyme protein/kg dry matter) dissolved in 100 µl 100 mM sodium acetate buffer (9.565 g/L NaOAc, 1.75 g/L acetic acid, 5 mM $CaCl_2$, 0.01% BSA, 0.01% Tween20, pH 6.0); incubating the samples for 3 hours at 40° C. (500 rpm); centrifuging the samples (10 min, 4000 rpm, 0° C.); and collecting the supernatants for analysis using the o-Phthaldialdehyde (OPA) assay (herein called "soybean-maize meal assay"). In another preferred embodiment, the activity of the polypeptide on soybean-maize meal is determined as described in example 4 herein.

In an embodiment, the polypeptides of the present invention have at least 30%, e.g., at least 40%, at at least 65%, at least 70%, at least 80%, at least 90%, at least 95%, or at least 100% of the activity on soybean-maize meal at pH 4 as the polypeptide of SEQ ID NO: 5. In an embodiment, the polypeptides of the present invention have at least 40%, e.g., at least 65%, at least 70%, at least 80%, at least 90%, at least 95%, or at least 100% of the activity on soybean-maize meal at pH 5 as the polypeptide of SEQ ID NO: 5.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Animal: The term "animal feed" refers to all animals except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Composition: The term "composition" refers to a composition comprising a carrier and at least one enzyme of the present invention. The compositions described herein may be mixed with an animal feed and referred to as a "mash feed."

Concentrates: The term "concentrates" means feed with high protein and energy concentrations, such as fish meal, molasses, oligosaccharides, sorghum, seeds and grains (either whole or prepared by crushing, milling, etc from e.g. corn, oats, rye, barley, wheat), oilseed press cake (e.g. from cottonseed, safflower, sunflower, soybean, rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The term "European Production Efficacy Factor" is one term which determines production efficiency and takes into account feed conversion, mortality and daily gain. EEF is calculated as [(survival rate (%)×body weight gain (kg))/(Study duration in days×FCR)]×100.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide having one or more (e.g., several) amino acids absent from the amino and/or carboxyl terminus of a mature polypeptide; wherein the fragment has protease activity. In one aspect, a fragment contains at least 173 amino acid residues (e.g., amino acids 16 to 188 of SEQ ID NO: 2, SEQ ID NO: 4 or SEQ ID NO: 5), at least 177 amino acid residues (e.g., amino acids 12 to 188 of SEQ ID NO: 2, SEQ ID NO: 4 or SEQ ID NO: 5), at least 181 amino acid residues (e.g., amino acids 10 to 190 of SEQ ID NO: 2, SEQ ID NO: 4 or SEQ ID NO: 5), at least 185 amino acid residues (e.g., amino acids 9 to 193 of SEQ ID NO: 2, SEQ ID NO: 4 or SEQ ID NO: 5), at least 190 amino acid residues (e.g., amino acids 7 to 196 of SEQ ID NO: 2, SEQ ID NO: 4 or SEQ ID NO: 5), or at least 195 amino acid residues (e.g., amino acids 5 to 199 of SEQ ID NO: 2, SEQ ID NO: 4 or SEQ ID NO: 5).

In another aspect, a fragment contains at least 174 amino acid residues (e.g., amino acids 16 to 189 of SEQ ID NO: 11, SEQ ID NO: 13 or SEQ ID NO: 14), at least 178 amino acid residues (e.g., amino acids 12 to 189 of SEQ ID NO: 11, SEQ ID NO: 13 or SEQ ID NO: 14), at least 182 amino acid residues (e.g., amino acids 10 to 191 of SEQ ID NO: 11, SEQ ID NO: 13 or SEQ ID NO: 14), at least 186 amino acid residues (e.g., amino acids 9 to 194 of SEQ ID NO: 11, SEQ ID NO: 13 or SEQ ID NO: 14), at least 191 amino acid residues (e.g., amino acids 7 to 197 of SEQ ID NO: 11, SEQ ID NO: 13 or SEQ ID NO: 14), or at least 196 amino acid residues (e.g., amino acids 5 to 200 of SEQ ID NO: 11, SEQ ID NO: 13 or SEQ ID NO: 14).

In another aspect, a fragment contains at least 174 amino acid residues (e.g., amino acids 16 to 189 of SEQ ID NO: 17, SEQ ID NO: 19 or SEQ ID NO: 20), at least 178 amino acid residues (e.g., amino acids 12 to 189 of SEQ ID NO: 17, SEQ ID NO: 19 or SEQ ID NO: 20), at least 182 amino acid residues (e.g., amino acids 10 to 191 of SEQ ID NO: 17, SEQ ID NO: 19 or SEQ ID NO: 20), at least 186 amino acid residues (e.g., amino acids 9 to 194 of SEQ ID NO: 17, SEQ ID NO: 19 or SEQ ID NO: 20), at least 191 amino acid residues (e.g., amino acids 7 to 197 of SEQ ID NO: 17, SEQ ID NO: 19 or SEQ ID NO: 20), or at least 196 amino acid residues (e.g., amino acids 5 to 200 of SEQ ID NO: 17, SEQ ID NO: 19 or SEQ ID NO: 20).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 203 of SEQ ID NO: 2 and amino acids −200 to −171 of SEQ ID NO: 2 are a signal peptide based on the SignalP program (Nielsen et al., 1997, *Protein Engineering*

10: 1-6). In another aspect, the mature polypeptide is amino acids 1 to 203 of SEQ ID NO: 4 (herein defined as SEQ ID NO: 5) based on EDMAN N-terminal sequencing data and intact MS data and amino acids −197 to −171 of SEQ ID NO: 4 are a signal peptide.

In another aspect, the mature polypeptide is amino acids 1 to 204 of SEQ ID NO: 11 and amino acids −196 to −171 of SEQ ID NO: 11 are a signal peptide based on the SignalP program (Nielsen et al., 1997, *Protein Engineering* 10: 1-6). In another aspect, the mature polypeptide is amino acids 1 to 204 of SEQ ID NO: 13 (herein defined as SEQ ID NO: 14) based on EDMAN N-terminal sequencing data and intact MS data and amino acids −197 to −171 of SEQ ID NO: 13 are a signal peptide.

In another aspect, the mature polypeptide is amino acids 1 to 204 of SEQ ID NO: 17 and amino acids −198 to −170 of SEQ ID NO: 17 are a signal peptide based on the SignalP program (Nielsen et al., 1997, *Protein Engineering* 10: 1-6). In another aspect, the mature polypeptide is amino acids 1 to 204 of SEQ ID NO: 19 (herein defined as SEQ ID NO: 20) based on EDMAN N-terminal sequencing data and intact MS data and amino acids −198 to −170 of SEQ ID NO: 19 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 601 to 1209 of SEQ ID NO: 1 and nucleotides 1 to 90 of SEQ ID NO: 1 encode a signal peptide based on the SignalP program (Nielsen et al., 1997, supra). In another aspect, the mature polypeptide coding sequence is nucleotides 592 to 1200 of SEQ ID NO: 3 based on EDMAN N-terminal sequencing data and intact MS data of the polypeptide of SEQ ID NO: 4 and nucleotides 1 to 81 of SEQ ID NO: 3 encode a signal peptide.

In another aspect, the mature polypeptide coding sequence is nucleotides 589 to 1200 of SEQ ID NO: 10 and nucleotides 1 to 78 of SEQ ID NO: 10 encode a signal peptide based on the SignalP program (Nielsen et al., 1997, supra). In another aspect, the mature polypeptide coding sequence is nucleotides 592 to 1203 of SEQ ID NO: 12 based on EDMAN N-terminal sequencing data and intact MS data of the polypeptide of SEQ ID NO: 13 and nucleotides 1 to 81 of SEQ ID NO: 12 encode a signal peptide.

In another aspect, the mature polypeptide coding sequence is nucleotides 595 to 1206 of SEQ ID NO: 16 and nucleotides 1 to 87 of SEQ ID NO: 16 encode a signal peptide based on the SignalP program (Nielsen et al., 1997, supra). In another aspect, the mature polypeptide coding sequence is nucleotides 589 to 1200 of SEQ ID NO: 18 and nucleotides 1 to 81 of SEQ ID NO: 18 encode a signal peptide based on EDMAN N-terminal sequencing data and intact MS data of the polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the order Micrococcales (formerly known as Micrococcineae), wherein the term order is the taxonomic rank. In another preferred embodiment, the polypeptide is obtained or obtainable from the family Intrasporangiaceae, wherein the term family is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Performance parameters: the term "performance parameters" means one of more of the terms selected from the list consisting of body weight gain, European Production Efficiency Factor (EPEF), European Production Efficacy Factor (EFF) and FCR. The term "improving one or more performance parameters" means that there is an increase in body weight gain, an increase in European Production Efficiency Factor (EPEF), an increase in European Production Efficacy Factor (EFF) and/or a decrease in FCR in one or more animals.

Protease: The term "protease" is defined herein as an enzyme that hydrolyses peptide bonds. This definition of protease also applies to the protease-part of the terms "parent protease" and "protease variant," as used herein. The term "protease" includes enzymes belonging to the EC 3.4.21 enzyme group (serine proteases). The EC number refers to Enzyme Nomenclature 1992 from NC-IUBMB, Academic Press, San Diego, Calif., including supplements 1-5 published in 1994, Eur. J. Biochem. 223: 1-5; 1995, Eur. J. Biochem. 232: 1-6; 1996, Eur. J. Biochem. 237: 1-5; 1997, Eur. J. Biochem. 250: 1-6; and 1999, Eur. J. Biochem. 264: 610-650 respectively. The nomenclature is regularly supplemented and updated; see e.g. the World Wide Web (WWW) at http://www.chem.qmw.ac.uk/iubmb/enzyme/index.html.

The proteases of the invention and for use according to the invention are selected from serine proteases of the peptidase family S1 as described in 1993, Biochem. J. 290:205-218 and in MEROPS protease database, release, 9.9 (23 Aug. 2013) (www.merops.ac.uk). The database is described in Rawlings, N. D., Barrett, A. J. and Bateman, A., 2010, "MEROPS: the peptidase database", Nucl. Acids Res. 38: D227-D233.

For determining whether a given protease is a serine protease, and a family S1 protease, reference is made to the above Handbook and the principles indicated therein. Such determination can be carried out for all types of proteases, be it naturally occurring or wild-type proteases; or genetically engineered or synthetic proteases.

Protease activity: The term "protease activity" means proteolytic activity (EC 3.4). Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

There are several protease activity types such as trypsin-like proteases cleaving at the carboxyterminal side of Arg and Lys residues and chymotrypsin-like proteases cleaving at the carboxyterminal side of hydrophobic amino acid residues. Proteases of the invention are serine endopeptidases (EC 3.4.21) with a slightly alkaline pH-optimum (pH optimum 8-9.5).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Suc-AAPF-pNA assay and the Protazyme AK assay. For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

The polypeptides of the present invention have at least 20%, e.g., at least 40%, at least 65%, at least 70%, at least 80%, at least 90%, at least 95%, and at least 100% of the protease activity of the polypeptide of SEQ ID NO: 5. In another embodiment, the polypeptides of the present invention have at least 20%, e.g., at least 40%, at least 65%, at least 70%, at least 80%, at least 90%, at least 95%, and at least 100% of the protease activity of the polypeptide of SEQ ID NO: 14. In another embodiment, the polypeptides of the present invention have at least 20%, e.g., at least 40%, at at least 65%, at least 70%, at least 80%, at least 90%, at least 95%, and at least 100% of the protease activity of the polypeptide of SEQ ID NO: 20.

Roughage: The term "roughage" means dry plant material with high levels of fiber, such as fiber, bran, husks from seeds and grains and crop residues (such as stover, copra, straw, chaff, sugar beet waste).

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Silage: The term "silage" means fermented, high-moisture stored fodder which can be fed to ruminants (cud-chewing animals such as cattle and sheep) or used as a biofuel feedstock for anaerobic digesters. It is fermented and stored in a process called ensilage, ensiling or silaging, and is usually made from grass or cereal crops (e.g. maize, sorghum, oats, rye, timothy etc forage grass plants),) or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.2×SSC, 0.2% SDS at 65° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.2×SSC, 0.2% SDS at 70° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.6×SSC, 0.2% SDS at 70° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.6×SSC, 0.2% SDS at 75° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.3×SSC, 0.2% SDS at 75° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.15×SSC, 0.2% SDS at 75° C.

Subsequence: The term "subsequence" means a polynucleotide having one or more (e.g., several) nucleotides absent from the 5' and/or 3' end of a mature polypeptide coding sequence; wherein the subsequence encodes a fragment having protease activity. In one aspect, a subsequence contains at least 519 nucleotides (e.g., nucleotides 646 to 1164 of SEQ ID NO: 1), at least 531 nucleotides (e.g., nucleotides 634 to 1164 of SEQ ID NO: 1), at least 543 nucleotides (e.g., nucleotides 628 to 1170 of SEQ ID NO: 1), at least 555 nucleotides (e.g., nucleotides 625 to 1179 of SEQ ID NO: 1), at least 570 nucleotides (e.g., nucleotides 619 to 1188 of SEQ ID NO: 1), or at least 585 nucleotides (e.g., nucleotides 613 to 1197 of SEQ ID NO: 1).

In another aspect, a subsequence contains at least 522 nucleotides (e.g., nucleotides 634 to 1155 of SEQ ID NO: 10), at least 534 nucleotides (e.g., nucleotides 622 to 1155 of SEQ ID NO: 10), at least 546 nucleotides (e.g., nucleotides 614 to 1161 of SEQ ID NO: 10), at least 558 nucleotides (e.g., nucleotides 611 to 1170 of SEQ ID NO: 10), at least 573 nucleotides (e.g., nucleotides 605 to 1179 of SEQ ID NO: 10), or at least 588 nucleotides (e.g., nucleotides 599 to 1188 of SEQ ID NO: 10).

In another aspect, a subsequence contains at least 522 nucleotides (e.g., nucleotides 640 to 1161 of SEQ ID NO: 16), at least 534 nucleotides (e.g., nucleotides 628 to 1161 of SEQ ID NO: 16), at least 546 nucleotides (e.g., nucleotides 620 to 1167 of SEQ ID NO: 16), at least 558 nucleotides (e.g., nucleotides 617 to 1176 of SEQ ID NO: 16), at least 573 nucleotides (e.g., nucleotides 611 to 1185 of SEQ ID NO: 16), or at least 588 nucleotides (e.g., nucleotides 605 to 1194 of SEQ ID NO: 16).

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at at least 65%, at least 70%, at least 80%, at least 90%, at least 95%, or at least 100% of the protease activity of SEQ ID NO: 5 and/or SEQ ID NO: 14 and/or SEQ ID NO: 20.

Nomenclature

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Animal Feed or Animal Feed Additives Comprising Polypeptides Having Protease Activity Soybean and maize are two highly used protein sources in farming and therefore it is important that the protease has good activity on such substrates. In addition, proteases which demonstrate high activity across the entire gastrointestinal pH range (i.e. between about pH 3 and pH 7.5) will be of great interest since it could be expected that they are better at degrading the substrate soon after ingestion and throughout much of the GI tract.

It has been discovered that some proteases have surprisingly good pH-activity profiles on a commercially relevant substrate (soybean-maize) and are significantly more active in the lower pH range (4-5) than protease 10R (SEQ ID NO: 8) whilst also maintaining comparable activity at neutral pH.

Thus in the first aspect, the invention relates to an animal feed or animal feed additive comprising one or more polypeptides having protease activity, wherein:
  (a) the polypeptide is a serine protease of the peptidase family S1;
  (b) the polypeptide has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH;

(c) the polypeptide has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH; and (d) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

In a preferred embodiment, the polypeptide comprises one or more motifs VCG[E/Q]KVGQP (SEQ ID NO: 15).

In a preferred embodiment, the activity of the polypeptide on soybean-maize meal was determined using the soybean-maize meal assay as described in the definitions section herein.

In an embodiment, the polypeptide has less than 20 times, such as less than 15 times, less than 10 times, less than 9 times, less than 8 times the activity of Protease 10R (SEQ ID NO: 8) on soybean-maize meal at pH 4 and less than 20 times, such as less than 15 times, less than 10 times, less than 9 times, less than 8 times the activity of Protease 10R (SEQ ID NO: 8) on soybean-maize meal at pH 5. In an embodiment, the polypeptide has less than 200% of the activity, such as less than 180%, less than 170%, less than 160%, less than 150%, less than 140%, less than 130% or less than 125% of the activity on soybean-maize meal at pH 7 compared to Protease 10R (SEQ ID NO: 8) at the same pH.

In an embodiment, the polypeptide has at least 2 times higher activity on soybean-maize meal at pH 4, at least 2 times higher activity on soybean-maize meal at pH 5 and at least 75% of the activity of Protease 10R (SEQ ID NO: 8) at pH7. In an embodiment, the polypeptide has at least 2 times higher activity on soybean-maize meal at pH 4, at least 2 times higher activity on soybean-maize meal at pH 5 and at least 90% of the activity of Protease 10R (SEQ ID NO: 8) at pH7. In an embodiment, the polypeptide has at least 2.5 times higher activity on soybean-maize meal at pH 4, at least 2.25 times higher activity on soybean-maize meal at pH 5 and at least 75% of the activity of Protease 10R (SEQ ID NO: 8) at pH7. In an embodiment, the polypeptide has at least 2.5 times higher activity on soybean-maize meal at pH 4, at least 2.25 times higher activity on soybean-maize meal at pH 5 and at least 90% of the activity of Protease 10R (SEQ ID NO: 8) at pH7.

In an embodiment, the polypeptide has at least 3 times higher activity on soybean-maize meal at pH 4, at least 2.5 times higher activity on soybean-maize meal at pH 5 and at least 75% of the activity of Protease 10R (SEQ ID NO: 8) at pH7. In an embodiment, the polypeptide has at least 3 times higher activity on soybean-maize meal at pH 4, at least 2.5 times higher activity on soybean-maize meal at pH 5 and at least 90% of the activity of Protease 10R (SEQ ID NO: 8) at pH7. In an embodiment, the polypeptide has at least 3.5 times higher activity on soybean-maize meal at pH 4, at least 2.75 times higher activity on soybean-maize meal at pH 5 and at least 75% of the activity of Protease 10R (SEQ ID NO: 8) at pH7. In an embodiment, the polypeptide has at least 3.5 times higher activity on soybean-maize meal at pH 4, at least 2.75 times higher activity on soybean-maize meal at pH 5 and at least 90% of the activity of Protease 10R (SEQ ID NO: 8) at pH7.

In an embodiment, the polypeptide has at least 4 times higher activity on soybean-maize meal at pH 4, at least 3 times higher activity on soybean-maize meal at pH 5 and at least 75% of the activity of Protease 10R (SEQ ID NO: 8) at pH7. In an embodiment, the polypeptide has at least 4 times higher activity on soybean-maize meal at pH 4, at least 3 times higher activity on soybean-maize meal at pH 5 and at least 90% of the activity of Protease 10R (SEQ ID NO: 8) at pH7. In an embodiment, the polypeptide has at least 4.5 times higher activity on soybean-maize meal at pH 4, at least 3 times higher activity on soybean-maize meal at pH 5 and at least 75% of the activity of Protease 10R (SEQ ID NO: 8) at pH7. In an embodiment, the polypeptide has at least 4.5 times higher activity on soybean-maize meal at pH 4, at least 3 times higher activity on soybean-maize meal at pH 5 and at least 90% of the activity of Protease 10R (SEQ ID NO: 8) at pH7.

In a preferred embodiment, the polypeptide is obtained or obtainable from the order Micrococcales. In an even more preferred embodiment, the polypeptide is obtained or obtainable from the family Intrasporangiaceae.

In a second aspect, the invention relates to an animal feed or animal feed additive comprising one or more polypeptides having protease activity, wherein:

(a) the polypeptide is a serine protease of the peptidase family S1;

(b) the polypeptide has at least 25% of the activity, such as at least 30%, at least 35% or at least 40% of the activity on soybean-maize meal at pH 4 compared to the activity at pH 7;

(c) the polypeptide has at least 45% of the activity, such as at least 50%, at least 55%, at least 60%, or at least 65% of the activity on soybean-maize meal at pH 5 compared to the activity at pH 7; and (d) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

In a preferred embodiment, the polypeptide comprises one or more motifs VCG[E/Q]KVGQP (SEQ ID NO: 15).

In a preferred embodiment, the activity of the polypeptide on soybean-maize meal was determined using the soybean-maize meal assay as described in the definitions section herein.

In an embodiment, the polypeptide has less than 100% of the activity, such as less than 90%, less than 80%, less than 75% or less than 70% of the activity on soybean-maize meal at pH 4 compared to the activity at pH 7 and less than 95%, such as less than 90%, less than 85% or less than 80% of the activity on soybean-maize meal at pH 5 compared to the activity at pH 7. In an embodiment, the polypeptide has less than 200% of the activity, such as less than 180%, less than 170%, less than 160%, less than 150%, less than 140%, less than 130% or less than 125% of the activity on soybean-maize meal at pH pH 7 compared to Protease 10R (SEQ ID NO: 8) at the same pH.

In an embodiment, the polypeptide has at least 25% of the activity at pH 4 compared to the activity at pH 7, the polypeptide has at least 45% of the activity at pH 5 compared to the activity at pH 7 and the polypeptide has at least 75% of the activity of Protease 10R (SEQ ID NO: 8) at pH 7. In an embodiment, the polypeptide has at least 25% of the activity at pH 4 compared to the activity at pH 7, the polypeptide has at least 45% of the activity at pH 5 compared to the activity at pH 7 and the polypeptide has at least 90% of the activity of Protease 10R (SEQ ID NO: 8) at pH 7.

In an embodiment, the polypeptide has at least 30% of the activity at pH 4 compared to the activity at pH 7, the polypeptide has at least 55% of the activity at pH 5 compared to the activity at pH 7 and the polypeptide has at least 75% of the activity of Protease 10R (SEQ ID NO: 8) at pH 7. In an embodiment, the polypeptide has at least 30% of the activity at pH 4 compared to the activity at pH 7, the polypeptide has at least 55% of the activity at pH 5 compared to the activity at pH 7 and the polypeptide has at least 90% of the activity of Protease 10R (SEQ ID NO: 8) at pH 7.

In an embodiment, the polypeptide has at least 35% of the activity at pH 4 compared to the activity at pH 7, the polypeptide has at least 60% of the activity at pH 5 compared to the activity at pH 7 and the polypeptide has at least 75% of the activity of Protease 10R (SEQ ID NO: 8) at pH 7. In an embodiment, the polypeptide has at least 35% of the activity at pH 4 compared to the activity at pH 7, the polypeptide has at least 60% of the activity at pH 5 compared to the activity at pH 7 and the polypeptide has at least 90% of the activity of Protease 10R (SEQ ID NO: 8) at pH 7.

In an embodiment, the polypeptide has at least 40% of the activity at pH 4 compared to the activity at pH 7, the polypeptide has at least 65% of the activity at pH 5 compared to the activity at pH 7 and the polypeptide has at least 75% of the activity of Protease 10R (SEQ ID NO: 8) at pH 7. In an embodiment, the polypeptide has at least 40% of the activity at pH 4 compared to the activity at pH 7, the polypeptide has at least 65% of the activity at pH 5 compared to the activity at pH 7 and the polypeptide has at least 90% of the activity of Protease 10R (SEQ ID NO: 8) at pH 7.

In a preferred embodiment, the polypeptide is obtained or obtainable from the order Micrococcales. In an even more preferred embodiment, the polypeptide is obtained or obtainable from the family Intrasporangiaceae.

In a third aspect, the invention relates to an animal feed or animal feed additive comprising one or more polypeptides having protease activity, wherein:
(a) the polypeptide is a serine protease of the peptidase family S1; and
(b) the polypeptide is obtained or obtainable from the family Intrasporangiaceae.

In an embodiment, the polypeptide comprises one or more motifs VCG[E/Q]KVGQP (SEQ ID NO: 15).

In an embodiment, the polypeptide has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH.

In an embodiment, the polypeptide has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH.

In an embodiment, the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

In a preferred embodiment, the polypeptide:
(a) has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH;
(b) has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH; and
(c) has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

In a preferred embodiment, the polypeptide:
(a) comprises one or more motifs VCG[E/Q]KVGQP (SEQ ID NO: 15);
(b) has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH;
(c) has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH; and
(d) has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

In a fourth aspect, the invention relates to an animal feed or animal feed additive comprising one or more polypeptides having protease activity, wherein the polypeptide has at at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 2. In an embodiment, the polypeptide comprises one or more motifs VCG[E/Q] KVGQP (SEQ ID NO: 15).

In an embodiment, the polypeptide has been isolated. An animal feed or animal feed additive preferably comprises or consists of the amino acid sequence of SEQ ID NO: 2 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 173 amino acids, such as least 177 amino acids, at least 181 amino acids, at least 185 amino acids, at least 190 amino acids, at least 195 amino acids or at least 200 amino acids. In another embodiment, the animal feed or animal feed additive comprises or consists of the mature polypeptide of SEQ ID NO: 2. In another embodiment, the animal feed or animal feed additive comprises or consists of amino acids 1 to 203 of SEQ ID NO: 2.

In a continuation of the fourth aspect, the invention relates to an animal feed or animal feed additive comprising one or more polypeptides having protease activity, wherein the polypeptide has at least 65% sequence identity to SEQ ID NO: 5. In an embodiment, the polypeptide has at least 70% sequence identity to SEQ ID NO: 5. In an embodiment, the polypeptide has at least 75% sequence identity to SEQ ID NO: 5. In an embodiment, the polypeptide has at least 80% sequence identity to SEQ ID NO: 5. In an embodiment, the polypeptide has at least 81% sequence identity to SEQ ID NO: 5. In an embodiment, the polypeptide has at least 82% sequence identity to SEQ ID NO: 5. In an embodiment, the polypeptide has at least 83% sequence identity to SEQ ID NO: 5. In an embodiment, the polypeptide has at least 84% sequence identity to SEQ ID NO: 5. In an embodiment, the polypeptide has at least 85% sequence identity to SEQ ID NO: 5. In an embodiment, the polypeptide has at least 86% sequence identity to SEQ ID NO: 5. In an embodiment, the polypeptide has at least 87% sequence identity to SEQ ID NO: 5. In an embodiment, the polypeptide has at least 88% sequence identity to SEQ ID NO: 5. In an embodiment, the polypeptide has at least 89% sequence identity to SEQ ID NO: 5. In an embodiment, the polypeptide has at least 90% sequence identity to SEQ ID NO: 5. In an embodiment, the polypeptide has at least 91% sequence identity to SEQ ID NO: 5. In an embodiment, the polypeptide has at least 92% sequence identity to SEQ ID NO: 5. In an embodiment, the polypeptide has at least 93% sequence identity to SEQ ID NO: 5. In an embodiment, the polypeptide has at least 94% sequence identity to SEQ ID NO: 5. In an embodiment, the polypeptide has at least 95% sequence identity to SEQ ID NO: 5. In an embodiment, the polypeptide has at least 96% sequence identity to SEQ ID NO: 5. In an embodiment, the polypeptide has at least 97% sequence identity to SEQ ID NO: 5. In an embodiment, the polypeptide has at least 98% sequence identity to SEQ ID NO: 5. In an embodiment, the polypeptide has at least 99% sequence identity to SEQ ID NO: 5. In an embodiment, the polypeptide comprises one or more motifs VCG[E/Q]KVGQP (SEQ ID NO: 15).

In a continuation of the fourth aspect, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 5. In an embodiment, the polypeptide comprises one or more motifs VCG[E/Q]KVGQP (SEQ ID NO: 15).

In an embodiment, the polypeptide has been isolated. An animal feed or animal feed additive preferably comprises or consists of the amino acid sequence of SEQ ID NO: 5 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 173 amino acids, such as least 177 amino acids, at least 181 amino acids, at least 185 amino acids, at least 190 amino acids, at least 195 amino acids or at least 200 amino acids. In another embodiment, the animal feed or animal feed additive comprises or consists of amino acids 1 to 203 of SEQ ID NO: 5.

In a continuation of the fourth aspect, the invention relates to an animal feed or animal feed additive comprising one or more polypeptides having protease activity encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, (ii) the mature polypeptide coding sequence of SEQ ID NO: 3, or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In a continuation of the fourth aspect, the invention relates to an animal feed or animal feed additive comprising one or more polypeptides having protease activity encoded by a polynucleotide having a sequence identity to the mature polypeptide coding sequence of SEQ ID NO: 1 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fourth aspect, the invention relates to an animal feed or animal feed additive comprising one or more polypeptides having protease activity encoded by a polynucleotide having a sequence identity to the mature polypeptide coding sequence of SEQ ID NO: 3 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fourth aspect, the invention relates to an animal feed or animal feed additive comprising one or more variants of SEQ ID NO: 5, wherein the variant has protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 5 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 5 is not more than 10, e.g., 1, 2, 3, 4, 5, 6, 7, 8, 9 or 10. In another embodiment, the number of substitutions and/or deletions and/or insertions in SEQ ID NO: 5 is not more than 10, e.g., 1, 2, 3, 4, 5, 6, 7, 8, 9 or 10. In a further embodiment, the number of substitutions in SEQ ID NO: 5 is not more than 10, e.g., 1, 2, 3, 4, 5, 6, 7, 8, 9 or 10. In an embodiment, the polypeptide comprises one or more motifs VCG[E/Q]KVGQP (SEQ ID NO: 15).

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The peptidases of family S1 contain the catalytic triad in the order His, Asp, Ser. Mutation of any of the amino acids of the catalytic triad will result in change or loss of enzyme activity or substrate specificity. The amino acids of the catalytic triad of the S1 protease 1 as isolated from *Janibacter* sp. HTCC2649 (SEQ ID NO: 5) are positions His-35, Asp-62 and Ser-148. The amino acids of the catalytic triad of the S1 protease 1 as isolated from *Terracoccus* sp. (SEQ ID NO: 14) are positions His-35, Asp-62 and Ser-149. The amino acids of the catalytic triad of the S1 protease 1 as isolated from *Knoellia flava* (SEQ ID NO: 20) are positions His-35, Asp-62 and Ser-149.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Carbohydrate molecules are often attached to a polypeptide from a fungal source during post-translational modification. In order to aid mass spectrometry analysis, the polypeptide can be incubated with an endoglycosidase to deglycosylate each N-linked position. For every deglycosylated N-linked site, one N-acetyl hexosamine remains on the protein backbone.

In the fifth aspect, the invention relates to an animal feed or animal feed additive comprising one or more polypeptides having protease activity, wherein the polypeptide has at at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 11. In an embodiment, the polypeptide comprises one or more motifs VCG[E/Q]KVGQP (SEQ ID NO: 15).

In an embodiment, the polypeptide has been isolated. An animal feed or animal feed additive preferably comprises or consists of the amino acid sequence of SEQ ID NO: 11 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 174 amino acids, such as at least 178 amino acids, at least 182 amino acids, at least 186 amino acids, at least 191 amino acids, at least 196 amino acids or at least 201 amino acids. In another embodiment, the animal feed or animal feed additive comprises or consists of the mature polypeptide of SEQ ID NO: 11. In another embodiment, the animal feed or animal feed additive comprises or consists of amino acids 1 to 204 of SEQ ID NO: 11.

In a continuation of the fifth aspect, the invention relates to an animal feed or animal feed additive comprising one or more polypeptides having protease activity, wherein the polypeptide has at least 65% sequence identity to SEQ ID NO: 14. In an embodiment, the polypeptide has at least 70% sequence identity to SEQ ID NO: 14. In an embodiment, the polypeptide has at least 75% sequence identity to SEQ ID NO: 14. In an embodiment, the polypeptide has at least 80% sequence identity to SEQ ID NO: 14. In an embodiment, the polypeptide has at least 81% sequence identity to SEQ ID NO: 14. In an embodiment, the polypeptide has at least 82% sequence identity to SEQ ID NO: 14. In an embodiment, the polypeptide has at least 83% sequence identity to SEQ ID NO: 14. In an embodiment, the polypeptide has at least 84% sequence identity to SEQ ID NO: 14. In an embodiment, the polypeptide has at least 85% sequence identity to SEQ ID NO: 14. In an embodiment, the polypeptide has at least 86% sequence identity to SEQ ID NO: 14. In an embodiment, the polypeptide has at least 87% sequence identity to SEQ ID NO: 14. In an embodiment, the polypeptide has at least 88% sequence identity to SEQ ID NO: 14. In an embodiment, the polypeptide has at least 89% sequence identity to SEQ ID NO: 14. In an embodiment, the polypeptide has at least 90% sequence identity to SEQ ID NO: 14. In an embodiment, the polypeptide has at least 91% sequence identity to SEQ ID NO: 14. In an embodiment, the polypeptide has at least 92% sequence identity to SEQ ID NO: 14. In an embodiment, the polypeptide has at least 93% sequence identity to SEQ ID NO: 14. In an embodiment, the polypeptide has at least 94% sequence identity to SEQ ID NO: 14. In an embodiment, the polypeptide has at least 95% sequence identity to SEQ ID NO: 14. In an embodiment, the polypeptide has at least 96% sequence identity to SEQ ID NO: 14. In an embodiment, the polypeptide has at least 97% sequence identity to SEQ ID NO: 14. In an embodiment, the polypeptide has at least 98% sequence identity to SEQ ID NO: 14. In an embodiment, the polypeptide has at least 99% sequence identity to SEQ ID NO: 14. In an embodiment, the polypeptide comprises one or more motifs VCG[E/Q]KVGQP (SEQ ID NO: 15).

In a continuation of the fifth aspect, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 14. In an embodiment, the polypeptide comprises one or more motifs VCG[E/Q]KVGQP (SEQ ID NO: 15).

In an embodiment, the polypeptide has been isolated. An animal feed or animal feed additive preferably comprises or consists of the amino acid sequence of SEQ ID NO: 14 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 174 amino acids, such as least 178 amino acids, at least 182 amino acids, at least 186 amino acids, at least 191 amino acids, at least 196 amino acids or at least 201 amino acids. In another embodiment, the animal feed or animal feed additive comprises or consists of SEQ ID NO: 14. In another embodiment, the animal feed or animal feed additive comprises or consists of amino acids 1 to 204 of SEQ ID NO: 14.

In a continuation of the fifth aspect, the invention relates to an animal feed or animal feed additive comprising one or more polypeptides having protease activity encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 10, (ii) the mature polypeptide coding sequence of SEQ ID NO: 12, or (iii) the full-length complement of (i) or (ii) (Sambrook et al., 1989, supra). In an embodiment, the polypeptide has been isolated.

In a continuation of the fifth aspect, the invention relates to an animal feed or animal feed additive comprising one or more polypeptides having protease activity encoded by a polynucleotide having a sequence identity to the mature polypeptide coding sequence of SEQ ID NO: 10 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fifth aspect, the invention relates to an animal feed or animal feed additive comprising one or more polypeptides having protease activity encoded by a polynucleotide having a sequence identity to the mature polypeptide coding sequence of SEQ ID NO: 12 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fifth aspect, the invention relates to an animal feed or animal feed additive comprising one or more variants of SEQ ID NO: 14, wherein the variant has protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 14 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 14 is not more than 10, e.g., 1, 2, 3, 4, 5, 6, 7, 8, 9 or 10. In another embodiment, the number of substitutions and/or deletions and/or insertions in SEQ ID NO: 14 is not more than 10, e.g., 1, 2, 3, 4, 5, 6, 7, 8, 9 or 10. In a further embodiment, the number of substitutions in SEQ ID NO: 14 is not more than 10, e.g., 1, 2, 3, 4, 5, 6, 7, 8, 9 or 10. In an embodiment, the polypeptide comprises one or more motifs VCG[E/Q] KVGQP (SEQ ID NO: 15). Examples of amino acid changes, conservative substitutions and fusion peptides are described in the fourth aspect of the invention.

In the sixth aspect, the invention relates to an animal feed or animal feed additive comprising one or more polypeptides having protease activity, wherein the polypeptide has at at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 17. In an embodiment, the polypeptide comprises one or more motifs VCG[E/Q]KVGQP (SEQ ID NO: 15).

In an embodiment, the polypeptide has been isolated. An animal feed or animal feed additive preferably comprises or consists of the amino acid sequence of SEQ ID NO: 17 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 174 amino acids, such as least 178 amino acids, at least 182 amino acids, at least 186 amino acids, at least 191 amino acids, at least 196 amino acids or at least 201 amino acids. In another embodiment, the animal feed or animal feed additive comprises or consists of the mature polypeptide of SEQ ID NO: 17. In another embodiment, the animal feed or animal feed additive comprises or consists of amino acids 1 to 204 of SEQ ID NO: 17.

In a continuation of the sixth aspect, the invention relates to an animal feed or animal feed additive comprising one or more polypeptides having protease activity, wherein the polypeptide has at least 65% sequence identity to SEQ ID NO: 20. In an embodiment, the polypeptide has at least 70% sequence identity to SEQ ID NO: 20. In an embodiment, the polypeptide has at least 75% sequence identity to SEQ ID NO: 20. In an embodiment, the polypeptide has at least 80% sequence identity to SEQ ID NO: 20. In an embodiment, the polypeptide has at least 81% sequence identity to SEQ ID NO: 20. In an embodiment, the polypeptide has at least 82% sequence identity to SEQ ID NO: 20. In an embodiment, the polypeptide has at least 83% sequence identity to SEQ ID NO: 20. In an embodiment, the polypeptide has at least 84% sequence identity to SEQ ID NO: 20. In an embodiment, the polypeptide has at least 85% sequence identity to SEQ ID NO: 20. In an embodiment, the polypeptide has at least 86% sequence identity to SEQ ID NO: 20. In an embodiment, the polypeptide has at least 87% sequence identity to SEQ ID NO: 20. In an embodiment, the polypeptide has at least 88% sequence identity to SEQ ID NO: 20. In an embodiment, the polypeptide has at least 89% sequence identity to SEQ ID NO: 20. In an embodiment, the polypeptide has at least 90% sequence identity to SEQ ID NO: 20. In an embodiment, the polypeptide has at least 91% sequence identity to SEQ ID NO: 20. In an embodiment, the polypeptide has at least 92% sequence identity to SEQ ID NO: 20. In an embodiment, the polypeptide has at least 93% sequence identity to SEQ ID NO: 20. In an embodiment, the polypeptide has at least 94% sequence identity to SEQ ID NO: 20. In an embodiment, the polypeptide has at least 95% sequence identity to SEQ ID NO: 20. In an embodiment, the polypeptide has at least 96% sequence identity to SEQ ID NO: 20. In an embodiment, the polypeptide has at least 97% sequence identity to SEQ ID NO: 20. In an embodiment, the polypeptide has at least 98% sequence identity to SEQ ID NO: 20. In an embodiment, the polypeptide has at least 99% sequence identity to SEQ ID NO: 20. In an embodiment, the polypeptide comprises one or more motifs VCG[E/Q]KVGQP (SEQ ID NO: 15).

In a continuation of the sixth aspect, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 20. In an embodiment, the polypeptide comprises one or more motifs VCG[E/Q]KVGQP (SEQ ID NO: 15).

In an embodiment, the polypeptide has been isolated. An animal feed or animal feed additive preferably comprises or consists of the amino acid sequence of SEQ ID NO: 20 or an allelic variant thereof; is a fragment missing e.g. 30, 26, 22, 18, 13, 11, 8 or 5 amino acids from the N- and/or C-terminal and having protease activity, or is a fragment that has protease activity wherein the fragment comprises at least 174 amino acids, such as least 178 amino acids, at least 182 amino acids, at least 186 amino acids, at least 191 amino acids, at least 196 amino acids or at least 201 amino acids. In another embodiment, the animal feed or animal feed additive comprises or consists of SEQ ID NO: 20. In another embodiment, the animal feed or animal feed additive comprises or consists of amino acids 1 to 204 of SEQ ID NO: 20.

In a continuation of the sixth aspect, the invention relates to an animal feed or animal feed additive comprising one or more polypeptides having protease activity encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 16, or (ii) the full-length complement of (i) (Sambrook et al., 1989, supra). In an embodiment, the polypeptide has been isolated.

In a continuation of the sixth aspect, the invention relates to an animal feed or animal feed additive comprising one or more polypeptides having protease activity encoded by a polynucleotide having a sequence identity to the mature polypeptide coding sequence of SEQ ID NO: 16 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixth aspect, the invention relates to an animal feed or animal feed additive comprising one or more variants of SEQ ID NO: 20, wherein the variant has protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 20 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 20 is not more than 10, e.g., 1, 2, 3, 4, 5, 6, 7, 8, 9 or 10. In another embodiment, the number of substitutions and/or deletions and/or insertions in SEQ ID NO: 20 is not more than 10, e.g., 1, 2, 3, 4, 5, 6, 7, 8, 9 or 10. In a further embodiment, the number of substitutions in SEQ ID NO: 20 is not more than 10, e.g., 1, 2, 3, 4, 5, 6, 7, 8, 9 or 10. In an embodiment, the polypeptide comprises one or more motifs VCG[E/Q]KVGQP (SEQ ID NO: 15). Examples of amino acid changes, conservative substitutions and fusion peptides are described in the fourth aspect of the invention.

In a preferred embodiment, the polypeptides of the fourth, fifth and sixth aspects of the invention also comprise the properties of the first aspect of the invention.

In a preferred embodiment, the polypeptides of the fourth, fifth and sixth aspects of the invention also comprise the properties of the second aspect of the invention.

In a preferred embodiment, the polypeptides of the fourth, fifth and sixth aspects of the invention also comprise the properties of the third aspect of the invention.

In a preferred embodiment, the polypeptides of the fourth, fifth and sixth aspects of the invention also comprise the properties of the first and second aspects of the invention.

In a preferred embodiment, the polypeptides of the fourth, fifth and sixth aspects of the invention also comprise the properties of the first and third aspects of the invention.

In a preferred embodiment, the polypeptides of the fourth, fifth and sixth aspects of the invention also comprise the properties of the second and third aspects of the invention.

In a preferred embodiment, the polypeptides of the fourth, fifth and sixth aspects of the invention also comprise the properties of the first, second and third aspects of the invention.

Properties

Acidity/Alkalinity Properties

In certain embodiments of the invention the protease of the invention exhibits beneficial properties in respect of pH, such as acid stability and pH optimum. Activity over a broad physiological pH e.g. from 4-7 covers both the upper gastro-intestinal tract (crop pH 4-6; stomach pH in pigs sometimes as high as pH 5-6) as well as the small intestine (pH 6-7). An embodiment of the invention is isolated polypeptides having improved protease activity on soybean-maize meal between pH 3 and 7, such as at pH 3.0, pH 4.0, pH 5.0, pH 6.0 and/or pH 7.0, at 40° C. compared to protease 10R.

Temperature-Activity

The temperature-activity profile of the protease may be determined as described in Example 3. Activity at low temperatures (37-50° C.) can be advantageous for the digestion of proteins in an animal.

In one embodiment, the invention comprises of a protease having a temperature activity profile at pH 7.0 with relative activity of 0.10 or higher at 37° C., relative activity of 0.40 or higher at 50° C., or relative activity of 0.80 or higher at 60° C. when compared to the activity of the protease at 60° C. (cf. Example 3).

A further embodiment of the invention is isolated polypeptides having improved protease activity at e.g. 60° C. or below, such as 50° C. or below, 37° C. or below, or between 37° C. and 60° C., or between 50° C. and 60° C. or at 37° C., or at 50° C. or at 60° C. at pH 7.0 compared to protease 10R at pH 6.5.

Thermostability

Thermostability may be determined as described in Example 5, i.e. using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 5 and/or SEQ ID NO: 14, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 5 and/or SEQ ID NO: 14 and/or SEQ ID NO: 20.

In still further particular embodiments, the thermostable protease of the invention has a melting temperature, $T_m$ (or a denaturation temperature, $T_d$), as determined using Differential Scanning calorimetry (DSC) as described in example 5 (i.e. in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 6 by determining the residual activity of protease molecules after steam treatment at 85° C. or 90° C. for a short time.

Pelleting Stability

Pelleting stability may be determined as described in Example 7 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity according to the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such as Actinobacteria or from a gram-negative bacterium within a phylum such as Proteobacteria.

In one aspect, the polypeptide is a protease from a bacterium of the class Actinobacteria, such as from the order Micrococcales, or from the family Intrasporangiaceae, or from the genera *Janibacter, Terracoccus* or *Knoellia*.

Strains of these taxa are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Janibacter, Terracoccus* or *Knoellia* or a related organism from the Micrococcales and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccha-

*romyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N.

and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; (b) optionally isolating the polypeptide; and (c) recovering the polypeptide. In one aspect, the cell is a *Janibacter* cell. In another aspect, the cell is a *Janibacter* HTCC2649 cell. In another aspect, the cell is a *Terracoccus* cell. In another aspect, the cell is a *Terracoccus* sp. 273MFTsu3.1 cell. In another aspect, the cell is a *Knoellia* cell. In another aspect, the cell is a *Knoellia flava* cell.

The present invention also relates to methods of producing a polypeptide of the present invention, comprising (a) cultivating a recombinant *Bacillus* expression host cell comprising a polynucleotide encoding the polypeptide of the present invention operably linked to one or more control sequences that direct the production of the polypeptide under conditions conducive for production of the polypeptide; (b) optionally isolating the polypeptide; and (c) recovering the polypeptide.

In an embodiment, the *Bacillus* expression host cell is selected from the list consisting of *Bacillus alkalophilus, Bacillus amyloliquefaciens, Bacillus brevis, Bacillus circulans, Bacillus clausii, Bacillus coagulans, Bacillus firmus, Geobacillus stearothermophilus, Bacillus lautus, Bacillus lentus, Bacillus licheniformis, Bacillus megaterium, Bacillus pumilus, Bacillus stearothermophilus, Bacillus subtilis,* and *Bacillus thuringiensis*. In a preferred embodiment, the *Bacillus* expression host cell is selected from the list consisting of *Bacillus licheniformis, Bacillus amyloliquefaciens,* and *Bacillus subtilis*.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

The compositions may comprise a polypeptide of the present invention as the major enzymatic component, e.g., a mono-component composition. Such a composition may further comprise a formulating agent, as described below. Alternatively, the compositions may comprise more than one polypeptide of the present invention (e.g. single activity type composition) and/or multiple enzymatic activities, such as one or more (e.g., several) enzymes selected from the group consisting of phytase, xylanase, galactanase, alpha-galactosidase, further protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

In an embodiment, the composition comprises the polypeptide of the third aspect of the invention and optionally a formulating agent. In an embodiment, the composition comprises the polypeptide of the fourth aspect of the invention and optionally a formulating agent. In an embodiment, the composition comprises the polypeptide of the fifth aspect of the invention and optionally a formulating agent. In an embodiment, the composition comprises the polypeptide of the sixth aspect of the invention and optionally a formulating agent.

Formulating Agent

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol.

For a solid formulation, the formulation may be for example as a granule, spray dried powder or agglomerate. The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In an embodiment, the solid composition is in granulated form. The granule may have a matrix structure where the components are mixed homogeneously. However, the granule typically comprises a core particle and one or more coatings, which typically are salt and/or wax coatings. The core particle can either be a homogeneous blend of protease of the invention optionally combined with one or more additional enzymes and optionally together with one or more salts or an inert particle with the protease of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals.

The salt coating is typically at least 1 μm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

In another embodiment, the composition is a solid composition comprising the protease of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the protease of the invention and a salt coating.

In a further embodiment, the formulating agent is selected from one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: 1, 2-propylene glycol, 1, 3-propylene glycol, sodium sulfate, dextrin, cellulose, sodium thiosulfate and calcium carbonate.

Animal Feed and Animal Feed Additives

The present invention also relates to animal feed compositions and animal feed additives. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one protease as described herein or more than one protease as described herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically a liquid protease/enzyme preparation comprises the protease of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the protease can be prepared by freezing a mixture of liquid enzyme solution with a bulking agent such as ground soybean meal, and then lyophilizing the mixture.

In an embodiment, the composition comprises one or more additional enzymes. In an embodiment, the composition comprises one or more microbes. In an embodiment, the composition comprises one or more vitamins. In an embodiment, the composition comprises one or more minerals. In an embodiment, the composition comprises one or more amino acids. In an embodiment, the composition comprises one or more other feed ingredients.

In another embodiment, the composition comprises one or more of the polypeptides of the invention, one or more formulating agents and one or more additional enzymes. In an embodiment, the composition comprises one or more of the polypeptides of the invention, one or more formulating agents and one or more microbes. In an embodiment, the composition comprises one or more of the polypeptides of the invention, one or more formulating agents and one or more vitamins. In an embodiment, the composition comprises one or more of the polypeptides of the invention and one or more minerals. In an embodiment, the composition comprises the polypeptide of the invention, one or more formulating agents and one or more amino acids. In an embodiment, the composition comprises one or more of the polypeptides of the invention, one or more formulating agents and one or more other feed ingredients.

In a further embodiment, the composition comprises one or more of the polypeptides of the invention, one or more formulating agents and one or more components selected from the list consisting of: one or more additional enzymes; one or more microbes; one or more vitamins; one or more minerals; one or more amino acids; and one or more other feed ingredients.

The final protease concentration in the diet is within the range of 0.01-200 mg protease protein per kg diet, preferably between 0.5-100 mg/kg diet, more preferably 2-50 mg, even more preferably 5-25 mg protease protein per kg animal diet.

It is at present contemplated that the protease is administered in one or more of the following amounts (dosage ranges): 0.01-200; 0.01-100; 0.5-100; 1-50; 5-100; 5-50; 10-100; 0.05-50; 5-25; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity). The protease activity of the feed composition as such is also determined using the same assay, and on the basis of these two determinations, the dosage in mg protease protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (')/0 meaning g additive per 100 g feed). This is so in particular for premixes.

The same principles apply for determining mg protease protein in feed additives. Of course, if a sample is available of the protease used for preparing the feed additive or the feed, the specific activity is determined from this sample (no need to purify the protease from the feed composition or the additive).

Additional Enzymes

In another embodiment, the compositions described herein optionally include one or more enzymes. Enzymes can be classified on the basis of the handbook Enzyme Nomenclature from NC-I UBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41) and beta-glucanase (EC 3.2.1.4 or EC 3.2.1.6), or any combination thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Finase® and Quantum® Blue (AB Enzymes), OptiPhos® (Huvepharma) Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX and Ronozyme® G2 (DSM Nutritional Products), Econase® XT and Barley (AB Vista), Xylathin® (Verenium), Hostazym® X (Huvepharma) and Axtra® XB (Xylanase/beta-glucanase, DuPont).

In a particular embodiment, the composition of the invention comprises a protease (EC 3.4). Examples of commercially available proteases include Ronozyme® ProAct (DSM Nutritional Products).

Microbes

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococcus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, animal feed composition further comprises a bacterium from one or more of the following strains of *Bacillus subtilis:* 3A-P4 (PTA-6506); 15A-P4 (PTA-6507); 22C-P1 (PTA-6508); 2084 (NRRL B-500130); LSSA01 (NRRL-B-50104); BS27 (NRRL B-501 05); BS 18 (NRRL B-50633); and BS 278 (NRRL B-50634).

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{16}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Premix

In an embodiment, the animal feed may include a premix, comprising e.g. vitamins, minerals, enzymes, amino acids, preservatives, antibiotics, other feed ingredients or any combination thereof which are mixed into the animal feed.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Amino Acids

The composition of the invention may further comprise one or more amino acids. Examples of amino acids which are used in animal feed are lysine, alanine, beta-alanine, threonine, methionine and tryptophan.

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Uses

The present invention is also directed to methods for using the polypeptides having protease activity, or compositions thereof, for e.g. animal feed.

Use in Animal Feed

A protease of the invention may also be used in animal feed. In an embodiment, the present invention provides a method for preparing an animal feed composition comprising adding one or more proteases of the present invention to one or more animal feed ingredients.

The one or more proteases of the present invention may also be used in animal feed as feed enhancing enzymes that improve feed digestibility to increase the efficiency of its utilization according to WO 00/21381 and WO 04/026334.

In a further embodiment a protease of the present invention may be used in an animal feed or as a feed additive, where it may provide a positive effect on the animals digestive tract and in this way improve animal performance in accordance to weight gain, feed conversion ratio (FCR), European Production Efficiency Factor (EPEF), European Production Efficacy Factor (EFF) or improved animal health such as decreased mortality rate. FCR is calculated as the feed intake in g/animal relative to the weight gain in g/animal.

In the use according to the invention the proteases can be fed to the animal before, after, or simultaneously with the diet. The latter is preferred.

In a particular embodiment, the form of the protease when it is added to the feed or when it is included in a feed additive is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimizing dosage based upon the desired effect.

For the use in animal feed, however, the protease need not be pure; it may e.g. include other enzymes, in which case it could be termed a protease preparation.

The protease preparation can be (a) added directly to the feed, or (b) it can be used in the production of one or more intermediate compositions such as feed additives or pre-mixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, e.g. an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the proteins, but its hydrolysing influence is so to speak not switched on until later when desired, once suitable hydrolysing conditions are established, or once any enzyme inhibitors are inactivated, or whatever other means could have been applied to postpone the action of the enzyme.

In one embodiment the treatment is a pre-treatment of animal feed or proteins for use in animal feed, i.e. the proteins are hydrolysed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e. the weight of ingested feed relative to weight gain) of the animal might be improved.

The protease can be added to the feed in any form, be it as a relatively pure protease or in admixture with other components intended for addition to animal feed, i.e. in the form of animal feed additives, such as the so-called pre-mixes for animal feed.

Methods of Preparation

In an embodiment, the present invention also relates to a method for preparing an animal feed or feed additive, comprising preparing an animal feed or feed additive comprising an animal feed and a protease of the first aspect of the invention.

In an embodiment, the present invention also relates to a method for preparing an animal feed or feed additive, comprising preparing an animal feed or feed additive comprising an animal feed and a protease of the second aspect of the invention.

In an embodiment, the present invention also relates to a method for preparing an animal feed or feed additive, comprising preparing an animal feed or feed additive comprising an animal feed and a protease of the third aspect of the invention.

In an embodiment, the present invention also relates to a method for preparing an animal feed or feed additive, comprising preparing an animal feed or feed additive comprising an animal feed and a protease of the fourth aspect of the invention.

In an embodiment, the present invention also relates to a method for preparing an animal feed or feed additive, comprising preparing an animal feed or feed additive comprising an animal feed and a protease of the fifth aspect of the invention.

In an embodiment, the present invention also relates to a method for preparing an animal feed or feed additive, comprising preparing an animal feed or feed additive comprising an animal feed and a protease of the sixth aspect of the invention.

Nucleic Acid Constructs, Expression Vectors, Recombinant Host Cells, and Methods for Production of Proteases The present invention also relates to nucleic acid constructs, expression vectors and recombinant host cells comprising such polynucleotides encoding the proteases of the invention.

The present invention also relates to methods of producing a protease, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a protease. The gene may be obtained from any prokaryotic, eukaryotic, or other source.

Preferred Embodiments of the Invention

Preferred embodiments of the invention are described in the set of items below.
1. An animal feed or animal feed additive comprising one or more polypeptides having protease activity, wherein the polypeptide is selected from the group consisting of:
   (a) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
   (b) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;
   (c) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11;
   (d) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 14;
   (e) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17;
   (f) a polypeptide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 20;
   (g) a polypeptide encoded by a polynucleotide that hybridizes under low stringency conditions, medium stringency conditions, medium-high stringency conditions, high stringency conditions or very-high stringency conditions with:
      (i) the mature polypeptide coding sequence of SEQ ID NO: 1;
      (ii) the mature polypeptide coding sequence of SEQ ID NO: 3;

(iii) the mature polypeptide coding sequence of SEQ ID NO: 10;
(iv) the mature polypeptide coding sequence of SEQ ID NO: 12;
(v) the mature polypeptide coding sequence of SEQ ID NO: 16; or
(vi) the full-length complement of (i), (ii), (iii), (iv) or (v);
(h) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
(i) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3;
(j) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 10;
(k) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 12;
(l) a polypeptide encoded by a polynucleotide having at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 16;
(m) a variant of SEQ ID NO: 5, SEQ ID NO: 14 or SEQ ID NO: 20 or the mature polypeptide of SEQ ID NO: 2, SEQ ID NO: 11 or SEQ ID NO: 17, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(n) a fragment of the polypeptide of (a), (b), (c), (d), (e), (f), (g), (h), (i), (j), (k), (l) or (m) that has protease activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

2. The animal feed or animal feed additive of item 1, wherein the polypeptide is obtained or obtainable from the order Micrococcales.

3. The animal feed or animal feed additive of any of items 1 to 2, wherein the polypeptide is obtained or obtainable from the family Intrasporangiaceae.

4. The animal feed or animal feed additive of any of items 1 to 3, wherein:
(a) the polypeptide has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH;
(b) the polypeptide has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH; and
(c) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

5. The animal feed or animal feed additive of any of items 1 to 4, wherein:
(a) the polypeptide has at least 25% of the activity, such as at least 30%, at least 35% or at least 40% of the activity on soybean-maize meal at pH 4 compared to the activity at pH 7;
(b) the polypeptide has at least 45% of the activity, such as at least 50%, at least 55%, at least 60%, or at least 65% of the activity on soybean-maize meal at pH 5 compared to the activity at pH 7; and
(c) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

6. The animal feed or animal feed additive any of items 1 to 5, wherein the polypeptide comprises or consists of SEQ ID NO: 5, SEQ ID NO: 14 or SEQ ID NO: 20, the mature polypeptide of SEQ ID NO: 2, SEQ ID NO: 4, SEQ ID NO: 11, SEQ ID NO: 13, SEQ ID NO: 17 or SEQ ID NO: 19 or amino acids 1 to 203 of SEQ ID NO: 2, amino acids 1 to 203 of SEQ ID NO: 4, amino acids 1 to 203 of SEQ ID NO: 5, amino acids 1 to 204 of SEQ ID NO: 11, amino acids 1 to 204 of SEQ ID NO: 13, amino acids 1 to 204 of SEQ ID NO: 14, amino acids 1 to 204 of SEQ ID NO: 17, amino acids 1 to 204 of SEQ ID NO: 19 or amino acids 1 to 204 of SEQ ID NO: 20.

7. An animal feed or animal feed additive comprising one or more polypeptides having protease activity, wherein:
(a) the polypeptide is a serine protease of the peptidase family S1;
(b) the polypeptide has at least 2 times higher activity, such as at least 2.25 times, at least 2.5 times, at least 2.75 times, at least 3 times, at least 3.25 times, at least 3.5 times, at least 3.75 times or at least 4 times higher activity on soybean-maize meal at pH 4 than the activity of Protease 10R (SEQ ID NO: 8) at the same pH;
(c) the polypeptide has at least 2 times higher activity, such as at least 2.25 times, at least 2.5 times, at least 2.75 times or at least 3 times higher activity on soybean-maize meal at pH 5 than the activity of Protease 10R (SEQ ID NO: 8) at the same pH; and (d) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

8. The animal feed or animal feed additive of item 7, wherein the polypeptide has less than 20 times, such as less than 15 times, less than 10 times, less than 9 times, less than 8 times the activity of Protease 10R (SEQ ID NO: 8) on soybean-maize meal at pH 4 and less than 20 times, such as less than 15 times, less than 10 times, less than 9 times, less than 8 times the activity of Protease 10R (SEQ ID NO: 8) on soybean-maize meal at pH 5.

9. The animal feed or animal feed additive of any of items 7 to 8, wherein the polypeptide has less than 200% of the activity, such as less than 180%, less than 170%, less than 160%, less than 150%, less than 140%, less than 130% or less than 125% of the activity on soybean-maize meal at pH pH 7 compared to Protease 10R (SEQ ID NO: 8) at the same pH.

10. An animal feed or animal feed additive comprising one or more polypeptides having protease activity, wherein:
(a) the polypeptide is a serine protease of the peptidase family S1;
(b) the polypeptide has at least 25% of the activity, such as at least 30%, at least 35% or at least 40% of the activity on soybean-maize meal at pH 4 compared to the activity at pH 7;
(c) the polypeptide has at least 45% of the activity, such as at least 50%, at least 55%, at least 60%, or at least 65% of the activity on soybean-maize meal at pH 5 compared to the activity at pH 7; and
(d) the polypeptide has at least 50% of the activity, such as at at least 65%, at least 70%, at least 75%, at least 80%, at least 85%, at least 90%, at least 95%, at least 100% (i.e. at least the same), or at least 105% of the activity on soybean-maize meal at pH 7 compared to Protease 10R (SEQ ID NO: 8) at the same pH.

11. The animal feed or animal feed additive of item 10, wherein the polypeptide has less than 100% of the activity, such as less than 90%, less than 80%, less than 75% or less than 70% of the activity on soybean-maize meal at pH 4 compared to the activity at pH 7 and less than 95%, such as less than 90%, less than 85% or less than 80% of the activity on soybean-maize meal at pH 5 compared to the activity at pH 7.

12. The animal feed or animal feed additive of any of items 10 to 11, wherein the polypeptide has less than 200% of the activity, such as less than 180%, less than 170%, less than 160%, less than 150%, less than 140%, less than 130% or less than 125% of the activity on soybean-maize meal at pH pH 7 compared to Protease 10R (SEQ ID NO: 8) at the same pH.

13. The animal feed or animal feed additive of any of items 7 to 12, wherein the polypeptide is obtained or obtainable from the order Micrococcales.

14. The animal feed or animal feed additive of any of items 7 to 12, wherein the polypeptide is obtained or obtainable from the family Intrasporangiaceae.

15. An animal feed or animal feed additive comprising one or more polypeptides having protease activity, wherein:
(a) the polypeptide is a serine protease of the peptidase family S1; and
(b) the polypeptide is obtained or obtainable from the family Intrasporangiaceae.

16. The animal feed or animal feed additive of any of items 1 to 15, wherein the polypeptide comprises one or more motifs VCG[E/Q]KVGQP (SEQ ID NO: 15).

17. The animal feed or animal feed additive of any of items 1 to 16 having a crude protein content of 50 to 800 g/kg.

18. The animal feed or animal feed additive of any of items 1 to 17 further comprising one or more components selected from the list consisting of:
one or more additional enzymes;
one or more microbes;
one or more vitamins;
one or more minerals;
one or more amino acids; and
one or more other feed ingredients.

19. The animal feed or animal feed additive of item 18 wherein the additional enzymes are selected from the group comprising of phytase, xylanase, galactanase, alpha-galactosidase, further protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

20. The animal feed or animal feed additive of item 18, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

21. Use of the animal feed or animal feed additive of any of items 1 to 20:
in the preparation of a composition for use in animal feed;
for improving the nutritional value of an animal feed;
for increasing digestible and/or soluble protein in animal feed;
for increasing the degree of hydrolysis of proteins in animal diets;
for improving one or more performance parameters in an animal; and/or
for the treatment of proteins.

22. A method for preparing an animal feed comprising mixing the animal feed additive of any of items 1 to 20 with at least one protein or protein source.

23. A method for improving the nutritional value of an animal feed, wherein the animal feed or animal feed additive of any of items 1 to 20 is added to the feed.

24. A method for the treatment of proteins, comprising the step of adding the animal feed or animal feed additive of any of items 1 to 20 to at least one protein or protein source.

25. A method for increasing digestibility and/or solubility of protein, comprising mixing the animal feed additive of any of claims 1 to 20 with at least one protein or protein source.

26. A method for improving one or more performance parameters in an animal comprising administering the animal feed or animal feed additive of any of items 1 to 20 to one or more animals.

27. The use of item 21 or the method of item 26, wherein the performance parameter is selected from the list consisting of body weight gain (BWG), European Production Efficiency Factor (EPEF) and feed conversion ratio (FCR).

28. A method of producing a polypeptide, comprising:
   (a) cultivating a recombinant *Bacillus* expression host cell comprising a polynucleotide encoding the polypeptide indicated in item 1 operably linked to one or more control sequences that direct the production of the polypeptide under conditions conducive for production of the polypeptide; and
   (b) recovering the polypeptide.

EXAMPLES

Strains

The S1 protease 1 from *Janibacter* Sp. was identified in the public genome sequence of *Janibacter* Sp. Strain HTCC2649 as described in Thrash, J. C.; Cho, J. C.; Bertagnolli, A. D.; Ferriera, S.; Johnson, J.; Vergin, K. L. and Giovannoni, S. J., "Genome sequence of the Marine *Janibacter* Sp. Strain HTCC2649", 2011, *J. Bacteriol.* 193: 584-585. The DNA used herein was obtained synthetically as described in example 1. According to the article, the strain was isolated from water collected at Hydrostation S, 12 miles southeast of Bermuda, from a depth of 10 m.

The S1 protease 1 from *Terracoccus* sp. was identified in the genome sequence of *Terracoccus* sp. 273MFTsu3.1 (from JGI http://genome.jgi.doe.gov/ (taxon id 2522125155, JGI project id 1000316). The DNA used herein was obtained synthetically as described in example 10.

The S1 protease 1 from *Knoellia flava* TL1 was identified in the genome sequence of *Knoellia flava* that was submitted by W. Zhu and G. Wang in August 2013 to the EMBL/GenBank/DDBJ databases. According to Xiang Yu, Yan Du and Gejiao Wang, *International Journal of Systematic and Evolutionary Microbiology* (2012), 62, 384-389, *Knoellia flava* TL1 was isolated form pig manure from a hoggery in Huazhong Agricultural University, Wuhan, Central PR China. The DNA used herein was obtained synthetically as described in example 14.

Protease Assays

1) Suc-AAPF-pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH. 20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in OD$_{405}$ was monitored as a measure of the protease activity.

2) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 6.5, 7.0, 8.0, 9.0, 10.0, and 11.0 with HCl or NaOH.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. OD$_{650}$ was read as a measure of protease activity. A buffer blind was included in the assay (instead of enzyme).

3) O-Pthaldialdehyde (OPA) Assay:
This assay detects primary amines and hence cleavage of peptide bonds by a protease can be measured as the difference in absorbance between a protease treated sample and a control sample. The assay was conducted essentially according to Nielsen et al. (Nielsen, P. M., Petersen, D, Dampmann, C. "Improved method for determining food protein degree of hydrolysis", *J. Food Sci.*, 2001, 66: 642-646).

0.5 ml sample was filtered through a 100 kDa Microcon centrifugal filter (60 min, 11,000 rpm, 5° C.). The samples were diluted appropriately (e.g. 10, 50 or 100 times) in deionizer water and 25 µl of each sample was loaded into a 96 well microtiter plate (5 replicates). 200 µl OPA reagent (100 mM di-sodium tetraborate decahydrate, 3.5 mM sodium dodecyl sulphate (SDS), 5.7 mM di-thiothreitol (DDT), 6 mM o-Phthaldialdehyde) was dispensed into all wells, the plate was shaken (10 sec, 750 rpm) and absorbance measured at 340 nm.

Example 1: Expression of the S1 Protease 1 from *Janibacter* Sp. Strain HTCC2649

Based on the published nucleotide sequence identified as SEQ ID NO: 1, a codon optimized synthetic gene having SEQ ID NO: 3 was synthesized by Gene Art (GENEART AG BioPark, Josef-Engert-Str. 11, 93053, Regensburg, Germany). The synthetic gene was subcloned using ClaI and MluI restriction sites into a *Bacillus* expression vector as described in WO 2012/025577. The S1 protease 1 was expressed with a *Bacillus clausii* secretion signal (with the following amino acid sequence: MKKPLGKIVASTALLIS-VAFSSSIASA, SEQ ID NO: 6) replacing the native secretion signal. The expression plasmid was transformed into *Bacillus subtilis*. The expression cassette was integrated by homologous recombination into the pectate lyase locus. Transformants were selected on LB plates supplemented with 6 µg of chloramphenicol per ml. The recombinant *Bacillus subtilis* clone containing the integrated expression construct was selected and designated as S1 protease 1 from *Janibacter* sp. HTCC2649. It was cultivated on a rotary shaking table in 500 mL baffled Erlenmeyer flasks each containing 100 ml yeast extract-based media. The clone was cultivated for 3 days at 30° C. The enzyme containing supernatants were harvested and the enzyme purified as described in Example 2.

Example 2: Purification of the S1 Protease 1 from *Janibacter* sp. HTCC2649

The culture broth was centrifuged (20000×g, 20 min) and the supernatant was carefully decanted from the precipitate.

The supernatant was filtered through a Nalgene 0.2 μm filtration unit in order to remove the rest of the *Bacillus* host cells. The 0.2 μm filtrate was transferred to 10 mM MES/NaOH, 100 mM $H_3BO_3$, 2 mM $CaCl_2$, pH 5.5 on a G25 Sephadex column (from GE Healthcare). The G25 sephadex transferred enzyme was applied to a SP-sepharose FF column (from GE Healthcare) equilibrated in 20 mM MES/NaOH, pH 5.5. After washing the column extensively with the equilibration buffer, the protease was eluted with a linear gradient between the equilibration buffer and 20 mM MES/NaOH, 0.5 mM $CaCl_2$, 0.5M NaCl, pH 5.5 over five column volumes. The major peak from the SP-sepharose FF column containing the S1 protease 1 from *Janibacter* was pooled and solid ammonium sulphate was added to a final ammonium sulphate concentration of 1.6M $(NH_4)_2SO_4$. The ammonium sulphate adjusted pool was applied to a Phenyl-sepharose FF high substitution (from GE Healthcare) equilibrated in 10 mM MES/NaOH, 100 mM $H_3BO_3$, 2 mM $CaCl_2$, 1.6M $(NH_4)_2SO_4$, pH 6.0. After washing the column extensively with the equilibration buffer, the protease was eluted with a linear gradient between the equilibration buffer and 10 mM MES/NaOH, 100 mM $H_3BO_3$, 2 mM $CaCl_2$, pH 6.0 with 25% 2-propanol over five column volumes. The major peak from the Phenyl-sepharose FF column containing the S1 protease 1 from *Janibacter* was pooled and transferred to 20 mM $CH_3COOH$/NaOH, 1 mM $CaCl_2$, pH 4.5 on a G25 Sephadex column (from GE Healthcare). The G25 sephadex transferred enzyme was applied to a SP-sepharose FF column (from GE Healthcare) equilibrated in 20 mM MES/NaOH, 1 mM $CaCl_2$, pH 4.5. After washing the column extensively with the equilibration buffer, the protease was eluted with a linear NaCl gradient (0-->0.5M) in the same buffer over four column volumes. Fractions from the column were analysed for protease activity (using the Protazyme AK assay at pH 7) and active fractions were further analysed by SDS-PAGE. Fractions, where only one band was seen on the coomassie stained SDS-PAGE gel, were pooled and the pH was adjusted to pH 5.8 with 3% NaOH. The adjusted pool from the SP-sepharose FF column was the purified preparation and was used for further characterization.

Example 3: Characterization of the S1 Protease 1 from *Janibacter* sp. HTCC2649 (SEQ ID NO: 5)

The Protazyme AK assay was used for obtaining the pH-activity profile and the pH-stability profile (residual activity after 2 hours at indicated pH-values). For the pH-stability profile the protease was diluted 8× in the different Assay buffers to reach the pH-values of these buffers and then incubated for 2 hours at 37° C. After incubation, the pH of the protease incubations was transferred to the same pH-value, before assay for residual activity, by dilution in the pH 8.0 Assay buffer. The Protazyme AK assay was used for obtaining the temperature-activity profile at pH 7.0.

The results are shown in Tables 2-4 below. Data for Protease 10R (SEQ ID NO: 8) are included in the tables. For Table 2, the activities are relative to the optimal pH for the enzymes. For Table 3, the activities are residual activities relative to samples, which were kept at stable conditions (5° C., pH 8.0 or pH 9.0). For Table 4, the activities are relative to the optimal temperatures for the enzymes at pH 7.0 or pH 6.5. The Suc-AAPF-pNA assay was used for obtaining the pH-activity profile and the pH-stability profile for Protease 10R and the Protazyme AK assay at pH 6.5 was used for obtaining the temperature-activity profile.

TABLE 2 pH-activity profile at 25° C. as determined using the kinetic Suc-AAPF-pNA assay

| pH | S1 Protease 1 from *Janibacter* sp. HTCC2649 | Protease 10R |
|---|---|---|
| 2 | 0.00 | — |
| 3 | 0.01 | 0.00 |
| 4 | 0.00 | 0.02 |
| 5 | 0.04 | 0.07 |
| 6 | 0.23 | 0.21 |
| 7 | 0.78 | 0.44 |
| 8 | 1.00 | 0.67 |
| 9 | 0.99 | 0.88 |
| 10 | 0.87 | 1.00 |
| 11 | 0.81 | 0.93 |

TABLE 3 pH-stability profile (residual activity after 2 hours at 37° C.) as determined using the kinetic Suc-AAPF-pNA assay

| pH | S1 Protease 1 from *Janibacter* sp. HTCC2649 | Protease 10R |
|---|---|---|
| 2 | 0.00 | 0.78 |
| 3 | 0.01 | 1.03 |
| 4 | 0.97 | 0.99 |
| 5 | 0.98 | 1.00 |
| 6 | 0.98 | 1.03 |
| 7 | 0.97 | 1.01 |
| 8 | 1.03 | 0.98 |
| 9 | 1.00 | 0.99 |
| 10 | 0.97 | 0.99 |
| 11 | 0.91 | 0.86 |
| After 2 hours at 5° C. | 1.00 (at pH 8) | 1.00 (at pH 9) |

TABLE 4

Temperature activity profile at pH 7.0 or pH 6.5 as determined using the Protazyme AK assay

| Temp (° C.) | S1 Protease 1 from *Janibacter* sp. HTCC2649 (pH 7) | Protease 10R (pH 6.5) |
|---|---|---|
| 15 | 0.04 | 0.01 |
| 25 | 0.08 | 0.02 |
| 37 | 0.22 | 0.06 |
| 50 | 0.50 | 0.13 |
| 60 | 1.00 | 0.35 |
| 70 | 0.39 | 0.96 |
| 80 | 0.12 | 1.00 |
| 90 | — | 0.18 |

Figure 2:
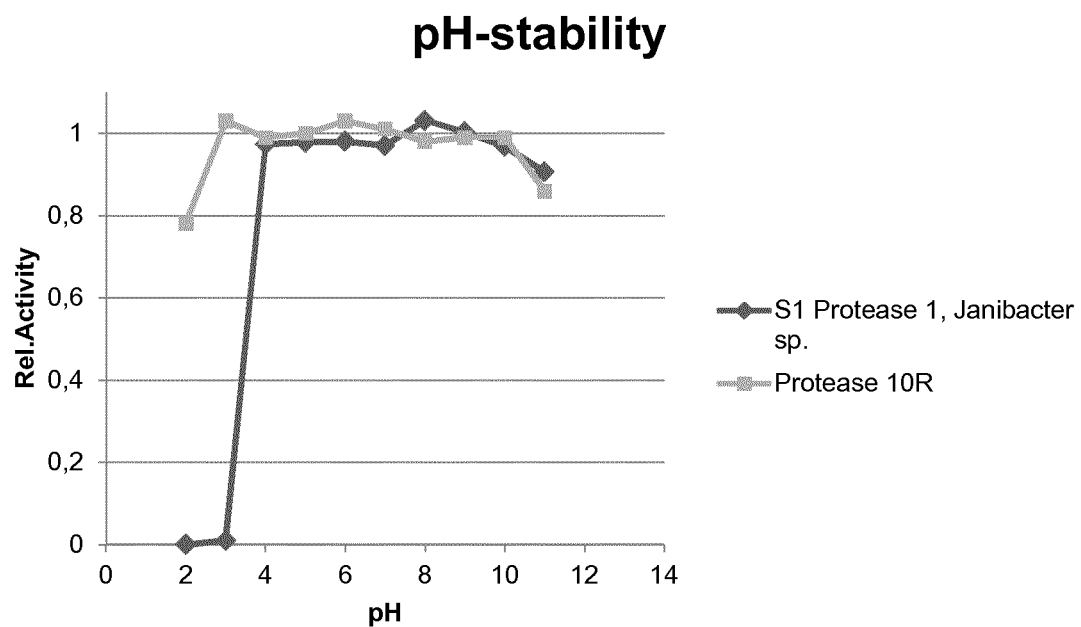
FIG. 2 shows the pH-stability profile of the S1 protease 1 from *Janibacter* sp. HTCC2649 compared to protease 10R (residual activity after 2 hours at 37° C.).
Figure 3:
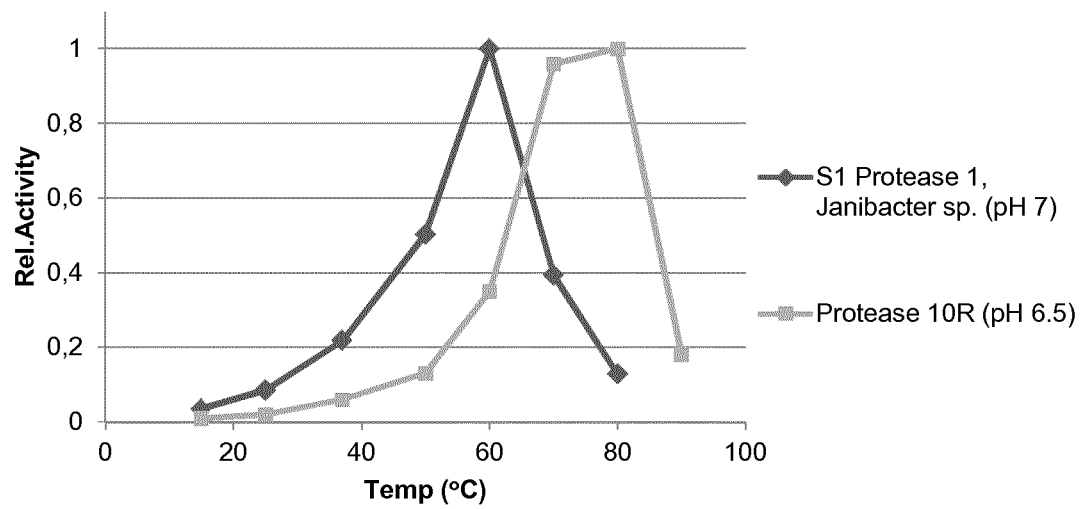
FIG. 3 shows the temperature activity profile of the S1 protease 1 from *Janibacter* sp. HTCC2649 at pH 7.0 compared to protease 10R on Protazyme AK at pH 6.5.

The pH-activity on the Protazyme AK substrate, the pH-stability profile (residual activity after 2 hours at 37° C.) and the temperature activity profile on Protazyme AK at pH 7.0 for the S1 protease 1 from *Janibacter* sp. HTCC2649 compared with the data for protease 10R are also shown as FIGS. 1-3 below.

Other Characteristics for the S1 Protease 1 from *Janibacter* sp. HTCC2649 (SEQ ID NO: 5)

Inhibitor: PMSF.

Determination of the N-terminal sequence was: ANVYGGQ.

The relative molecular weight as determined by SDS-PAGE was approx. $M_r$=24 kDa.

The molecular weight determined by intact molecular weight analysis was 20406.3 Da.

The mature sequence (from EDMAN N-terminal sequencing data and Intact MS data):

(SEQ ID NO: 5)
ANVYGGQQIEFSGYVCSLGFNATKAGAPVFITAGHCGEGYQTFSKNGTTL

GKTQAFSFPGNDYAYSTLASSWTGIGAVDLWTGSARAVTGSSNAAVGTAI

CKSGRTTYWTCGSVQAKNVTVNYDNGDGTTSSVSGLTKSNTCTEGGDSGG

SWMAGNLAQGVTSGGAGYGSSGVCGEKVGQPNIAYFQPVGEILSAYGLTL

KTA

The calculated molecular weight from this mature sequence was 20406.2 Da.

Example 4: Soybean-Maize Meal Activity Assay

An end-point assay using soybean-maize meal as substrate was used for obtaining the activity profile of the proteases at pH 3-7.

Substrate: Soybean meal-maize meal mixed in a 30:70 ratio was obtained from a pilot facility of the Danish Technological Institute, Gl. Ålbovej 1, 6092 Sønder Stenderup. Commercial raw materials were ground (ø2 mm sieve), mixed for 10 minutes then ground (ø1 mm sieve) and mixed for a further 10 minutes. Sieve analysis using a JEL 200 rotary sieve (J. Engelsmann AG, Ludwigshafen, Germany) showed that 1% of the particles were >500 microns, and about 82% were <212 microns.

Assay buffers: 5 buffers containing 100 mM succinic acid, 100 mM HEPES, 100 mM CHES, 100 mM CAPS, 12 mM $CaCl_2$, 150 mM KCl, 0.01% Triton X-100 were prepared and adjusted using HCl or NaOH to a pH value such that after soybean-maize meal substrate (1 g) had been mixed with assay buffer (10 mL) to give a slurry, the final pH of the slurry was one of the following pH's: 3.0, 4.0, 5.0, 6.0 and 7.0.

Substrate slurry (2 mL) was mixed for 30 min before protease addition and incubated for 3 hours at 40° C. (500 rpm). Protease (200 mg enzyme protein/kg dry matter) was dissolved in 100 µl 100 mM sodium acetate buffer (9.565 g/L NaOAc, 1.75 g/L acetic acid, 5 mM $CaCl_2$, 0.01% BSA, 0.01% Tween20, pH 6.0) and added. Samples were centrifuged (10 min, 4000 rpm, 0° C.) and the supernatants collected for analysis using the o-Phthaldialdehyde (OPA) assay.

Figure 4:
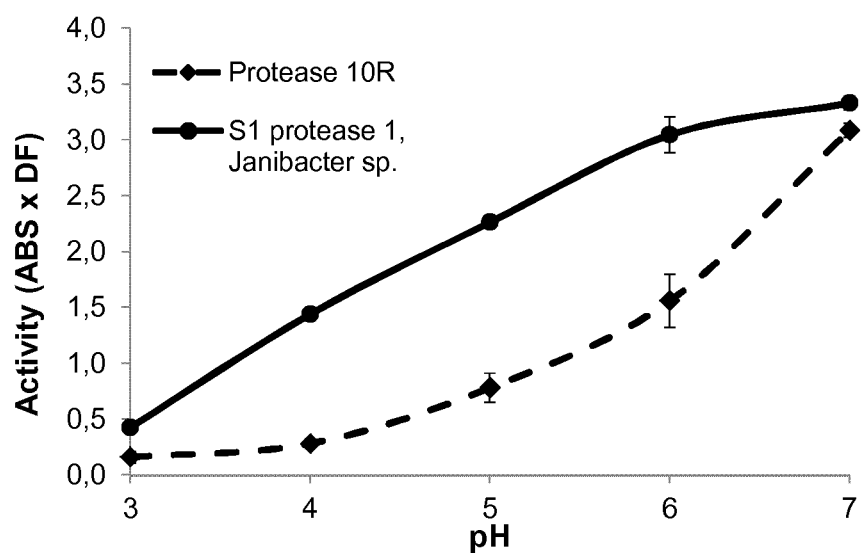
FIG. 4 shows the activity ($OD_{340}$×dilution factor) on soybean-maize meal of the S1 protease 1 from *Janibacter* sp. HTCC2649 compared to the 10R protease. Error bars represent 2 times standard deviation.

The results are shown in table 5 and FIG. 4. The proteolytic activity of the S1 protease 1 from *Janibacter* sp. HTCC2649 on soybean-maize meal increased with increasing pH from pH 3 to pH 7, and the activity in the entire range pH 3-7, and in particular in the range pH 4-6, was significantly higher than for protease 10R. These data indicate that the S1 protease 1 from *Janibacter* sp. HTCC2649 has the potential to be more efficient at protein hydrolysis e.g. in ruminants as well as mono-gastric animals; such as in the crop of broilers where pH is typically between 4 and 6 and in the stomach of pigs where pH varies from approximately 2 to 6 depending on e.g. feed, gastric region and time after feeding.

TABLE 5

Protease activity ($OD_{340}$ × dilution factor) on soybean-maize meal at pH 3.0, 4.0, 5.0, 6.0 and 7.0

| pH | S1 protease 1 from *Janibacter* sp. HTCC2649 (SEQ ID NO: 5) | | Protease 10R (SEQ ID NO: 8) | |
|---|---|---|---|---|
| | Average | Standard deviation | Average | Standard deviation |
| 3.0 | 0.42 | 0.01 | 0.22 | 0.06 |
| 4.0 | 1.44 | 0.02 | 0.30 | 0.10 |
| 5.0 | 2.26 | 0.04 | 0.71 | 0.01 |
| 6.0 | 3.04 | 0.16 | 1.81 | 0.14 |
| 7.0 | 3.33 | 0.06 | 2.92 | 0.11 |

Example 5: Thermostability

An aliquot of the protein sample of protease (purified as described in e.g. Example 2, 9 or 11) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 µm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 6: Steam Stability

Residual activity of the protease after steam treatment may be evaluated using the following assay.

In these experiments a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, samples placed on ice, re-suspended and evaluated with respect to protease activity using e.g. the Suc-AAPF-pNA or o-Phthaldialdehyde (OPA) assay. Each enzyme sample is compared to a similar sample that had not been steam treated in order to calculate residual activity.

Example 7: Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 µm to 850 µm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

Example 8: Expression of 4 Variants of the S1 Protease 1 from *Janibacter* Sp.

Four variants of the S1 protease 1 from *Janibacter* sp. each containing a single amino acid change were made. The amino acid changes were the following: S68N, T71N, T87Q and 590T (numbering based on SEQ ID NO: 5). The 4 variants were constructed by incorporating the changes in the WT DNA sequence (SEQ ID NO: 1) by PCR using the original construct DNA from example 1 as template and primers containing the DNA changes. Two DNA fragments were made for each construct and each fragment covered a part of the gene and either the upstream or downstream flanking region described in example 1. The two fragments were fused together by a SOE PCR reaction to assemble the 2 fragments into one linear vector construct. An aliquot of the SOE PCR product was transformed into *Bacillus subtilis*. Transformants were selected on LB plates supplemented with 6 μg of chloramphenicol per ml. For each variant a recombinant clone with confirmed correct sequence containing the single amino acid change was selected for fermentation in liquid culture. The enzyme containing supernatants were harvested and the 4 variant enzymes purified as described in Example 9.

Example 9: Purification of the S1 Protease 1 from *Janibacter* sp. Variants

Each variant was purified by the following procedure:
The culture broth was centrifuged (20000×g, 20 min) and the supernatant was carefully decanted from the precipitate. The supernatant was filtered through a Nalgene 0.2 μm filtration unit in order to remove the rest of the *Bacillus* host cells. The filtrate was mixed 1:1 with 3.0M $(NH_4)_2SO_4$ to give a final ammonium sulphate concentration of 1.5M $(NH_4)_2SO_4$. The ammonium sulphate adjusted filtrate was applied to a Decyl-agarose column (from UpFront Chromatography) equilibrated in 5 mM MES/NaOH, 50 mM $H_3BO_3$, 1 mM $CaCl_2$, 1.5M $(NH_4)_2SO_4$, pH 6.0. After washing the column extensively with the equilibration buffer, the protease was step-eluted with 10 mM MES/NaOH, 100 mM $H_3BO_3$, 2 mM $CaCl_2$, pH 6.0 with 30% 2-propanol. The elution peak containing the S1 Protease 1 from *Janibacter* sp. variant was collected and transferred to 20 mM $CH_3COOH$/NaOH, 1 mM $CaCl_2$, pH 4.5 on a G25 Sephadex column (from GE Healthcare). The G25 sephadex transferred variant was applied to a SP-sepharose FF column (from GE Healthcare) equilibrated in 20 mM $CH_3COOH$/NaOH, 1 mM $CaCl_2$, pH 4.5. After washing the column extensively with the equilibration buffer, the protease was eluted with a linear NaCl gradient (0-->0.5M) in the same buffer over four column volumes. Fractions from the column were analysed for protease activity (using the Protazyme AK assay at pH 7) and the major activity peak fractions were further analysed by SDS-PAGE. Fractions, where only one band was seen on the coomassie stained SDS-PAGE gel, were pooled as the purified preparation and was used for further characterization.

Example 10: Expression of the S1 Protease 1 from *Terracoccus* Sp.

Based on the nucleotide sequence identified as SEQ ID NO: 10, a codon optimized synthetic gene having SEQ ID NO: 12 was synthesized by Gene Art (GENEART AG BioPark, Josef-Engert-Str. 11, 93053, Regensburg, Germany). The synthetic gene was subcloned using ClaI and MluI restriction sites into a *Bacillus* expression vector as described in WO 2012/025577. The S1 protease 1 was expressed with a *Bacillus clausii* secretion signal (with the following amino acid sequence: MKKPLGKIVASTALLIS-VAFSSSIASA, SEQ ID NO: 6) replacing the native secretion signal. The expression plasmid was transformed into *Bacillus subtilis*. The expression cassette was integrated by homologous recombination into the pectate lyase locus. Transformants were selected on LB plates supplemented with 6 μg of chloramphenicol per ml. The recombinant *Bacillus subtilis* clone containing the integrated expression construct was selected and designated as S1 protease 1 from *Terracoccus* sp. It was cultivated on a rotary shaking table in 500 mL baffled Erlenmeyer flasks each containing 100 ml yeast extract-based media. The clone was cultivated for 3 days at 30° C. The enzyme containing supernatants were harvested and the enzyme purified as described in Example 9.

Example 11: Purification of the S1 Protease 1 from *Terracoccus* Sp.

The culture broth was centrifuged (20000×g, 20 min) and the supernatant was carefully decanted from the precipitate. The supernatant was filtered through a Nalgene 0.2 μm filtration unit in order to remove the rest of the *Bacillus* host cells. The pH of the 0.2 μm filtrate was adjusted to pH 8.0 with 3% NaOH and the solution was applied to a MEP Hypercel column (from Pall Corporation) equilibrated in 20 mM Tris/HCl, 1 mM $CaCl_2$, pH 8.0. After washing the column extensively with the equilibration buffer, the protease was step-eluted with 20 mM $CH_3COOH$/NaOH, 1 mM $CaCl_2$, pH 4.5. The elution peak containing the S1 Protease 1 from *Terracoccus* sp. was collected and diluted 3× with demineralized water to reduce the conductivity. The pH of the solution was adjusted to pH 4.5 and applied to a SOURCE 30S column (from GE Healthcare) equilibrated in 20 mM $CH_3COOH$/NaOH, 1 mM $CaCl_2$, pH 4.5. After washing the column extensively with the equilibration buffer, the protease was eluted with a linear gradient between the equilibration buffer and 20 mM $CH_3COOH$/NaOH, 1 mM $CaCl_2$, 0.5M NaCl, pH 4.5 over five column volumes. Fractions from the column were analysed for protease activity (using the Suc-AAPF-pNA assay at pH 8) and the major activity peak was pooled and finally the pH was adjusted to pH 5.0 with 3% NaOH. The pH adjusted pool was the purified Preparation and was Used for Further Characterization.

Example 12: Characterization of the S1 Protease 1 from *Terracoccus* sp. (SEQ ID NO: 14) and the S1 Protease 1 from *Janibacter* sp. Variants The Suc-AAPF-pNA assay was used for obtaining the pH-activity profile and the pH-stability profile for the S1

Protease 1 from *Terracoccus* sp. The Protazyme AK assay was used for obtaining the pH-activity profiles and the pH-stability profiles for the S1 Protease 1 from *Janibacter* sp. variants. For the pH-stability profiles the proteases were diluted 8-10× in the different Assay buffers to reach the pH-values of these buffers and then incubated for 2 hours at 37° C. After incubation, the pH of the protease incubations was transferred to the same pH-value, before assay for residual activity, by dilution in the pH 8.0 Assay buffer. The Protazyme AK assay was used for obtaining the temperature-activity profile at pH 7.0.

The results are shown in Tables 6-8 below. Data for Protease 10R are included in the tables. For Table 6, the activities are relative to the optimal pH for the enzymes. For Table 7, the activities are residual activities relative to samples, which were kept at stable conditions (5° C., pH 8.0 or pH 9.0). For Table 8, the activities are relative to the optimal temperatures for the enzymes at pH 7.0 or pH 6.5. The Suc-AAPF-pNA assay was used for obtaining the pH-activity profile and the pH-stability profile for Protease 10R and the Protazyme AK assay at pH 6.5 was used for obtaining the temperature-activity profile.

TABLE 6 pH-activity profile

| pH | S1 Protease 1 from *Terracoccus* sp. | S1 Protease 1 from *Janibacter* sp. variant S68N | S1 Protease 1 from *Janibacter* sp. variant T71N | S1 Protease 1 from *Janibacter* sp. variant T87Q | S1 Protease 1 from *Janibacter* sp. variant S90T | Protease 10R |
|---|---|---|---|---|---|---|
| 2 | 0.00 | 0.00 | 0.01 | 0.01 | 0.02 | — |
| 3 | 0.00 | 0.00 | 0.00 | 0.00 | 0.05 | 0.00 |
| 4 | 0.00 | 0.00 | 0.01 | 0.02 | 0.02 | 0.02 |
| 5 | 0.02 | 0.01 | 0.00 | 0.00 | 0.00 | 0.07 |
| 6 | 0.18 | 0.23 | 0.23 | 0.22 | 0.29 | 0.21 |
| 7 | 0.60 | 0.67 | 0.76 | 0.66 | 0.69 | 0.44 |
| 8 | 0.94 | 1.00 | 1.00 | 1.00 | 1.00 | 0.67 |
| 9 | 1.00 | 0.96 | 0.93 | 0.87 | 0.92 | 0.88 |
| 10 | 0.97 | 0.71 | 0.71 | 0.69 | 0.72 | 1.00 |
| 11 | 0.76 | 0.68 | 0.69 | 0.70 | 0.73 | 0.93 |

TABLE 7 pH-stability profile (residual activity after 2 hours at 37° C.)

| pH | S1 Protease 1 from *Terracoccus* sp. | S1 Protease 1 from *Janibacter* sp. variant S68N | S1 Protease 1 from *Janibacter* sp. variant T71N | S1 Protease 1 from *Janibacter* sp. variant T87Q | S1 Protease 1 from *Janibacter* sp. variant S90T | Protease 10R |
|---|---|---|---|---|---|---|
| 2 | 0.01 | 0.00 | 0.00 | 0.00 | 0.00 | 0.78 |
| 3 | 0.02 | 0.00 | 0.00 | 0.01 | 0.00 | 1.03 |
| 4 | 0.91 | 0.91 | 0.90 | 0.86 | 0.85 | 0.99 |
| 5 | 0.98 | 1.02 | 1.00 | 1.01 | 1.02 | 1.00 |
| 6 | 1.01 | 0.98 | 1.01 | 0.97 | 0.98 | 1.03 |
| 7 | 0.98 | 1.01 | 0.96 | 0.94 | 0.95 | 1.01 |
| 8 | 0.98 | 1.06 | 0.97 | 0.92 | 0.97 | 0.98 |
| 9 | 1.02 | 1.05 | 0.96 | 1.02 | 0.93 | 0.99 |
| 10 | 1.00 | 1.00 | 0.97 | 0.99 | 0.93 | 0.99 |
| 11 | 0.92 | 0.77 | 0.82 | 0.85 | 0.68 | 0.86 |
| After 2 hours at 5° C. | 1.00 (at pH 8) | 1.00 (at pH 8) | 1.00 (at pH 8) | 1.00 (at pH 8) | 1.00 (at pH 8) | 1.00 (at pH 9) |

TABLE 8

Temperature activity profile at pH 7.0 or pH 6.5

| Temp (° C.) | S1 Protease 1 from *Terracoccus* sp. (pH 7) | S1 Protease 1 from *Janibacter* sp. variant S68N (pH 7) | S1 Protease 1 from *Janibacter* sp. variant T71N (pH 7) | S1 Protease 1 from *Janibacter* sp. variant T87Q (pH 7) | S1 Protease 1 from *Janibacter* sp. variant S90T (pH 7) | Protease 10R (pH 6.5) |
|---|---|---|---|---|---|---|
| 15 | 0.02 | 0.05 | 0.05 | 0.04 | 0.04 | 0.01 |
| 25 | 0.05 | 0.09 | 0.10 | 0.08 | 0.07 | 0.02 |
| 37 | 0.13 | 0.23 | 0.19 | 0.21 | 0.20 | 0.06 |
| 50 | 0.46 | 0.64 | 0.62 | 0.56 | 0.64 | 0.13 |
| 60 | 1.00 | 1.00 | 1.00 | 1.00 | 1.00 | 0.35 |

TABLE 8-continued

Temperature activity profile at pH 7.0 or pH 6.5

| Temp (° C.) | S1 Protease 1 from Terracoccus sp. (pH 7) | S1 Protease 1 from Janibacter sp. variant S68N (pH 7) | S1 Protease 1 from Janibacter sp. variant T71N (pH 7) | S1 Protease 1 from Janibacter sp. variant T87Q (pH 7) | S1 Protease 1 from Janibacter sp. variant S90T (pH 7) | Protease 10R (pH 6.5) |
|---|---|---|---|---|---|---|
| 70 | 0.31 | 0.28 | 0.38 | 0.23 | 0.21 | 0.96 |
| 80 | 0.11 | 0.11 | 0.10 | 0.10 | 0.07 | 1.00 |
| 90 | — | — | — | — | — | 0.18 |

Other Characteristics for the S1 Protease 1 from Terracoccus sp.: Inhibitor: PMSF.

Determination of the N-terminal sequence was: ANVYGGQ.

The relative molecular weight as determined by SDS-PAGE was approx. $M_r$=24 kDa.

The molecular weight determined by Intact molecular weight analysis was 20603.4 Da ((M+H)$^+$).

The mature sequence (from EDMAN N-terminal sequencing data and Intact MS data):

```
                                            (SEQ ID NO: 14)
ANVYGGQQIEFSGYVCSLGFNATRGGAPVFVTAGHCGEGYQTFSKGGTTL

GSTQAYSFPGNDYAYSTLTSSWTGVGAVDLYDGVNARRVSGYSNAPVGTA

ICKSGRTTGWTCGSVQAKNVTVNYSNADGSTSTVSGLTKSNTCTEGGDSG

GSWMASTSAQGVTSGGAGYGANSVCGQKVGQPNIAYFQPVDEIVSAYGLT

LKTS
```

The calculated molecular weight from this mature sequence was 20601.2 Da (and the calculated molecular weight for the (M+H)$^+$ peak was 20602.2 Da).

Example 13: Soybean-Maize Meal Activity Assay

An end-point assay, as described in example 4 using soybean-maize meal as substrate, was used for obtaining the activity profile of the proteases at pH 3-7.

Figure 5:
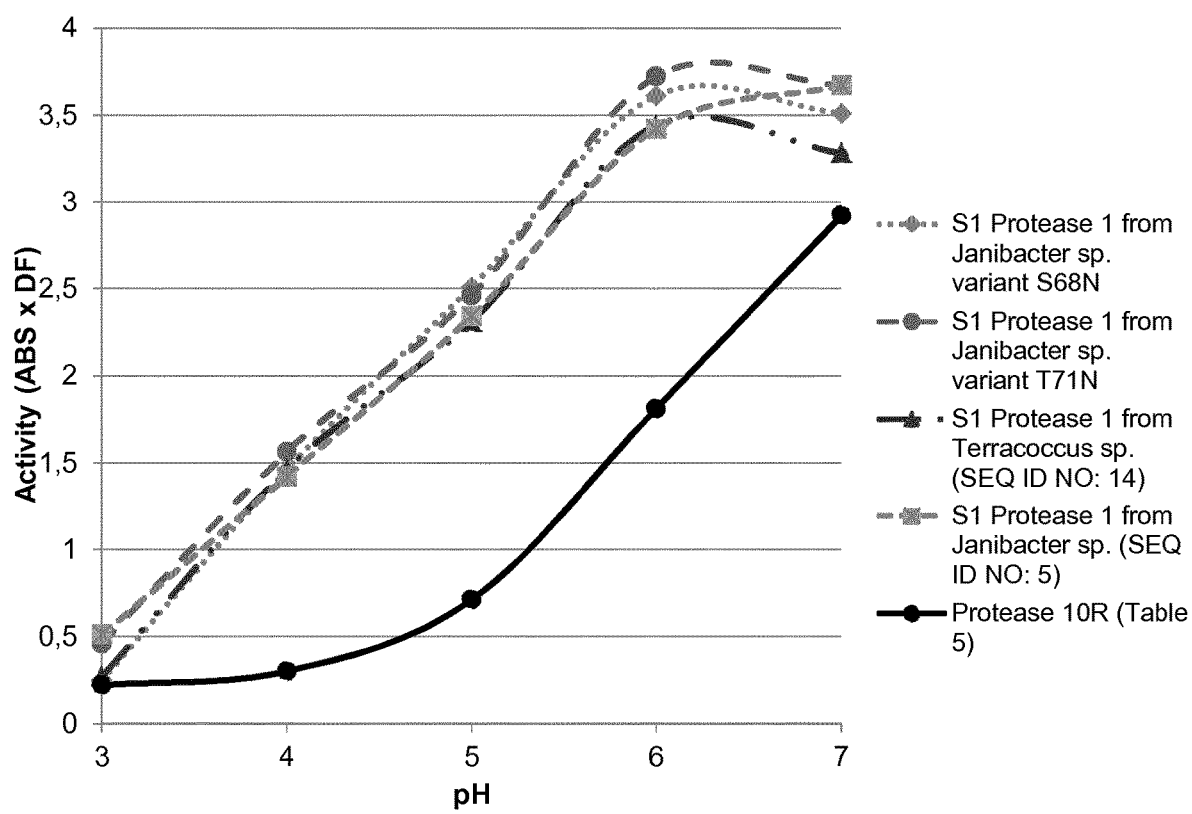
FIG. 5 shows the activity ($OD_{340}$×dilution factor) on soybean-maize meal of the S1 protease 1 from *Janibacter* sp. HTCC2649, *Janibacter* variants S68N and T71N and the S1 protease 1 from *Terracoccus* sp. compared to the 10R protease.

The results are shown in table 9 and FIG. 5. The proteolytic activity of the S1 protease 1 from Janibacter variants as well as the S1 protease 1 from Terracoccus on soybean-maize meal increased with increasing pH from pH 3 to pH 7, and the activity in the entire range pH 3-7, and in particular in the range pH 4-6, was significantly higher than for protease 10R. These data indicate that the S1 protease 1 from Janibacter variants as well as the S1 protease 1 from Terracoccus has the potential to be more efficient at protein hydrolysis e.g. in ruminants as well as mono-gastric animals; such as in the crop of broilers where pH is typically between 4 and 6 and in the stomach of pigs where pH varies from approximately 2 to 6 depending on e.g. feed, gastric region and time after feeding.

In addition, the S1 protease 1 from Janibacter, the variants S68N and T71N and the S1 protease 1 from Terracoccus share very similar pH-activity curves on soybean-maize meal at 40° C. and are significantly different to other proteases known in the art.

TABLE 9

Protease activity ($OD_{340}$ × dilution factor) on soybean-maize meal at pH 3.0, 4.0, 5.0, 6.0 and 7.0

| | S1 Protease 1 from Janibacter sp. (SEQ ID NO: 5) | | S1 Protease 1 from Janibacter sp. variant S68N | | S1 Protease 1 from Janibacter sp. variant T71N | | S1 Protease 1 from Terracoccus sp. (SEQ ID NO: 14) | |
|---|---|---|---|---|---|---|---|---|
| pH | Average | Std Dev | Average | Std Dev | Average | Std Dev | Average | Std Dev |
| 3.0 | 0.51 | 0.01 | 0.25 | 0.08 | 0.46 | 0.07 | 0.27 | 0.10 |
| 4.0 | 1.42 | 0.03 | 1.46 | 0.00 | 1.56 | 0.04 | 1.46 | 0.00 |
| 5.0 | 2.34 | 0.08 | 2.51 | 0.01 | 2.46 | 0.02 | 2.31 | 0.07 |
| 6.0 | 3.42 | 0.05 | 3.61 | 0.03 | 3.72 | 0.08 | 3.44 | 0.04 |
| 7.0 | 3.67 | 0.08 | 3.51 | 0.08 | 3.67 | 0.00 | 3.28 | 0.02 |

Example 14: Expression of the S1 Protease 1 from Knoellia flava TL1

The S1 protease 1 from Knoellia flava having the sequence SEQ ID NO: 17 (SWISSPROT: A0A0A0JF07) was expressed as a codon optimized synthetic gene (SEQ ID NO: 18) with a Bacillus clausii secretion signal replacing the native secretion signal as described in example 10, giving the amino acid sequence SEQ ID NO: 19. The gene was synthesized by Gene Art (GENEART AG BioPark, Josef-Engert-Str. 11, 93053, Regensburg, Germany). The cloning and expression was done as for the S1 protease 1 from Terracoccus sp. described in example 10.

Example 15: Purification of the S1 Protease 1 from Knoellia flava TL1

The culture broth was centrifuged (20000×g, 20 min) and the supernatant was carefully decanted from the precipitate. The supernatant was filtered through a Nalgene 0.2 µm filtration unit in order to remove the rest of the Bacillus host cells. The pH of the 0.2 µm filtrate was adjusted to pH 8.0 with 3M Tris-base and the solution was applied to a MEP Hypercel column (from Pall Corporation) equilibrated in 20 mM Tris/HCl, 1 mM $CaCl_2$, pH 8.0. After washing the column extensively with the equilibration buffer, the protease was step-eluted with 20 mM $CH_3COOH$/NaOH, 1 mM $CaCl_2$, pH 4.5. The elution peak containing the S1 Protease 1 from Knoellia flava TL1 was collected and diluted 3× with demineralized water to reduce the conductivity. The pH of the solution was adjusted to pH 4.5 and applied to a SOURCE 30S column (from GE Healthcare) equilibrated in 20 mM $CH_3COOH$/NaOH, 1 mM $CaCl_2$, pH 4.5. After washing the column extensively with the equilibration buffer, the protease was eluted with a linear gradient between the equilibration buffer and 20 mM CH$_3$COOH/NaOH, 1 mM CaCl$_2$, 0.5M NaCl, pH 4.5 over five column volumes. Fractions from the column were analysed for protease activity (using the Suc-AAPM-pNA assay at pH 8) and the major activity peak was pooled and finally the pH was adjusted to pH 5.5 with 3% NaOH. The pH adjusted pool was the purified preparation and was used for further characterization.

Example 16: Characterization of the S1 Protease 1 from *Knoellia flava* TL1 (SEQ ID NO: 20)

The Suc-AAPM-pNA assay was used for obtaining the pH-activity profile and the pH-stability profile for the S1 Protease 1 from *Knoellia flava* TL1. For the pH-stability profile the protease was diluted 10× in the different Assay buffers to reach the pH-values of these buffers and then incubated for 2 hours at 37° C. After incubation, the pH of the protease incubations was transferred to the same pH-value, before assay for residual activity, by dilution in the pH 9.0 Assay buffer. The Protazyme AK assay was used for obtaining the temperature-activity profile at pH 7.0.

The results are shown in Tables 10 to 12 below. Data for Protease 10R are included in the tables. For Table 10, the activities are relative to the optimal pH for the enzymes. For Table 11, the activities are residual activities relative to samples, which were kept at stable conditions (5° C., pH 9.0). For Table 12, the activities are relative to the optimal temperatures for the enzymes at pH 7.0 or pH 6.5. A Suc-AAPF-pNA assay was used for obtaining the pH-activity profile and the pH-stability profile for Protease 10R and the Protazyme AK assay at pH 6.5 was used for obtaining the temperature-activity profile.

TABLE 10 pH-activity profile

| pH | S1 Protease 1 from *Knoellia flava* TL1 | Protease 10R |
|---|---|---|
| 2 | 0.00 | — |
| 3 | 0.00 | 0.00 |
| 4 | 0.00 | 0.02 |
| 5 | 0.01 | 0.07 |
| 6 | 0.18 | 0.21 |
| 7 | 0.60 | 0.44 |
| 8 | 0.94 | 0.67 |
| 9 | 1.00 | 0.88 |
| 10 | 0.97 | 1.00 |
| 11 | 0.76 | 0.93 |

TABLE 11 pH-stability profile (residual activity after 2 hours at 37° C.)

| pH | S1 Protease 1 from *Knoellia flava* TL1 | Protease 10R |
|---|---|---|
| 2 | 0.00 | 0.78 |
| 3 | 0.62 | 1.03 |
| 4 | 0.96 | 0.99 |
| 5 | 1.01 | 1.00 |
| 6 | 1.01 | 1.03 |
| 7 | 1.02 | 1.01 |
| 8 | 1.01 | 0.98 |
| 9 | 1.01 | 0.99 |
| 10 | 0.95 | 0.99 |
| 11 | 0.05 | 0.86 |

TABLE 11-continued pH-stability profile (residual activity after 2 hours at 37° C.)

| pH | S1 Protease 1 from *Knoellia flava* TL1 | Protease 10R |
|---|---|---|
| After 2 hours at 5° C. | 1.00 (at pH 9) | 1.00 (at pH 9) |

TABLE 12

Temperature activity profile at pH 7.0 or pH 6.5

| Temp (° C.) | S1 Protease 1 from *Knoellia flava* TL1 (pH 7) | Protease 10R (pH 6.5) |
|---|---|---|
| 15 | 0.01 | 0.01 |
| 25 | 0.03 | 0.02 |
| 37 | 0.11 | 0.06 |
| 50 | 0.50 | 0.13 |
| 60 | 1.00 | 0.35 |
| 70 | 0.33 | 0.96 |
| 80 | 0.10 | 1.00 |
| 90 | — | 0.18 |

Other Characteristics for the S1 Protease 1 from *Knoellia flava* TL1
Inhibitor: PMSF.
Determination of the N-terminal sequence was: ANVYGGQ.
The relative molecular weight as determined by SDS-PAGE was approx. M, =24 kDa.
The molecular weight determined by Intact molecular weight analysis was 20697.8 Da.
The mature sequence (from EDMAN N-terminal sequencing data and Intact MS data):

(SEQ ID NO: 20)
ANVYGGQQIEFSGYVCSLGFNATKSGTPVFITAGHCAEGNQTFTRNGTTL

GTTRGWSFPGNDYAYSSLTSSWTGIGAVDLWNGTSARSVTGSSNAAVGTA

ICKSGRTTGWTCGSVQTKNVTVNYNNGDGTYSTVSGLTKSNTCTEGGDSG

GSWMAGNLAQGVTSGGAGYGSNGVCGQKVGQPNIAYFQPIGEILSVYGLT

LKTA

The calculated molecular weight from this mature sequence was 20698.4 Da.

Example 17: Soybean-Maize Meal Activity Assay

An end-point assay, as described in example 4 using soybean-maize meal as substrate, was used for obtaining the activity profile of the proteases at pH 3-7.

The results are shown in table 13. The proteolytic activity of the S1 protease 1 from *Knoellia flava* on soybean-maize meal increased with increasing pH from pH 3 to pH 7, and the activity in the entire range pH 3-7, and in particular in the range pH 4-6, was significantly higher than for protease 10R. These data indicate that the S1 protease 1 from *Knoellia flava* has the potential to be more efficient at protein hydrolysis e.g. in ruminants as well as mono-gastric animals; such as in the crop of broilers where pH is typically between 4 and 6 and in the stomach of pigs where pH varies from approximately 2 to 6 depending on e.g. feed, gastric region and time after feeding.

TABLE 13

Protease activity (OD$_{340}$ × dilution factor) on soybean-maize meal at pH 3.0, 4.0, 5.0, 6.0 and 7.0

| pH | Protease 10R (SEQ ID NO: 8) | S1 protease 1 from *Knoellia Flava* (SEQ ID NO: 20) |
|---|---|---|
| 3.0 | 0.25 ± 0.07 | 0.37 ± 0.02 |
| 4.0 | 0.40 ± 0.09 | 1.02 ± 0.08 |
| 5.0 | 0.91 ± 0.06 | 2.07 ± 0.12 |
| 6.0 | 1.99 ± 0.09 | 3.43 ± 0.17 |
| 7.0 | 3.13 ± 0.20 | 3.97 ± 0.18 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An animal feed comprising soybean, maize, a polypeptide having protease activity, wherein the polypeptide has at least 90% sequence identity to SEQ ID NO: 5, and one or more components selected from the group consisting of:
- one or more additional enzymes;
- one or more microbes;
- one or more vitamins;
- one or more minerals;
- one or more amino acids; and
- one or more other feed ingredients.

2. The animal feed of claim 1, wherein the polypeptide has at least 95% sequence identity to SEQ ID NO: 5.

3. The animal feed of claim 1, wherein the polypeptide has at least 97% sequence identity to SEQ ID NO: 5.

4. The animal feed of claim 1, wherein the polypeptide comprises the amino acid sequence of SEQ ID NO: 5.

5. The animal feed of claim 1, wherein the polypeptide is a variant of SEQ ID NO: 5, comprising the amino acid substitution 68N or 71N.

6. The animal feed of claim 1, wherein the polypeptide comprises one or more motifs VCG[E/Q]KVGQP (SEQ ID NO: 15).

7. The animal feed of claim 1 having a crude protein content of 50 to 800 g/kg.

8. The animal feed of claim 1, wherein the one or more additional enzymes are selected from the group comprising of phytase, xylanase, galactanase, alpha-galactosidase, further protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

9. The animal feed of claim 1, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

10. A method for improving the nutritional value of an animal feed, comprising adding a polypeptide having protease activity, wherein the polypeptide has at least 90% sequence identity to SEQ ID NO: 5, to the animal feed, wherein the animal feed comprises soybean and maize.

11. A method for improving one or more performance parameters in an animal, comprising administering the animal feed of claim 1 to the animal.

* * * * *

SEQUENCE LISTING

```
<160> NUMBER OF SEQ ID NOS: 20

<210> SEQ ID NO 1
<211> LENGTH: 1212
<212> TYPE: DNA
<213> ORGANISM: Janibacter sp. HTCC2649
<220> FEATURE:
<221> NAME/KEY: CDS
<222> LOCATION: (1)..(1209)
<220> FEATURE:
<221> NAME/KEY: sig_peptide
<222> LOCATION: (1)..(90)
<220> FEATURE:
<221> NAME/KEY: mat_peptide
<222> LOCATION: (601)..(1209)

<400> SEQUENCE: 1 atg  tct  cgc  aga  agt  ctc  acc  gtc  ctg  gcc  gga  acc  ctc  tcg  gcc           45
Met  Ser  Arg  Arg  Ser  Leu  Thr  Val  Leu  Ala  Gly  Thr  Leu  Ser  Ala
-200           -195                     -190 gct  gca  gca  gca  acc  gcc  ctc  tgc  gtc  gcg  ccc  gcc  gcg  aac  gct           90
Ala  Ala  Ala  Ala  Thr  Ala  Leu  Cys  Val  Ala  Pro  Ala  Ala  Asn  Ala
-185                -180                     -175 gcg  aac  cct  ggc  ccg  agc  ggc  ccg  agc  agc  ccg  agc  acc  gga  ccc          135
Ala  Asn  Pro  Gly  Pro  Ser  Gly  Pro  Ser  Ser  Pro  Ser  Thr  Gly  Pro
-170                -165                     -160 ctg  gct  gtc  gac  tcc  ggt  gac  tcc  gtc  gcc  gag  atg  tcg  gcg  cag          180
Leu  Ala  Val  Asp  Ser  Gly  Asp  Ser  Val  Ala  Glu  Met  Ser  Ala  Gln
-155                -150                     -145 tgg  ctc  gcg  acg  gag  gag  ggc  ctg  agc  ctc  gag  acc  gcc  cgt  gac          225
Trp  Leu  Ala  Thr  Glu  Glu  Gly  Leu  Ser  Leu  Glu  Thr  Ala  Arg  Asp
-140                -135                     -130 cga  gtg  gcc  gct  cag  gag  ggg  ttg  tcg  cgc  acg  gcg  acg  tcg  ctg          270
Arg  Val  Ala  Ala  Gln  Glu  Gly  Leu  Ser  Arg  Thr  Ala  Thr  Ser  Leu
-125                -120                     -115 gag  acg  tcg  ctc  ggc  gcc  aag  gcc  gtc  ggc  acg  tgg  atc  gac  cag          315
Glu  Thr  Ser  Leu  Gly  Ala  Lys  Ala  Val  Gly  Thr  Trp  Ile  Asp  Gln
-110                -105                     -100 gcg  acg  ggc  gtg  ctc  cac  gtc  aac  gtc  acc  gac  gcc  gcc  gcc  gcg  tcc     363
Ala  Thr  Gly  Val  Leu  His  Val  Asn  Val  Thr  Asp  Ala  Ala  Ala  Ala  Ser
-95                 -90                      -85                     -80 acg  gtg  cgt  tcc  gcc  ggg  gcg  agc  gcc  cgt  gtc  gtc  agc  gcc  gac  aag     411
Thr  Val  Arg  Ser  Ala  Gly  Ala  Ser  Ala  Arg  Val  Val  Ser  Ala  Asp  Lys
                    -75                      -70                     -65 tcc  cgg  ctc  gcc  gcc  tcc  gag  aag  gcc  gcc  acc  gtc  gcc  ggc  aag          459
Ser  Arg  Leu  Ala  Ala  Ser  Glu  Lys  Ala  Ala  Thr  Val  Ala  Gly  Lys
            -60                      -55                     -50 gac  acc  atc  gcg  tcc  tac  gtc  gac  ccg  gtc  acc  aac  aag  gtc  atc  ctc     507
Asp  Thr  Ile  Ala  Ser  Tyr  Val  Asp  Pro  Val  Thr  Asn  Lys  Val  Ile  Leu
```

```
                    -45                 -40                 -35
acg gtg ccc gcg gat cgc gtc gag gcg acc cgc gcc aag atc gcc gac    555
Thr Val Pro Ala Asp Arg Val Glu Ala Thr Arg Ala Lys Ile Ala Asp
    -30                 -25                 -20 ccg tcc gtc acg gtc gag ggc acg cag gcc aag gtc tcc acc cag gcc    603
Pro Ser Val Thr Val Glu Gly Thr Gln Ala Lys Val Ser Thr Gln Ala
-15                 -10                  -5                 -1  1 aac gtc tac ggc ggc cag cag atc gag ttc agc ggc tac gtc tgc tcg    651
Asn Val Tyr Gly Gly Gln Gln Ile Glu Phe Ser Gly Tyr Val Cys Ser
                  5                  10                  15 ctc ggc ttc aac gcc acc aag gcc ggc gcc ccg gtc ttc atc acg gcc    699
Leu Gly Phe Asn Ala Thr Lys Ala Gly Ala Pro Val Phe Ile Thr Ala
             20                  25                  30 ggc cac tgc ggc gag ggc tac cag acc ttc tcc aag aac ggc acg acc    747
Gly His Cys Gly Glu Gly Tyr Gln Thr Phe Ser Lys Asn Gly Thr Thr
 35                  40                  45 ctg ggc aag aca cag gcc ttc tcg ttc ccc ggc aac gac tac gcc tac    795
Leu Gly Lys Thr Gln Ala Phe Ser Phe Pro Gly Asn Asp Tyr Ala Tyr
50                  55                  60                  65 tcg acc ctc gcg tcg agc tgg acc ggc atc ggc gcg gtc gac ctg tgg    843
Ser Thr Leu Ala Ser Ser Trp Thr Gly Ile Gly Ala Val Asp Leu Trp
                 70                  75                  80 acc ggc tcc gca cgg gcg gtg acg ggg tcg agc aac gcc gcc gtc ggc    891
Thr Gly Ser Ala Arg Ala Val Thr Gly Ser Ser Asn Ala Ala Val Gly
             85                  90                  95 acc gcg atc tgc aag tcc ggc cgc acc acc tac tgg acc tgc ggc tcg    939
Thr Ala Ile Cys Lys Ser Gly Arg Thr Thr Tyr Trp Thr Cys Gly Ser
        100                 105                 110 gtc cag gcc aag aac gtc acc gtg aac tac gac aac ggt gac ggc acg    987
Val Gln Ala Lys Asn Val Thr Val Asn Tyr Asp Asn Gly Asp Gly Thr
115                 120                 125 acg agc tcg gtc tcg ggc ctc acg aag tcc aac acc tgc acc gag ggc    1035
Thr Ser Ser Val Ser Gly Leu Thr Lys Ser Asn Thr Cys Thr Glu Gly
130                 135                 140                 145 ggc gac tcc ggc ggc tcc tgg atg gcg ggc aac ctt gcc cag ggc gtg    1083
Gly Asp Ser Gly Gly Ser Trp Met Ala Gly Asn Leu Ala Gln Gly Val
                150                 155                 160 acg agc ggc ggc gcg ggc tac ggc tcc agc gga gtg tgc ggc gag aag    1131
Thr Ser Gly Gly Ala Gly Tyr Gly Ser Ser Gly Val Cys Gly Glu Lys
            165                 170                 175 gtc ggc cag ccc aac atc gcc tac ttc cag ccg gtc ggc gag atc ctc    1179
Val Gly Gln Pro Asn Ile Ala Tyr Phe Gln Pro Val Gly Glu Ile Leu
        180                 185                 190 tcc gcc tac ggc ctc acc ctc aag acg gcc tga                        1212
Ser Ala Tyr Gly Leu Thr Leu Lys Thr Ala
195                 200

<210> SEQ ID NO 2
<211> LENGTH: 403
<212> TYPE: PRT
<213> ORGANISM: Janibacter sp. HTCC2649

<400> SEQUENCE: 2

Met  Ser  Arg  Arg  Ser  Leu  Thr  Val  Leu  Ala  Gly  Thr  Leu  Ser  Ala
-200                 -195                     -190

Ala  Ala  Ala  Ala  Thr  Ala  Leu  Cys  Val  Ala  Pro  Ala  Ala  Asn  Ala
-185                     -180                     -175

Ala  Asn  Pro  Gly  Pro  Ser  Gly  Pro  Ser  Ser  Pro  Ser  Thr  Gly  Pro
-170                     -165                     -160
```

```
Leu  Ala  Val  Asp  Ser  Gly  Asp  Ser  Val  Ala  Glu  Met  Ser  Ala  Gln
-155            -150                 -145

Trp  Leu  Ala  Thr  Glu  Glu  Gly  Leu  Ser  Leu  Glu  Thr  Ala  Arg  Asp
-140            -135                 -130

Arg  Val  Ala  Ala  Gln  Glu  Gly  Leu  Ser  Arg  Thr  Ala  Thr  Ser  Leu
-125            -120                 -115

Glu  Thr  Ser  Leu  Gly  Ala  Lys  Ala  Val  Gly  Trp  Ile  Asp  Gln
-110            -105                 -100

Ala  Thr  Gly  Val  Leu  His  Val  Asn  Val  Thr  Asp  Ala  Ala  Ala  Ser
-95             -90                  -85                           -80

Thr  Val  Arg  Ser  Ala  Gly  Ala  Ser  Ala  Arg  Val  Val  Ser  Ala  Asp  Lys
           -75                  -70                           -65

Ser  Arg  Leu  Ala  Ala  Ser  Glu  Lys  Ala  Ala  Thr  Thr  Val  Ala  Gly  Lys
           -60                  -55                           -50

Asp  Thr  Ile  Ala  Ser  Tyr  Val  Asp  Pro  Val  Thr  Asn  Lys  Val  Ile  Leu
           -45                  -40                           -35

Thr  Val  Pro  Ala  Asp  Arg  Val  Glu  Ala  Thr  Arg  Ala  Lys  Ile  Ala  Asp
           -30                  -25                           -20

Pro  Ser  Val  Thr  Val  Glu  Gly  Thr  Gln  Ala  Lys  Val  Ser  Thr  Gln  Ala
-15             -10                  -5                            -1   1

Asn  Val  Tyr  Gly  Gly  Gln  Gln  Ile  Glu  Phe  Ser  Gly  Tyr  Val  Cys  Ser
            5                    10                           15

Leu  Gly  Phe  Asn  Ala  Thr  Lys  Ala  Gly  Ala  Pro  Val  Phe  Ile  Thr  Ala
           20                   25                           30

Gly  His  Cys  Gly  Glu  Gly  Tyr  Gln  Thr  Phe  Ser  Lys  Asn  Gly  Thr  Thr
35                       40                         45

Leu  Gly  Lys  Thr  Gln  Ala  Phe  Ser  Phe  Pro  Gly  Asn  Asp  Tyr  Ala  Tyr
50                  55                      60                           65

Ser  Thr  Leu  Ala  Ser  Ser  Trp  Thr  Gly  Ile  Gly  Ala  Val  Asp  Leu  Trp
               70                     75                           80

Thr  Gly  Ser  Ala  Arg  Ala  Val  Thr  Gly  Ser  Ser  Asn  Ala  Ala  Val  Gly
               85                     90                           95

Thr  Ala  Ile  Cys  Lys  Ser  Gly  Arg  Thr  Thr  Tyr  Trp  Thr  Cys  Gly  Ser
               100                    105                          110

Val  Gln  Ala  Lys  Asn  Val  Thr  Val  Asn  Tyr  Asp  Asn  Gly  Asp  Gly  Thr
               115                    120                          125

Thr  Ser  Ser  Val  Ser  Gly  Leu  Thr  Lys  Ser  Asn  Thr  Cys  Thr  Glu  Gly
130                      135                    140                         145

Gly  Asp  Ser  Gly  Gly  Ser  Trp  Met  Ala  Gly  Asn  Leu  Ala  Gln  Gly  Val
               150                    155                          160

Thr  Ser  Gly  Gly  Ala  Gly  Tyr  Gly  Ser  Ser  Gly  Val  Cys  Gly  Glu  Lys
               165                    170                          175

Val  Gly  Gln  Pro  Asn  Ile  Ala  Tyr  Phe  Gln  Pro  Val  Gly  Glu  Ile  Leu
               180                    185                          190

Ser  Ala  Tyr  Gly  Leu  Thr  Leu  Lys  Thr  Ala
               195                    200

<210> SEQ ID NO 3
<211> LENGTH: 1203
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1200)
```

```
<220> FEATURE:
<221> NAME/KEY: sig_peptide
<222> LOCATION: (1)..(81)
<220> FEATURE:
<221> NAME/KEY: mat_peptide
<222> LOCATION: (592)..(1200)

<400> SEQUENCE: 3
```

| | | | | | | | | | | | | | | | |
|---|---|---|---|---|---|---|---|---|---|---|---|---|---|---|---|
| atg | aag | aaa | ccg | ttg | ggg | aaa | att | gtc | gca | agc | acc | gca | cta | ctc | 45 |
| Met | Lys | Lys | Pro | Leu | Gly | Lys | Ile | Val | Ala | Ser | Thr | Ala | Leu | Leu | |
| | -195 | | | | -190 | | | | -185 | | | | | | |

| | | | | | | | | | | | | | | | |
|---|---|---|---|---|---|---|---|---|---|---|---|---|---|---|---|
| att | tct | gtt | gct | ttt | agt | tca | tcg | ata | gca | tcg | gct | gca | aat | ccg | 90 |
| Ile | Ser | Val | Ala | Phe | Ser | Ser | Ser | Ile | Ala | Ser | Ala | Ala | Asn | Pro | |
| | -180 | | | | -175 | | | | -170 | | | | | | |

| | | | | | | | | | | | | | | | |
|---|---|---|---|---|---|---|---|---|---|---|---|---|---|---|---|
| gga | ccg | agc | gga | ccg | tca | tca | ccg | tca | aca | gga | ccg | ctg | gca | gtt | 135 |
| Gly | Pro | Ser | Gly | Pro | Ser | Ser | Pro | Ser | Thr | Gly | Pro | Leu | Ala | Val | |
| | -165 | | | | -160 | | | | -155 | | | | | | |

| | | | | | | | | | | | | | | | |
|---|---|---|---|---|---|---|---|---|---|---|---|---|---|---|---|
| gat | tca | ggc | gat | tca | gtt | gca | gaa | atg | tca | gca | caa | tgg | ctg | gca | 180 |
| Asp | Ser | Gly | Asp | Ser | Val | Ala | Glu | Met | Ser | Ala | Gln | Trp | Leu | Ala | |
| | -150 | | | | -145 | | | | -140 | | | | | | |

| | | | | | | | | | | | | | | | |
|---|---|---|---|---|---|---|---|---|---|---|---|---|---|---|---|
| aca | gaa | gaa | ggc | ctg | tca | ctg | gaa | aca | gca | aga | gat | aga | gtt | gca | 225 |
| Thr | Glu | Glu | Gly | Leu | Ser | Leu | Glu | Thr | Ala | Arg | Asp | Arg | Val | Ala | |
| | -135 | | | | -130 | | | | -125 | | | | | | |

| | | | | | | | | | | | | | | | |
|---|---|---|---|---|---|---|---|---|---|---|---|---|---|---|---|
| gca | caa | gaa | gga | ctt | tca | aga | aca | gca | aca | tca | ctt | gaa | aca | agc | 270 |
| Ala | Gln | Glu | Gly | Leu | Ser | Arg | Thr | Ala | Thr | Ser | Leu | Glu | Thr | Ser | |
| | -120 | | | | -115 | | | | -110 | | | | | | |

| | | | | | | | | | | | | | | | |
|---|---|---|---|---|---|---|---|---|---|---|---|---|---|---|---|
| ctt | ggc | gca | aaa | gca | gtt | ggc | aca | tgg | att | gat | caa | gca | aca | ggc | gtt | 318 |
| Leu | Gly | Ala | Lys | Ala | Val | Gly | Thr | Trp | Ile | Asp | Gln | Ala | Thr | Gly | Val |
| | -105 | | | | -100 | | | | -95 | | | | | | |

| | | | | | | | | | | | | | | | |
|---|---|---|---|---|---|---|---|---|---|---|---|---|---|---|---|
| ctg | cat | gtt | aat | gtt | aca | gat | gca | gca | gca | gca | tca | aca | gtt | aga | tca | 366 |
| Leu | His | Val | Asn | Val | Thr | Asp | Ala | Ala | Ala | Ala | Ser | Thr | Val | Arg | Ser |
| | -90 | | | | -85 | | | | -80 | | | | | | |

| | | | | | | | | | | | | | | | |
|---|---|---|---|---|---|---|---|---|---|---|---|---|---|---|---|
| gca | ggc | gca | tca | gca | aga | gtt | gtt | tca | gca | gat | aaa | tca | aga | ctg | gca | 414 |
| Ala | Gly | Ala | Ser | Ala | Arg | Val | Val | Ser | Ala | Asp | Lys | Ser | Arg | Leu | Ala |
| -75 | | | | -70 | | | | -65 | | | | -60 | | | |

| | | | | | | | | | | | | | | | |
|---|---|---|---|---|---|---|---|---|---|---|---|---|---|---|---|
| gca | tca | gaa | aaa | gca | gcg | aca | aca | gtt | gca | ggc | aaa | gat | aca | att | gca | 462 |
| Ala | Ser | Glu | Lys | Ala | Ala | Thr | Thr | Val | Ala | Gly | Lys | Asp | Thr | Ile | Ala |
| | | | -55 | | | | -50 | | | | -45 | | | | |

| | | | | | | | | | | | | | | | |
|---|---|---|---|---|---|---|---|---|---|---|---|---|---|---|---|
| tca | tat | gtt | gat | ccg | gtc | acg | aac | aaa | gtt | att | ctg | aca | gtt | ccg | gca | 510 |
| Ser | Tyr | Val | Asp | Pro | Val | Thr | Asn | Lys | Val | Ile | Leu | Thr | Val | Pro | Ala |
| | -40 | | | | -35 | | | | -30 | | | | | | |

| | | | | | | | | | | | | | | | |
|---|---|---|---|---|---|---|---|---|---|---|---|---|---|---|---|
| gat | aga | gtc | gaa | gca | aca | cgc | gca | aaa | att | gca | gat | ccg | tca | gtt | aca | 558 |
| Asp | Arg | Val | Glu | Ala | Thr | Arg | Ala | Lys | Ile | Ala | Asp | Pro | Ser | Val | Thr |
| | -25 | | | | -20 | | | | -15 | | | | | | |

| | | | | | | | | | | | | | | | |
|---|---|---|---|---|---|---|---|---|---|---|---|---|---|---|---|
| gtt | gaa | ggc | aca | caa | gca | aaa | gtt | tca | aca | caa | gcg | aat | gtt | tat | ggc | 606 |
| Val | Glu | Gly | Thr | Gln | Ala | Lys | Val | Ser | Thr | Gln | Ala | Asn | Val | Tyr | Gly |
| | -10 | | | | -5 | | | | -1 | 1 | | | | 5 | |

| | | | | | | | | | | | | | | | |
|---|---|---|---|---|---|---|---|---|---|---|---|---|---|---|---|
| gga | cag | caa | att | gaa | ttt | agc | ggc | tat | gtt | tgc | tca | ctg | ggc | ttt | aat | 654 |
| Gly | Gln | Gln | Ile | Glu | Phe | Ser | Gly | Tyr | Val | Cys | Ser | Leu | Gly | Phe | Asn |
| | | | 10 | | | | 15 | | | | 20 | | | | |

| | | | | | | | | | | | | | | | |
|---|---|---|---|---|---|---|---|---|---|---|---|---|---|---|---|
| gca | aca | aaa | gca | ggc | gct | ccg | gtc | ttt | att | aca | gca | ggc | cat | tgc | gga | 702 |
| Ala | Thr | Lys | Ala | Gly | Ala | Pro | Val | Phe | Ile | Thr | Ala | Gly | His | Cys | Gly |
| | | 25 | | | | 30 | | | | 35 | | | | | |

| | | | | | | | | | | | | | | | |
|---|---|---|---|---|---|---|---|---|---|---|---|---|---|---|---|
| gaa | ggc | tat | caa | aca | ttt | tca | aaa | aat | ggc | aca | aca | ctg | gga | aaa | aca | 750 |
| Glu | Gly | Tyr | Gln | Thr | Phe | Ser | Lys | Asn | Gly | Thr | Thr | Leu | Gly | Lys | Thr |
| | | 40 | | | | 45 | | | | 50 | | | | | |

| | | | | | | | | | | | | | | | |
|---|---|---|---|---|---|---|---|---|---|---|---|---|---|---|---|
| cag | gca | ttt | tca | ttt | ccg | gga | aac | gat | tat | gca | tat | tca | aca | ctt | gca | 798 |
| Gln | Ala | Phe | Ser | Phe | Pro | Gly | Asn | Asp | Tyr | Ala | Tyr | Ser | Thr | Leu | Ala |
| | | 55 | | | | 60 | | | | 65 | | | | | |

| | | | | | | | | | | | | | | | |
|---|---|---|---|---|---|---|---|---|---|---|---|---|---|---|---|
| tca | agc | tgg | aca | ggc | att | ggc | gca | gtt | gat | ctg | tgg | aca | ggc | tca | gcg | 846 |
| Ser | Ser | Trp | Thr | Gly | Ile | Gly | Ala | Val | Asp | Leu | Trp | Thr | Gly | Ser | Ala |

```
                      70                  75                  80                  85
aga gca gtt aca ggc tca tca aat gca gca gtt gga aca gca att tgc        894
Arg Ala Val Thr Gly Ser Ser Asn Ala Ala Val Gly Thr Ala Ile Cys
                    90                  95                 100 aaa agc ggc aga aca aca tat tgg aca tgc ggc tca gtt caa gca aaa        942
Lys Ser Gly Arg Thr Thr Tyr Trp Thr Cys Gly Ser Val Gln Ala Lys
                   105                 110                 115 aat gtg aca gtc aac tat gat aat ggc gac ggc aca aca tca tca gtt        990
Asn Val Thr Val Asn Tyr Asp Asn Gly Asp Gly Thr Thr Ser Ser Val
                   120                 125                 130 tca ggc ctt aca aaa agc aac aca tgc aca gaa ggc gga gat agc gga       1038
Ser Gly Leu Thr Lys Ser Asn Thr Cys Thr Glu Gly Gly Asp Ser Gly
        135                 140                 145 ggc tca tgg atg gca ggc aat ctg gca caa ggc gtt aca tca ggc gga       1086
Gly Ser Trp Met Ala Gly Asn Leu Ala Gln Gly Val Thr Ser Gly Gly
150                 155                 160                 165 gca gga tat ggc tca tca ggc gtc tgc gga gaa aaa gtt gga caa ccg       1134
Ala Gly Tyr Gly Ser Ser Gly Val Cys Gly Glu Lys Val Gly Gln Pro
                    170                 175                 180 aat att gca tat ttt caa ccg gtc ggc gaa att ctg tca gca tat ggc       1182
Asn Ile Ala Tyr Phe Gln Pro Val Gly Glu Ile Leu Ser Ala Tyr Gly
                185                 190                 195 ctg aca ctt aaa aca gca taa                                           1203
Leu Thr Leu Lys Thr Ala
        200

<210> SEQ ID NO 4
<211> LENGTH: 400
<212> TYPE: PRT
<213> ORGANISM: Artificial Sequence
<220> FEATURE:
<223> OTHER INFORMATION: Synthetic Construct

<400> SEQUENCE: 4

Met Lys Lys Pro Leu Gly Lys Ile Val Ala Ser Thr Ala Leu Leu
        -195                -190                -185

Ile Ser Val Ala Phe Ser Ser Ser Ile Ala Ser Ala Ala Asn Pro
        -180                -175                -170

Gly Pro Ser Gly Pro Ser Ser Pro Ser Thr Gly Pro Leu Ala Val
        -165                -160                -155

Asp Ser Gly Asp Ser Val Ala Glu Met Ser Ala Gln Trp Leu Ala
        -150                -145                -140

Thr Glu Glu Gly Leu Ser Leu Glu Thr Ala Arg Asp Arg Val Ala
        -135                -130                -125

Ala Gln Glu Gly Leu Ser Arg Thr Ala Thr Ser Leu Glu Thr Ser
        -120                -115                -110

Leu Gly Ala Lys Ala Val Gly Thr Trp Ile Asp Gln Ala Thr Gly Val
        -105                -100                 -95

Leu His Val Asn Val Thr Asp Ala Ala Ala Ser Thr Val Arg Ser
         -90                 -85                 -80

Ala Gly Ala Ser Ala Arg Val Val Ser Ala Asp Lys Ser Arg Leu Ala
-75                  -70                 -65                 -60

Ala Ser Glu Lys Ala Ala Thr Val Ala Gly Lys Asp Thr Ile Ala
             -55                 -50                 -45

Ser Tyr Val Asp Pro Val Thr Asn Lys Val Ile Leu Thr Val Pro Ala
             -40                 -35                 -30

Asp Arg Val Glu Ala Thr Arg Ala Lys Ile Ala Asp Pro Ser Val Thr
         -25                 -20                 -15
```

```
Val Glu Gly Thr Gln Ala Lys Val Ser Thr Gln Ala Asn Val Tyr Gly
    -10                 -5                  -1  1                   5

Gly Gln Gln Ile Glu Phe Ser Gly Tyr Val Cys Ser Leu Gly Phe Asn
                 10                  15                  20

Ala Thr Lys Ala Gly Ala Pro Val Phe Ile Thr Ala Gly His Cys Gly
            25                  30                  35

Glu Gly Tyr Gln Thr Phe Ser Lys Asn Gly Thr Leu Gly Lys Thr
            40                  45                  50

Gln Ala Phe Ser Phe Pro Gly Asn Asp Tyr Ala Tyr Ser Thr Leu Ala
    55                  60                  65

Ser Ser Trp Thr Gly Ile Gly Ala Val Asp Leu Trp Thr Gly Ser Ala
70                  75                  80                  85

Arg Ala Val Thr Gly Ser Ser Asn Ala Ala Val Gly Thr Ala Ile Cys
                90                  95                  100

Lys Ser Gly Arg Thr Thr Tyr Trp Thr Cys Gly Ser Val Gln Ala Lys
                105                 110                 115

Asn Val Thr Val Asn Tyr Asp Asn Gly Asp Gly Thr Thr Ser Ser Val
                120                 125                 130

Ser Gly Leu Thr Lys Ser Asn Thr Cys Thr Glu Gly Gly Asp Ser Gly
    135                 140                 145

Gly Ser Trp Met Ala Gly Asn Leu Ala Gln Gly Val Thr Ser Gly Gly
150                 155                 160                 165

Ala Gly Tyr Gly Ser Ser Gly Val Cys Gly Glu Lys Val Gly Gln Pro
                170                 175                 180

Asn Ile Ala Tyr Phe Gln Pro Val Gly Glu Ile Leu Ser Ala Tyr Gly
                185                 190                 195

Leu Thr Leu Lys Thr Ala
            200

<210> SEQ ID NO 5
<211> LENGTH: 203
<212> TYPE: PRT
<213> ORGANISM: Janibacter sp. HTCC2649
<220> FEATURE:
<221> NAME/KEY: mat_polypeptide
<222> LOCATION: (1)..(203)

<400> SEQUENCE: 5

Ala Asn Val Tyr Gly Gly Gln Gln Ile Glu Phe Ser Gly Tyr Val Cys
1               5                   10                  15

Ser Leu Gly Phe Asn Ala Thr Lys Ala Gly Ala Pro Val Phe Ile Thr
            20                  25                  30

Ala Gly His Cys Gly Glu Gly Tyr Gln Thr Phe Ser Lys Asn Gly Thr
        35                  40                  45

Thr Leu Gly Lys Thr Gln Ala Phe Ser Phe Pro Gly Asn Asp Tyr Ala
    50                  55                  60

Tyr Ser Thr Leu Ala Ser Ser Trp Thr Gly Ile Gly Ala Val Asp Leu
65                  70                  75                  80

Trp Thr Gly Ser Ala Arg Ala Val Thr Gly Ser Ser Asn Ala Ala Val
                85                  90                  95

Gly Thr Ala Ile Cys Lys Ser Gly Arg Thr Thr Tyr Trp Thr Cys Gly
                100                 105                 110

Ser Val Gln Ala Lys Asn Val Thr Val Asn Tyr Asp Asn Gly Asp Gly
            115                 120                 125

Thr Thr Ser Ser Val Ser Gly Leu Thr Lys Ser Asn Thr Cys Thr Glu
```

```
                    130               135               140
Gly Gly Asp Ser Gly Gly Ser Trp Met Ala Gly Asn Leu Ala Gln Gly
145                 150               155                 160

Val Thr Ser Gly Gly Ala Gly Tyr Gly Ser Ser Gly Val Cys Gly Glu
                165               170                 175

Lys Val Gly Gln Pro Asn Ile Ala Tyr Phe Gln Pro Val Gly Glu Ile
            180                 185                 190

Leu Ser Ala Tyr Gly Leu Thr Leu Lys Thr Ala
            195                 200

<210> SEQ ID NO 6
<211> LENGTH: 27
<212> TYPE: PRT
<213> ORGANISM: Artificial Sequence
<220> FEATURE:
<223> OTHER INFORMATION: Bacillus clausii secretion signal

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 7
<211> LENGTH: 1596
<212> TYPE: DNA
<213> ORGANISM: Nocardiopsis sp.
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 7
acgtttggta cgggtaccgg tgtccgcatg tggccagaat gccccttgc gacagggaac      60 ggattcggtc ggtagcgcat cgactccgac aaccgcgagg tggccgttcg cgtcgccacg    120
ttctgcgacc gtcatgcgac ccatcatcgg gtgaccccac cgagctctga atggtccacc    180
gttctgacgg tctttccctc accaaaacgt gcacctatgg ttaggacgtt gtttaccgaa    240
tgtctcggtg aacgacaggg gccggacggt attcggcccc gatccccgt tgatccccc    300
```

350
aggagagtag ggacccc atg cga ccc tcc ccc gtt gtc tcc gcc atc ggt
                   Met Arg Pro Ser Pro Val Val Ser Ala Ile Gly
                              -190                    -185 acg gga gcg ctg gcc ttc ggt ctg gcg ctg tcc ggt acc ccg ggt           395
Thr Gly Ala Leu Ala Phe Gly Leu Ala Leu Ser Gly Thr Pro Gly
              -180                 -175                -170 gcc ctc gcg gcc acc gga gcg ctc ccc cag tca ccc acc ccg gag           440
Ala Leu Ala Ala Thr Gly Ala Leu Pro Gln Ser Pro Thr Pro Glu
            -165               -160                -155 gcc gac gcg gtc tcc atg cag gag gcg ctc cag cgc gac ctc gac           485
Ala Asp Ala Val Ser Met Gln Glu Ala Leu Gln Arg Asp Leu Asp
          -150               -145                -140 ctg acc tcc gcc gag gcc gag gag ctg ctg gcc gcc cag gac acc           530
Leu Thr Ser Ala Glu Ala Glu Glu Leu Leu Ala Ala Gln Asp Thr
        -135                -130                -125 gcc ttc gag gtc gac gag gcc gcg gcc gag gcc gcc ggg gac gcc           575
Ala Phe Glu Val Asp Glu Ala Ala Ala Glu Ala Ala Gly Asp Ala

```
                    -120             -115              -110
tac ggc ggc tcc gtc ttc gac acc gag  agc ctg gaa ctg acc gtc ctg      623
Tyr Gly Gly Ser Val Phe Asp Thr Glu  Ser Leu Glu Leu Thr Val Leu
                -105              -100              -95 gtc acc gat gcc gcc gcg gtc gag gcc gtg gag gcc acc ggc gcc ggg      671
Val Thr Asp Ala Ala Ala Val Glu Ala Val Glu Ala Thr Gly Ala Gly
            -90              -85              -80 acc gag ctg gtc tcc tac ggc atc gac ggt ctc gac gag atc gtc cag      719
Thr Glu Leu Val Ser Tyr Gly Ile Asp Gly Leu Asp Glu Ile Val Gln
        -75              -70              -65 gag ctc aac gcc gcc gac gcc gtt ccc ggt gtg gtc ggc tgg tac ccg      767
Glu Leu Asn Ala Ala Asp Ala Val Pro Gly Val Val Gly Trp Tyr Pro
-60              -55              -50                      -45 gac gtg gcg ggt gac acc gtc gtc ctg gag gtc ctg gag ggt tcc gga      815
Asp Val Ala Gly Asp Thr Val Val Leu Glu Val Leu Glu Gly Ser Gly
                -40              -35              -30 gcc gac gtc agc ggc ctg ctc gcg gac gcc ggc gtg gac gcc tcg gcc      863
Ala Asp Val Ser Gly Leu Leu Ala Asp Ala Gly Val Asp Ala Ser Ala
            -25              -20              -15 gtc gag gtg acc acg agc gac cag ccc gag ctc tac gcc gac atc atc      911
Val Glu Val Thr Thr Ser Asp Gln Pro Glu Leu Tyr Ala Asp Ile Ile
        -10              -5               -1  1 ggt ggt ctg gcc tac acc atg ggc ggc cgc tgt tcg gtc ggc ttc gcg      959
Gly Gly Leu Ala Tyr Thr Met Gly Gly Arg Cys Ser Val Gly Phe Ala
5                10               15                       20 gcc acc aac gcc gcc ggt cag ccc ggg ttc gtc acc gcc ggt cac tgc     1007
Ala Thr Asn Ala Ala Gly Gln Pro Gly Phe Val Thr Ala Gly His Cys
                25               30                       35 ggc cgc gtg ggc acc cag gtg acc atc ggc aac ggc agg ggc gtc ttc     1055
Gly Arg Val Gly Thr Gln Val Thr Ile Gly Asn Gly Arg Gly Val Phe
            40               45                       50 gag cag tcc gtc ttc ccc ggc aac gac gcg gcc ttc gtc cgc ggt acg     1103
Glu Gln Ser Val Phe Pro Gly Asn Asp Ala Ala Phe Val Arg Gly Thr
        55               60                       65 tcc aac ttc acg ctg acc aac ctg gtc agc cgc tac aac acc ggc ggg     1151
Ser Asn Phe Thr Leu Thr Asn Leu Val Ser Arg Tyr Asn Thr Gly Gly
    70               75                       80 tac gcc acg gtc gcc ggt cac aac cag gcc ccc atc ggc tcc tcc gtc     1199
Tyr Ala Thr Val Ala Gly His Asn Gln Ala Pro Ile Gly Ser Ser Val
85               90                       95                  100 tgc cgc tcc ggc tcc acc acc ggt tgg cac tgc ggc acc atc cag gcc     1247
Cys Arg Ser Gly Ser Thr Thr Gly Trp His Cys Gly Thr Ile Gln Ala
                105              110                      115 cgc ggc cag tcg gtg agc tac ccc gag ggc acc gtc acc aac atg acc     1295
Arg Gly Gln Ser Val Ser Tyr Pro Glu Gly Thr Val Thr Asn Met Thr
            120              125                      130 cgg acc acc gtg tgc gcc gag ccc ggc gac tcc ggc ggc tcc tac atc     1343
Arg Thr Thr Val Cys Ala Glu Pro Gly Asp Ser Gly Gly Ser Tyr Ile
        135              140                      145 tcc ggc acc cag gcc cag ggc gtg acc tcc ggc ggc tcc ggc aac tgc     1391
Ser Gly Thr Gln Ala Gln Gly Val Thr Ser Gly Gly Ser Gly Asn Cys
    150              155                      160 cgc acc ggc ggg acc acc ttc tac cag gag gtc acc ccc atg gtg aac     1439
Arg Thr Gly Gly Thr Thr Phe Tyr Gln Glu Val Thr Pro Met Val Asn
165              170                      175                  180 tcc tgg ggc gtc cgt ctc cgg acc tgatccccgc ggttccaggc ggaccgacgg    1493
Ser Trp Gly Val Arg Leu Arg Thr
                185 tcgtgacctg agtaccaggc gtccccgccg cttccagcgg cgtccgcacc ggggtgggac   1553
```
cgggcgtggc cacggcccca cccgtgaccg gaccgcccgg cta        1596

<210> SEQ ID NO 8
<211> LENGTH: 382
<212> TYPE: PRT
<213> ORGANISM: Nocardiopsis sp.

<400> SEQUENCE: 8

```
Met Arg Pro Ser Pro  Val Val Ser Ala Ile  Gly Thr Gly Ala Leu
             -190              -185              -180

Ala Phe Gly Leu Ala  Leu Ser Gly Thr Pro  Gly Ala Leu Ala Ala
             -175              -170              -165

Thr Gly Ala Leu Pro  Gln Ser Pro Thr Pro  Glu Ala Asp Ala Val
             -160              -155              -150

Ser Met Gln Glu Ala  Leu Gln Arg Asp Leu  Asp Leu Thr Ser Ala
             -145              -140              -135

Glu Ala Glu Glu Leu  Leu Ala Ala Gln Asp  Thr Ala Phe Glu Val
             -130              -125              -120

Asp Glu Ala Ala Ala  Glu Ala Ala Gly Asp  Ala Tyr Gly Gly Ser
             -115              -110              -105

Val Phe Asp Thr Glu  Ser Leu Glu Leu Thr  Val Leu Val Thr Asp Ala
             -100              -95               -90

Ala Ala Val Glu Ala  Val Glu Ala Thr Gly  Ala Gly Thr Glu Leu Val
             -85               -80               -75

Ser Tyr Gly Ile Asp  Gly Leu Asp Glu Ile  Val Gln Glu Leu Asn Ala
            -70               -65               -60

Ala Asp Ala Val Pro  Gly Val Val Gly Trp  Tyr Pro Asp Val Ala Gly
            -55               -50               -45

Asp Thr Val Val Leu  Glu Val Leu Glu Gly  Ser Gly Ala Asp Val Ser
-40               -35                -30               -25

Gly Leu Leu Ala Asp  Ala Gly Val Asp Ala  Ser Ala Val Glu Val Thr
             -20               -15               -10

Thr Ser Asp Gln Pro  Glu Leu Tyr Ala Asp  Ile Ile Gly Gly Leu Ala
             -5                -1  1              5

Tyr Thr Met Gly Gly  Arg Cys Ser Val Gly  Phe Ala Ala Thr Asn Ala
         10                15                 20

Ala Gly Gln Pro Gly  Phe Val Thr Ala Gly  His Cys Gly Arg Val Gly
25                30                  35                40

Thr Gln Val Thr Ile  Gly Asn Gly Arg Gly  Val Phe Glu Gln Ser Val
             45                50                 55

Phe Pro Gly Asn Asp  Ala Ala Phe Val Arg  Gly Thr Ser Asn Phe Thr
         60                65                  70

Leu Thr Asn Leu Val  Ser Arg Tyr Asn Thr  Gly Gly Tyr Ala Thr Val
         75                80                  85

Ala Gly His Asn Gln  Ala Pro Ile Gly Ser  Ser Val Cys Arg Ser Gly
         90                95                 100

Ser Thr Thr Gly Trp  His Cys Gly Thr Ile  Gln Ala Arg Gly Gln Ser
105               110                 115                120

Val Ser Tyr Pro Glu  Gly Thr Val Thr Asn  Met Thr Arg Thr Thr Val
             125               130                 135

Cys Ala Glu Pro Gly  Asp Ser Gly Gly Ser  Tyr Ile Ser Gly Thr Gln
             140               145                 150

Ala Gln Gly Val Thr  Ser Gly Gly Ser Gly  Asn Cys Arg Thr Gly Gly
             155               160                 165
```

```
Thr Thr Phe Tyr Gln Glu Val Thr Pro Met Val Asn Ser Trp Gly Val
    170                 175                 180

Arg Leu Arg Thr
185

<210> SEQ ID NO 9
<211> LENGTH: 415
<212> TYPE: PRT
<213> ORGANISM: Austwickia chelonae NBRC 105200

<400> SEQUENCE: 9

Met Asn Lys Arg Ile Gly Ala Thr Leu Ala Leu Leu Ser Ser Ala Ala
1               5                   10                  15

Leu Leu Pro Ala Ala Ala Pro Leu Thr Ala Gln Ala Ala Asp Glu Lys
            20                  25                  30

Lys Ser Glu Glu Leu Ser Thr Ile Gln Glu Met Ser Ala Glu Trp Leu
        35                  40                  45

Ser Lys Ser Tyr Gly Leu Asp Gly Glu Glu Ala Lys Arg Arg Val Lys
    50                  55                  60

Asp Gln Asp Gly His Ala Gln Lys Ala Lys Asp Ile Glu Gly Asp Leu
65                  70                  75                  80

Gly Asp Lys Thr Ala Gly Ser Phe Ile Asp Gln Lys Arg Gly Lys Leu
                85                  90                  95

Val Val Thr Val Thr Asp Glu Lys Ala Val Asp Lys Val Lys Glu Lys
            100                 105                 110

Asp Lys Asn Ala Asp Val Arg Val Val Lys Asn Ser Ala Ser Lys Leu
        115                 120                 125

Asn Asp Ser Lys Lys Asn Ala Glu Asp Lys Val Gly Asp Lys Met Ala
    130                 135                 140

Ala Ser Tyr Val Asp Val Glu Arg Asn Val Val Val Leu Thr Val Pro
145                 150                 155                 160

Lys Asp Lys Ala Glu Glu Ala Lys Lys Gln Val Lys Asp Val Gln Gly
                165                 170                 175

Val Glu Val Gln Glu Val Glu Ala Thr Ile Glu Ala Gln Ala Asn Leu
            180                 185                 190

Tyr Gly Gly Gln Glu Ile Gln Phe Gly Arg Ser Val Cys Ser Val Gly
        195                 200                 205

Phe Pro Ala Thr Lys Asp Gly Lys Asn Val Phe Ile Thr Ala Gly His
    210                 215                 220

Cys Ala Ala Gly Gly Gln Ala Phe Arg Arg Asn Gly Gln Asn Leu Gly
225                 230                 235                 240

Lys Pro Val Lys Tyr Asn Phe Pro Gly Pro Asp Met Ala Tyr Ser Thr
                245                 250                 255

Met Glu Asn Gly Trp Asn Gly Val Gly Ala Val Asp His Trp Asn Gly
            260                 265                 270

Lys Ala Val Ala Val Ala Gly Ser Gln Glu Ala Pro Val Gly Ala Thr
        275                 280                 285

Val Cys Lys Ser Gly Arg Thr Thr Arg Trp Thr Cys Gly Val Ile Gln
    290                 295                 300

Ala Lys Asn Val Thr Val Arg Tyr Gly Lys Pro Gly Gly Gly Gln Asp
305                 310                 315                 320

Ile Val Arg Gly Met Thr Gln Ala Asn Val Cys Ser Glu Gly Gly Asp
                325                 330                 335

Ser Gly Gly Ser Trp Ile Ala Gly Asn Gln Ala Gln Gly Val Thr Ser
```

```
                340               345               350
Gly Gly Ala Gly Tyr Gly Pro Asn Lys Ser Cys Gly Glu Lys Val Gly
            355                 360                 365

Arg Pro Asn Val Ala Tyr Phe Gln Pro Leu Asn Pro Ile Leu Lys Asp
        370                 375                 380

Tyr Gly Leu Lys Leu Thr Thr His Asn Gly Lys Gly Gly Gly Asp
385                 390                 395                 400

Asn Gly Gly Asp Arg Asn Arg Asp Asn Arg Lys Gly Gly Arg Tyr
                405                 410                 415

<210> SEQ ID NO 10
<211> LENGTH: 1203
<212> TYPE: DNA
<213> ORGANISM: Terracoccus sp.
<220> FEATURE:
<221> NAME/KEY: CDS
<222> LOCATION: (1)..(1200)
<220> FEATURE:
<221> NAME/KEY: sig_peptide
<222> LOCATION: (1)..(78)
<220> FEATURE:
<221> NAME/KEY: mat_peptide
<222> LOCATION: (589)..(1200)

<400> SEQUENCE: 10 atg atc cgc acc agt ctc acc acc ctg gcc gcc acg gcc gcg atc         45
Met Ile Arg Thr Ser Leu Thr Thr Leu Ala Ala Thr Ala Ala Ile
    -195                -190                -185 gcc acc gcg atc acc gtg atg ccg gcc cag gca tcg acc ctc gcg         90
Ala Thr Ala Ile Thr Val Met Pro Ala Gln Ala Ser Thr Leu Ala
        -180                -175                -170 tcc gac ccg acc ccc gcg ccg acg cca gcg gcg tcc acc gac tca        135
Ser Asp Pro Thr Pro Ala Pro Thr Pro Ala Ala Ser Thr Asp Ser
    -165                -160                -155 ggc cag tcc gtc gcc gag atg tcg gcg cgc tgg ctc gcg aag gac        180
Gly Gln Ser Val Ala Glu Met Ser Ala Arg Trp Leu Ala Lys Asp
        -150                -145                -140 cgt gcc atc agc ctc gcc acg gct cgc cag cgc gtc gcg gcc cag        225
Arg Ala Ile Ser Leu Ala Thr Ala Arg Gln Arg Val Ala Ala Gln
    -135                -130                -125 gac gga cag acc cgc acg gcg gcc tcg ctc gag cgc gcg ctc ggc        270
Asp Gly Gln Thr Arg Thr Ala Ala Ser Leu Glu Arg Ala Leu Gly
    -120                -115                -110 gcc cgg gcc gca ggg tcc tac atc gac gcc acc tcc ggc gcg ctc gtc    318
Ala Arg Ala Ala Gly Ser Tyr Ile Asp Ala Thr Ser Gly Ala Leu Val
    -105                -100                -95 gtc aac gtc gtc gac acc gcg tcc gtc gcc agg gtg ctg tct gcc ggt    366
Val Asn Val Val Asp Thr Ala Ser Val Ala Arg Val Leu Ser Ala Gly
-90                 -85                 -80                 -75 gcc gtc gcc aag gtc gtc gac cgc tcg acg agc gag ctg tcc gcg acc    414
Ala Val Ala Lys Val Val Asp Arg Ser Thr Ser Glu Leu Ser Ala Thr
                -70                 -65                 -60 gag cgc gcg gca cgc gca cgt gcc ggg tcg gcc gtc gtg tcc tcc tac    462
Glu Arg Ala Ala Arg Ala Arg Ala Gly Ser Ala Val Val Ser Ser Tyr
        -55                 -50                 -45 acc gac ccc gtc acc aac ggc gtc gtc ctg acc gtc ccc agc gcg cgg    510
Thr Asp Pro Val Thr Asn Gly Val Val Leu Thr Val Pro Ser Ala Arg
            -40                 -35                 -30 gtc tcg gag gtc cgc agc gag gtc gtt ggt ctc gac ggg gtg acc gtc    558
Val Ser Glu Val Arg Ser Glu Val Val Gly Leu Asp Gly Val Thr Val
        -25                 -20                 -15
```

| | | | | | | | | | | | | | | | | |
|---|---|---|---|---|---|---|---|---|---|---|---|---|---|---|---|---|
| gca | ggc | acc | gac | gca | cgg | acg | acg | acg | cag | gcc | aac | gtc | tac | ggc | ggc | 606 |
| Ala | Gly | Thr | Asp | Ala | Arg | Thr | Thr | Thr | Gln | Ala | Asn | Val | Tyr | Gly | Gly | |
| -10 | | | | -5 | | | | | -1 | 1 | | | | 5 | | |
| cag | cag | atc | gag | ttc | agc | ggc | tac | gtc | tgc | tcg | ctc | ggc | ttc | aac | gcc | 654 |
| Gln | Gln | Ile | Glu | Phe | Ser | Gly | Tyr | Val | Cys | Ser | Leu | Gly | Phe | Asn | Ala | |
| | | | 10 | | | | | 15 | | | | | 20 | | | |
| acc | cgc | ggc | ggt | gct | ccg | gtg | ttc | gtc | acc | gcc | ggc | cac | tgt | ggt | gag | 702 |
| Thr | Arg | Gly | Gly | Ala | Pro | Val | Phe | Val | Thr | Ala | Gly | His | Cys | Gly | Glu | |
| | | 25 | | | | | 30 | | | | | 35 | | | | |
| ggt | tac | cag | acc | ttc | agc | aag | gga | ggc | acg | acg | ctg | ggg | tcg | acg | cag | 750 |
| Gly | Tyr | Gln | Thr | Phe | Ser | Lys | Gly | Gly | Thr | Thr | Leu | Gly | Ser | Thr | Gln | |
| 40 | | | | | 45 | | | | | 50 | | | | | | |
| gcg | tac | tcc | ttc | ccg | ggc | aac | gac | tac | gcc | tac | tcg | acc | ctg | acg | tcg | 798 |
| Ala | Tyr | Ser | Phe | Pro | Gly | Asn | Asp | Tyr | Ala | Tyr | Ser | Thr | Leu | Thr | Ser | |
| 55 | | | | | 60 | | | | | 65 | | | | | 70 | |
| agc | tgg | acc | ggg | gtc | ggt | gcc | gtc | gac | ctc | tac | gac | ggc | gtc | aac | gcc | 846 |
| Ser | Trp | Thr | Gly | Val | Gly | Ala | Val | Asp | Leu | Tyr | Asp | Gly | Val | Asn | Ala | |
| | | | | 75 | | | | | 80 | | | | | 85 | | |
| cgc | cgg | gtc | tcg | ggc | tac | tcg | aac | gcc | ccg | gtc | ggg | acc | gcg | atc | tgc | 894 |
| Arg | Arg | Val | Ser | Gly | Tyr | Ser | Asn | Ala | Pro | Val | Gly | Thr | Ala | Ile | Cys | |
| | | | 90 | | | | | 95 | | | | | 100 | | | |
| aag | tcg | ggc | cgc | acg | acc | ggc | tgg | acc | tgc | ggc | tcg | gtg | cag | gcc | aag | 942 |
| Lys | Ser | Gly | Arg | Thr | Thr | Gly | Trp | Thr | Cys | Gly | Ser | Val | Gln | Ala | Lys | |
| | | 105 | | | | | 110 | | | | | 115 | | | | |
| aac | gtc | acc | gtc | aac | tac | agc | aac | gcc | gac | ggc | tcg | acg | agc | acc | gtg | 990 |
| Asn | Val | Thr | Val | Asn | Tyr | Ser | Asn | Ala | Asp | Gly | Ser | Thr | Ser | Thr | Val | |
| | 120 | | | | | 125 | | | | | 130 | | | | | |
| agc | ggc | ctg | acg | aag | agc | aac | acc | tgc | acc | gag | ggt | ggc | gac | tcg | ggc | 1038 |
| Ser | Gly | Leu | Thr | Lys | Ser | Asn | Thr | Cys | Thr | Glu | Gly | Gly | Asp | Ser | Gly | |
| 135 | | | | | 140 | | | | | 145 | | | | | 150 | |
| ggc | tcg | tgg | atg | gcg | agc | acg | tcg | gca | cag | ggc | gtg | acg | agc | ggt | ggt | 1086 |
| Gly | Ser | Trp | Met | Ala | Ser | Thr | Ser | Ala | Gln | Gly | Val | Thr | Ser | Gly | Gly | |
| | | | | 155 | | | | | 160 | | | | | 165 | | |
| gcc | ggc | tac | ggc | gcc | aac | agc | gtc | tgc | ggc | cag | aag | gtc | ggc | cag | ccc | 1134 |
| Ala | Gly | Tyr | Gly | Ala | Asn | Ser | Val | Cys | Gly | Gln | Lys | Val | Gly | Gln | Pro | |
| | | 170 | | | | | 175 | | | | | 180 | | | | |
| aac | atc | gcc | tac | ttc | cag | ccc | gtc | gac | gag | atc | gtg | tcg | gcc | tac | ggc | 1182 |
| Asn | Ile | Ala | Tyr | Phe | Gln | Pro | Val | Asp | Glu | Ile | Val | Ser | Ala | Tyr | Gly | |
| | 185 | | | | | 190 | | | | | 195 | | | | | |
| ctg | acg | ctc | aag | acc | tcc | tga | | | | | | | | | | 1203 |
| Leu | Thr | Leu | Lys | Thr | Ser | | | | | | | | | | | |
| | 200 | | | | | | | | | | | | | | | |

<210> SEQ ID NO 11
<211> LENGTH: 400
<212> TYPE: PRT
<213> ORGANISM: Terracoccus sp.

<400> SEQUENCE: 11

Met Ile Arg Thr Ser Leu Thr Leu Ala Ala Thr Ala Ala Ile
    -195            -190                -185

Ala Thr Ala Ile Thr Val Met Pro Ala Gln Ala Ser Thr Leu Ala
    -180            -175                -170

Ser Asp Pro Thr Pro Ala Pro Thr Pro Ala Ala Ser Thr Asp Ser
    -165            -160                -155

Gly Gln Ser Val Ala Glu Met Ser Ala Arg Trp Leu Ala Lys Asp
    -150            -145                -140

Arg Ala Ile Ser Leu Ala Thr Ala Arg Gln Arg Val Ala Ala Gln
    -135            -130                -125

Asp Gly Gln Thr Arg Thr Ala Ala Ser Leu Glu Arg Ala Leu Gly
    -120                -115                -110

Ala Arg Ala Ala Gly Ser Tyr Ile Asp Ala Thr Ser Gly Ala Leu Val
    -105                -100                -95

Val Asn Val Val Asp Thr Ala Ser Val Ala Arg Val Leu Ser Ala Gly
-90              -85                  -80                  -75

Ala Val Ala Lys Val Val Asp Arg Ser Thr Ser Glu Leu Ser Ala Thr
                -70                  -65                  -60

Glu Arg Ala Ala Arg Ala Arg Ala Gly Ser Ala Val Val Ser Ser Tyr
            -55                  -50                  -45

Thr Asp Pro Val Thr Asn Gly Val Val Leu Thr Val Pro Ser Ala Arg
        -40                  -35                  -30

Val Ser Glu Val Arg Ser Glu Val Val Gly Leu Asp Gly Val Thr Val
    -25                  -20                  -15

Ala Gly Thr Asp Ala Arg Thr Thr Thr Gln Ala Asn Val Tyr Gly Gly
-10              -5                   -1    1                5

Gln Gln Ile Glu Phe Ser Gly Tyr Val Cys Ser Leu Gly Phe Asn Ala
            10                  15                  20

Thr Arg Gly Gly Ala Pro Val Phe Val Thr Ala Gly His Cys Gly Glu
        25                  30                  35

Gly Tyr Gln Thr Phe Ser Lys Gly Gly Thr Thr Leu Gly Ser Thr Gln
    40                  45                  50

Ala Tyr Ser Phe Pro Gly Asn Asp Tyr Ala Tyr Ser Thr Leu Thr Ser
55                  60                  65                  70

Ser Trp Thr Gly Val Gly Ala Val Asp Leu Tyr Asp Gly Val Asn Ala
                75                  80                  85

Arg Arg Val Ser Gly Tyr Ser Asn Ala Pro Val Gly Thr Ala Ile Cys
            90                  95                  100

Lys Ser Gly Arg Thr Thr Gly Trp Thr Cys Gly Ser Val Gln Ala Lys
        105                 110                 115

Asn Val Thr Val Asn Tyr Ser Asn Ala Asp Gly Ser Ser Thr Thr Val
        120                 125                 130

Ser Gly Leu Thr Lys Ser Asn Thr Cys Thr Glu Gly Gly Asp Ser Gly
135                 140                 145                 150

Gly Ser Trp Met Ala Ser Thr Ala Gln Gly Val Thr Ser Gly Gly
                155                 160                 165

Ala Gly Tyr Gly Ala Asn Ser Val Cys Gly Gln Lys Val Gly Gln Pro
            170                 175                 180

Asn Ile Ala Tyr Phe Gln Pro Val Asp Glu Ile Val Ser Ala Tyr Gly
        185                 190                 195

Leu Thr Leu Lys Thr Ser
    200

<210> SEQ ID NO 12
<211> LENGTH: 1206
<212> TYPE: DNA
<213> ORGANISM: Artificial Sequence
<220> FEATURE:
<223> OTHER INFORMATION: Expression construct
<220> FEATURE:
<221> NAME/KEY: CDS
<222> LOCATION: (1)..(1203)
<220> FEATURE:
<221> NAME/KEY: sig_peptide
<222> LOCATION: (1)..(81)
<220> FEATURE:
<221> NAME/KEY: mat_peptide
<222> LOCATION: (592)..(1203)

<400> SEQUENCE: 12

```
atg aag aaa ccg ttg ggg aaa att gtc gca agc acc gca cta ctc      45
Met Lys Lys Pro Leu Gly Lys Ile Val Ala Ser Thr Ala Leu Leu
    -195                 -190                -185 att tct gtt gct ttt agt tca tcg atc gca tcg gct tca aca ctg      90
Ile Ser Val Ala Phe Ser Ser Ser Ile Ala Ser Ala Ser Thr Leu
        -180                -175                -170 gca tca gat ccg aca ccg gca cct aca ccg gca gca agc aca gat     135
Ala Ser Asp Pro Thr Pro Ala Pro Thr Pro Ala Ala Ser Thr Asp
    -165                -160                 -155 tca ggc caa tca gtt gca gaa atg tca gca aga tgg ctg gca aaa     180
Ser Gly Gln Ser Val Ala Glu Met Ser Ala Arg Trp Leu Ala Lys
    -150                -145                 -140 gat aga gca att tca ctg gca aca gca aga cag cgc gtt gca gca     225
Asp Arg Ala Ile Ser Leu Ala Thr Ala Arg Gln Arg Val Ala Ala
    -135                -130                 -125 caa gat ggc caa aca aga aca gca gca tca ctg gaa aga gca ctt     270
Gln Asp Gly Gln Thr Arg Thr Ala Ala Ser Leu Glu Arg Ala Leu
    -120                -115                 -110 ggc gca aga gca gca ggc tca tat att gat gca aca tca ggc gca ctg 318
Gly Ala Arg Ala Ala Gly Ser Tyr Ile Asp Ala Thr Ser Gly Ala Leu
    -105                -100                 -95 gtt gtt aat gtt gtt gat aca gca agc gtt gca aga gtt ctg tca gca 366
Val Val Asn Val Val Asp Thr Ala Ser Val Ala Arg Val Leu Ser Ala
    -90                 -85                  -80 ggc gca gtt gca aaa gtt gtc gat aga tca aca tca gaa ctg agc gca 414
Gly Ala Val Ala Lys Val Val Asp Arg Ser Thr Ser Glu Leu Ser Ala
-75                 -70                  -65                  -60 aca gaa aga gcg gca aga gcg aga gca ggc agc gca gtt gtt tca tca 462
Thr Glu Arg Ala Ala Arg Ala Arg Ala Gly Ser Ala Val Val Ser Ser
                    -55                  -50                  -45 tat aca gat ccg gtt aca aat ggc gtt gtt ctg aca gtt ccg agc gca 510
Tyr Thr Asp Pro Val Thr Asn Gly Val Val Leu Thr Val Pro Ser Ala
                    -40                  -35                  -30 aga gtt tca gaa gtt aga agc gaa gtt gtt ggc ctg gat ggc gtt aca 558
Arg Val Ser Glu Val Arg Ser Glu Val Val Gly Leu Asp Gly Val Thr
            -25                  -20                  -15 gtt gca ggc aca gat gca aga aca aca aca caa gca aat gtt tat ggc 606
Val Ala Gly Thr Asp Ala Arg Thr Thr Thr Gln Ala Asn Val Tyr Gly
-10                  -5                   -1  1                5 gga cag cag att gaa ttt tca ggc tat gtt tgc tca ctg ggc ttt aat 654
Gly Gln Gln Ile Glu Phe Ser Gly Tyr Val Cys Ser Leu Gly Phe Asn
                    10                   15                   20 gca aca aga ggc gga gca ccg gtt ttt gtt aca gca ggc cat tgc gga 702
Ala Thr Arg Gly Gly Ala Pro Val Phe Val Thr Ala Gly His Cys Gly
                    25                   30                   35 gaa ggc tat caa aca ttt tca aaa ggc gga aca aca ctg ggc agc aca 750
Glu Gly Tyr Gln Thr Phe Ser Lys Gly Gly Thr Thr Leu Gly Ser Thr
                    40                   45                   50 caa gca tat tca ttt ccg gga aac gat tat gca tat agc aca ctg aca 798
Gln Ala Tyr Ser Phe Pro Gly Asn Asp Tyr Ala Tyr Ser Thr Leu Thr
                    55                   60                   65 tca tca tgg aca ggc gtt gga gca gtt gat ctg tat gat ggc gtc aat 846
Ser Ser Trp Thr Gly Val Gly Ala Val Asp Leu Tyr Asp Gly Val Asn
70                   75                   80                   85 gca aga aga gtt agc ggc tat tca aat gca ccg gtt ggc aca gca att 894
Ala Arg Arg Val Ser Gly Tyr Ser Asn Ala Pro Val Gly Thr Ala Ile
                    90                   95                   100
```

```
tgc aaa agc ggc aga aca aca ggc tgg aca tgc ggc tca gtt caa gca      942
Cys Lys Ser Gly Arg Thr Thr Gly Trp Thr Cys Gly Ser Val Gln Ala
        105                 110                 115 aaa aat gtc aca gtc aat tat agc aat gca gat ggc tca aca tca aca      990
Lys Asn Val Thr Val Asn Tyr Ser Asn Ala Asp Gly Ser Thr Ser Thr
        120                 125                 130 gtt tca ggc ctt aca aaa agc aac aca tgc aca gaa ggc gga gat agc     1038
Val Ser Gly Leu Thr Lys Ser Asn Thr Cys Thr Glu Gly Gly Asp Ser
        135                 140                 145 gga ggc tca tgg atg gca tca aca agc gca caa ggc gtt aca agc gga     1086
Gly Gly Ser Trp Met Ala Ser Thr Ser Ala Gln Gly Val Thr Ser Gly
150                 155                 160                 165 ggc gca ggc tat ggc gca aat tca gtt tgc gga caa aaa gtt gga caa     1134
Gly Ala Gly Tyr Gly Ala Asn Ser Val Cys Gly Gln Lys Val Gly Gln
                170                 175                 180 ccg aac att gca tat ttt caa ccg gtc gat gaa att gtt agc gca tat     1182
Pro Asn Ile Ala Tyr Phe Gln Pro Val Asp Glu Ile Val Ser Ala Tyr
            185                 190                 195 ggc ctg aca ctg aaa aca tca taa                                     1206
Gly Leu Thr Leu Lys Thr Ser
        200

<210> SEQ ID NO 13
<211> LENGTH: 401
<212> TYPE: PRT
<213> ORGANISM: Artificial Sequence
<220> FEATURE:
<223> OTHER INFORMATION: Synthetic Construct

<400> SEQUENCE: 13

Met Lys Lys Pro Leu Gly Lys Ile Val Ala Ser Thr Ala Leu Leu
        -195                -190                -185

Ile Ser Val Ala Phe Ser Ser Ser Ile Ala Ser Ala Ser Thr Leu
        -180                -175                -170

Ala Ser Asp Pro Thr Pro Ala Pro Thr Pro Ala Ala Ser Thr Asp
        -165                -160                -155

Ser Gly Gln Ser Val Ala Glu Met Ser Ala Arg Trp Leu Ala Lys
        -150                -145                -140

Asp Arg Ala Ile Ser Leu Ala Thr Ala Arg Gln Arg Val Ala Ala
        -135                -130                -125

Gln Asp Gly Gln Thr Arg Thr Ala Ala Ser Leu Glu Arg Ala Leu
        -120                -115                -110

Gly Ala Arg Ala Ala Gly Ser Tyr Ile Asp Ala Thr Ser Gly Ala Leu
        -105                -100                -95

Val Val Asn Val Val Asp Thr Ala Ser Val Ala Arg Val Leu Ser Ala
        -90                 -85                 -80

Gly Ala Val Ala Lys Val Asp Arg Ser Thr Ser Glu Leu Ser Ala
-75                 -70                 -65                 -60

Thr Glu Arg Ala Ala Arg Ala Arg Ala Gly Ser Ala Val Val Ser Ser
                -55                 -50                 -45

Tyr Thr Asp Pro Val Thr Asn Gly Val Val Leu Thr Val Pro Ser Ala
            -40                 -35                 -30

Arg Val Ser Glu Val Arg Ser Glu Val Val Gly Leu Asp Gly Val Thr
        -25                 -20                 -15

Val Ala Gly Thr Asp Ala Arg Thr Thr Thr Gln Ala Asn Val Tyr Gly
        -10                 -5          -1  1                   5

Gly Gln Gln Ile Glu Phe Ser Gly Tyr Val Cys Ser Leu Gly Phe Asn
                10                  15                  20
```

Ala Thr Arg Gly Gly Ala Pro Val Phe Val Thr Ala Gly His Cys Gly
            25                  30                  35

Glu Gly Tyr Gln Thr Phe Ser Lys Gly Gly Thr Thr Leu Gly Ser Thr
        40                  45                  50

Gln Ala Tyr Ser Phe Pro Gly Asn Asp Tyr Ala Tyr Ser Thr Leu Thr
    55                  60                  65

Ser Ser Trp Thr Gly Val Gly Ala Val Asp Leu Tyr Asp Gly Val Asn
70                  75                  80                  85

Ala Arg Arg Val Ser Gly Tyr Ser Asn Ala Pro Val Gly Thr Ala Ile
                90                  95                  100

Cys Lys Ser Gly Arg Thr Thr Gly Trp Thr Cys Gly Ser Val Gln Ala
            105                 110                 115

Lys Asn Val Thr Val Asn Tyr Ser Asn Ala Asp Gly Ser Thr Ser Thr
        120                 125                 130

Val Ser Gly Leu Thr Lys Ser Asn Thr Cys Thr Glu Gly Gly Asp Ser
    135                 140                 145

Gly Gly Ser Trp Met Ala Ser Thr Ser Ala Gln Gly Val Thr Ser Gly
150                 155                 160                 165

Gly Ala Gly Tyr Gly Ala Asn Ser Val Cys Gly Gln Lys Val Gly Gln
                170                 175                 180

Pro Asn Ile Ala Tyr Phe Gln Pro Val Asp Glu Ile Val Ser Ala Tyr
            185                 190                 195

Gly Leu Thr Leu Lys Thr Ser
            200

<210> SEQ ID NO 14
<211> LENGTH: 204
<212> TYPE: PRT
<213> ORGANISM: Terracoccus sp.
<220> FEATURE:
<221> NAME/KEY: mat_peptide
<222> LOCATION: (1)..(204)

<400> SEQUENCE: 14

Ala Asn Val Tyr Gly Gly Gln Gln Ile Glu Phe Ser Gly Tyr Val Cys
1               5                   10                  15

Ser Leu Gly Phe Asn Ala Thr Arg Gly Gly Ala Pro Val Phe Val Thr
            20                  25                  30

Ala Gly His Cys Gly Glu Gly Tyr Gln Thr Phe Ser Lys Gly Gly Thr
        35                  40                  45

Thr Leu Gly Ser Thr Gln Ala Tyr Ser Phe Pro Gly Asn Asp Tyr Ala
    50                  55                  60

Tyr Ser Thr Leu Thr Ser Ser Trp Thr Gly Val Gly Ala Val Asp Leu
65                  70                  75                  80

Tyr Asp Gly Val Asn Ala Arg Arg Val Ser Gly Tyr Ser Asn Ala Pro
                85                  90                  95

Val Gly Thr Ala Ile Cys Lys Ser Gly Arg Thr Thr Gly Trp Thr Cys
            100                 105                 110

Gly Ser Val Gln Ala Lys Asn Val Thr Val Asn Tyr Ser Asn Ala Asp
        115                 120                 125

Gly Ser Thr Ser Thr Val Ser Gly Leu Thr Lys Ser Asn Thr Cys Thr
    130                 135                 140

Glu Gly Gly Asp Ser Gly Gly Ser Trp Met Ala Ser Thr Ser Ala Gln
145                 150                 155                 160

Gly Val Thr Ser Gly Gly Ala Gly Tyr Gly Ala Asn Ser Val Cys Gly

```
                      165                 170                 175
Gln Lys Val Gly Gln Pro Asn Ile Ala Tyr Phe Gln Pro Val Asp Glu
                180                 185                 190

Ile Val Ser Ala Tyr Gly Leu Thr Leu Lys Thr Ser
        195                 200

<210> SEQ ID NO 15
<211> LENGTH: 9
<212> TYPE: PRT
<213> ORGANISM: Artificial Sequence
<220> FEATURE:
<223> OTHER INFORMATION: Motif VCG[E/Q]KVGQP.
<220> FEATURE:
<221> NAME/KEY: MISC_FEATURE
<222> LOCATION: (4)..(4)
<223> OTHER INFORMATION: The amino acid in position 4 of the conserved
      motif is either glutamic acid (Glu, E) or Glutamine (Gln, Q).

<400> SEQUENCE: 15

Val Cys Gly Xaa Lys Val Gly Gln Pro
1               5

<210> SEQ ID NO 16
<211> LENGTH: 1209
<212> TYPE: DNA
<213> ORGANISM: Knoellia flava
<220> FEATURE:
<221> NAME/KEY: CDS
<222> LOCATION: (1)..(1206)
<220> FEATURE:
<221> NAME/KEY: sig_peptide
<222> LOCATION: (1)..(87)
<220> FEATURE:
<221> NAME/KEY: mat_peptide
<222> LOCATION: (595)..(1206)

<400> SEQUENCE: 16
```

| | | | | | | | | | | | | | | | |
|---|---|---|---|---|---|---|---|---|---|---|---|---|---|---|---|
| atg | tct | cgc | aga | cgt | ctc | acc | gtc | ctc | gcc | ggg | ggc | ctc | tcg | gcc | 45 |
| Met | Ser | Arg | Arg | Arg | Leu | Thr | Val | Leu | Ala | Gly | Gly | Leu | Ser | Ala | |
| | | | -195 | | | | -190 | | | | -185 | | | | |
| gcg | gcg | gca | gcc | acc | gcc | ctc | tgc | gtc | gcg | ccc | gcg | tcc | gcc | gcc | 90 |
| Ala | Ala | Ala | Ala | Thr | Ala | Leu | Cys | Val | Ala | Pro | Ala | Ser | Ala | Ala | |
| | | | -180 | | | | -175 | | | | -170 | | | | |
| acc | tcc | gcg | gcg | ggc | ggt | ccg | gag | ccg | agc | acc | ggc | cct | ctc | gcc | 135 |
| Thr | Ser | Ala | Ala | Gly | Gly | Pro | Glu | Pro | Ser | Thr | Gly | Pro | Leu | Ala | |
| | | | -165 | | | | -160 | | | | -155 | | | | |
| acc | gac | tcg | ggc | gcg | tcc | gtc | gcc | gag | atg | tcg | gcc | cgg | tgg | ctc | 180 |
| Thr | Asp | Ser | Gly | Ala | Ser | Val | Ala | Glu | Met | Ser | Ala | Arg | Trp | Leu | |
| | | | -150 | | | | -145 | | | | -140 | | | | |
| gcc | aag | gag | cac | gac | ctg | agc | atc | gag | acc | gct | cgt | gag | cgg | atc | 225 |
| Ala | Lys | Glu | His | Asp | Leu | Ser | Ile | Glu | Thr | Ala | Arg | Glu | Arg | Ile | |
| | | | -135 | | | | -130 | | | | -125 | | | | |
| gcg | tcc | cag | gag | gac | aag | agt | cgc | aag | gcc | gag | gct | ctc | gaa | cgg | 270 |
| Ala | Ser | Gln | Glu | Asp | Lys | Ser | Arg | Lys | Ala | Glu | Ala | Leu | Glu | Arg | |
| | | | -120 | | | | -115 | | | | -110 | | | | |
| tcg | ctc | ggc | gcg | cga | gcc | gtg | ggc | tcg | ttc | atc | gac | cag | acc | ggc | 318 |
| Ser | Leu | Gly | Ala | Arg | Ala | Val | Gly | Ser | Phe | Ile | Asp | Gln | Thr | Gly | Gly |
| | | | -105 | | | | -100 | | | | -95 | | | | |
| gtg | ctc | gtc | gtc | aac | gtc | acc | gac | gcc | gac | gcc | gct | gcc | cgc | gtg | cag | 366 |
| Val | Leu | Val | Val | Asn | Val | Thr | Asp | Ala | Asp | Ala | Ala | Ala | Arg | Val | Gln |
| | | | -90 | | | | -85 | | | | -80 | | | | |
| aag | gcg | ggc | gcg | acc | gcc | cgc | gtc | gtc | acc | gag | gac | aag | gcg | gag | ctc | 414 |
| Lys | Ala | Gly | Ala | Thr | Ala | Arg | Val | Val | Thr | Glu | Asp | Lys | Ala | Glu | Leu |
| | | | -75 | | | | -70 | | | | -65 | | | | |

| | | | | | | | | | | | | | | | |
|---|---|---|---|---|---|---|---|---|---|---|---|---|---|---|---|
| ggc | gcg | tcg | cag | gcg | agg | gcg | gtc | aag | gcg | ctc | ggc | gcc | acg | gtc | atc | 462 |
| Gly | Ala | Ser | Gln | Ala | Arg | Ala | Val | Lys | Ala | Leu | Gly | Ala | Thr | Val | Ile |
| -60 | | | | -55 | | | | | -50 | | | | | -45 | |

| | | | | | | | | | | | | | | | |
|---|---|---|---|---|---|---|---|---|---|---|---|---|---|---|---|
| gac | agc | tcc | gtc | gac | ccg | gtg | acc | aac | aag | gtc | gtc | gtc | acc | gtg | ccc | 510 |
| Asp | Ser | Ser | Val | Asp | Pro | Val | Thr | Asn | Lys | Val | Val | Val | Thr | Val | Pro |
| | | | -40 | | | | | -35 | | | | | -30 | | |

| | | | | | | | | | | | | | | | |
|---|---|---|---|---|---|---|---|---|---|---|---|---|---|---|---|
| acc | gcc | gac | gtc | gcc | gcc | gcg | cgg | gcg | cgc | acg | agc | gac | ccg | tcg | gtg | 558 |
| Thr | Ala | Asp | Val | Ala | Ala | Ala | Arg | Ala | Arg | Thr | Ser | Asp | Pro | Ser | Val |
| | | | -25 | | | | | -20 | | | | | -15 | | |

| | | | | | | | | | | | | | | | |
|---|---|---|---|---|---|---|---|---|---|---|---|---|---|---|---|
| acg | atc | cag | ggc | acc | gac | gcg | acg | gtg | tcg | acg | cag | gcc | aac | gtc | tat | 606 |
| Thr | Ile | Gln | Gly | Thr | Asp | Ala | Thr | Val | Ser | Thr | Gln | Ala | Asn | Val | Tyr |
| | | -10 | | | | | -5 | | | | | -1 | 1 | | |

| | | | | | | | | | | | | | | | |
|---|---|---|---|---|---|---|---|---|---|---|---|---|---|---|---|
| ggc | ggg | cag | cag | atc | gag | ttc | agc | ggc | tac | gtc | tgc | tcg | ctg | ggc | ttc | 654 |
| Gly | Gly | Gln | Gln | Ile | Glu | Phe | Ser | Gly | Tyr | Val | Cys | Ser | Leu | Gly | Phe |
| 5 | | | | 10 | | | | | 15 | | | | | 20 | |

| | | | | | | | | | | | | | | | |
|---|---|---|---|---|---|---|---|---|---|---|---|---|---|---|---|
| aac | gcg | acg | aag | tcc | ggc | acc | ccg | gtc | ttc | atc | acc | gcc | ggc | cac | tgc | 702 |
| Asn | Ala | Thr | Lys | Ser | Gly | Thr | Pro | Val | Phe | Ile | Thr | Ala | Gly | His | Cys |
| | | | | 25 | | | | | 30 | | | | | 35 | |

| | | | | | | | | | | | | | | | |
|---|---|---|---|---|---|---|---|---|---|---|---|---|---|---|---|
| gcc | gag | ggg | aac | cag | acc | ttc | acg | cgc | aac | ggc | acg | acc | ctc | ggc | acg | 750 |
| Ala | Glu | Gly | Asn | Gln | Thr | Phe | Thr | Arg | Asn | Gly | Thr | Thr | Leu | Gly | Thr |
| | | 40 | | | | | 45 | | | | | 50 | | | |

| | | | | | | | | | | | | | | | |
|---|---|---|---|---|---|---|---|---|---|---|---|---|---|---|---|
| acc | cgc | ggc | tgg | tcc | ttc | ccg | ggc | aac | gac | tac | gcc | tac | tcg | agc | ctc | 798 |
| Thr | Arg | Gly | Trp | Ser | Phe | Pro | Gly | Asn | Asp | Tyr | Ala | Tyr | Ser | Ser | Leu |
| | | 55 | | | | | 60 | | | | | 65 | | | |

| | | | | | | | | | | | | | | | |
|---|---|---|---|---|---|---|---|---|---|---|---|---|---|---|---|
| acc | tcg | agc | tgg | acc | ggc | atc | ggc | gcc | gtc | gac | ctg | tgg | aac | ggc | acg | 846 |
| Thr | Ser | Ser | Trp | Thr | Gly | Ile | Gly | Ala | Val | Asp | Leu | Trp | Asn | Gly | Thr |
| | 70 | | | | | 75 | | | | | 80 | | | | |

| | | | | | | | | | | | | | | | |
|---|---|---|---|---|---|---|---|---|---|---|---|---|---|---|---|
| agc | gcg | cgc | tcc | gtc | acg | ggc | tcg | agc | aac | gcc | gcc | gtc | ggc | acc | gcg | 894 |
| Ser | Ala | Arg | Ser | Val | Thr | Gly | Ser | Ser | Asn | Ala | Ala | Val | Gly | Thr | Ala |
| 85 | | | | | 90 | | | | | 95 | | | | | 100 |

| | | | | | | | | | | | | | | | |
|---|---|---|---|---|---|---|---|---|---|---|---|---|---|---|---|
| atc | tgc | aag | tcg | ggc | cgc | acg | acc | ggc | tgg | acc | tgt | ggc | tcg | gtc | cag | 942 |
| Ile | Cys | Lys | Ser | Gly | Arg | Thr | Thr | Gly | Trp | Thr | Cys | Gly | Ser | Val | Gln |
| | | | | 105 | | | | | 110 | | | | | 115 | |

| | | | | | | | | | | | | | | | |
|---|---|---|---|---|---|---|---|---|---|---|---|---|---|---|---|
| acc | aag | aac | gtc | acc | gtc | aac | tac | aac | aac | ggc | gac | ggc | acc | tac | tcg | 990 |
| Thr | Lys | Asn | Val | Thr | Val | Asn | Tyr | Asn | Asn | Gly | Asp | Gly | Thr | Tyr | Ser |
| | | | 120 | | | | | 125 | | | | | 130 | | |

| | | | | | | | | | | | | | | | |
|---|---|---|---|---|---|---|---|---|---|---|---|---|---|---|---|
| acc | gtg | agc | ggc | ctg | acg | aag | tcc | aac | acc | tgc | acc | gag | ggt | ggc | gac | 1038 |
| Thr | Val | Ser | Gly | Leu | Thr | Lys | Ser | Asn | Thr | Cys | Thr | Glu | Gly | Gly | Asp |
| | | 135 | | | | | 140 | | | | | 145 | | | |

| | | | | | | | | | | | | | | | |
|---|---|---|---|---|---|---|---|---|---|---|---|---|---|---|---|
| tcc | ggc | ggc | tcg | tgg | atg | gcg | ggc | aac | ctc | gcc | cag | ggc | gtg | acg | agc | 1086 |
| Ser | Gly | Gly | Ser | Trp | Met | Ala | Gly | Asn | Leu | Ala | Gln | Gly | Val | Thr | Ser |
| | 150 | | | | | 155 | | | | | 160 | | | | |

| | | | | | | | | | | | | | | | |
|---|---|---|---|---|---|---|---|---|---|---|---|---|---|---|---|
| ggc | ggc | gcc | ggc | tac | ggc | tcc | aac | ggc | gtc | tgc | ggc | cag | aag | gtc | ggc | 1134 |
| Gly | Gly | Ala | Gly | Tyr | Gly | Ser | Asn | Gly | Val | Cys | Gly | Gln | Lys | Val | Gly |
| 165 | | | | | 170 | | | | | 175 | | | | | 180 |

| | | | | | | | | | | | | | | | |
|---|---|---|---|---|---|---|---|---|---|---|---|---|---|---|---|
| cag | ccc | aac | atc | gcc | tac | ttc | cag | ccg | atc | ggc | gag | atc | ctc | tcc | gtc | 1182 |
| Gln | Pro | Asn | Ile | Ala | Tyr | Phe | Gln | Pro | Ile | Gly | Glu | Ile | Leu | Ser | Val |
| | | | | 185 | | | | | 190 | | | | | 195 | |

| | | | | | | | | |
|---|---|---|---|---|---|---|---|---|
| tac | ggc | ctc | acc | ctc | aag | acc | gcc | tga | 1209 |
| Tyr | Gly | Leu | Thr | Leu | Lys | Thr | Ala | |
| | | | 200 | | | | | |

<210> SEQ ID NO 17
<211> LENGTH: 402
<212> TYPE: PRT
<213> ORGANISM: Knoellia flava

<400> SEQUENCE: 17

Met Ser Arg Arg Arg Leu Thr Val Leu Ala Gly Gly Leu Ser Ala
              -195                   -190               -185

```
Ala Ala Ala Ala  Thr Ala Leu Cys Val  Ala Pro Ala Ser Ala  Ala
        -180              -175               -170

Thr Ser Ala Ala  Gly Gly Pro Glu Pro  Ser Thr Gly Pro Leu  Ala
        -165              -160               -155

Thr Asp Ser Gly  Ala Ser Val Ala Glu  Met Ser Ala Arg Trp  Leu
        -150              -145               -140

Ala Lys Glu His  Asp Leu Ser Ile Glu  Thr Ala Arg Glu Arg  Ile
        -135              -130               -125

Ala Ser Gln Glu  Asp Lys Ser Arg Lys  Ala Glu Ala Leu Glu  Arg
        -120              -115               -110

Ser Leu Gly Ala  Arg Ala Val Gly Ser  Phe Ile Asp Gln Thr Gly Gly
        -105              -100                -95

Val Leu Val Val  Asn Val Thr Asp Ala  Asp Ala Ala Arg Val  Gln
         -90               -85               -80

Lys Ala Gly Ala  Thr Ala Arg Val Val  Thr Glu Asp Lys Ala  Glu Leu
         -75               -70               -65

Gly Ala Ser Gln  Ala Arg Ala Val Lys  Ala Leu Gly Ala Thr Val Ile
-60              -55                -50                -45

Asp Ser Ser Val  Asp Pro Val Thr Asn  Lys Val Val Thr Val  Pro
         -40               -35               -30

Thr Ala Asp Val  Ala Ala Ala Arg Ala  Arg Thr Ser Asp Pro  Ser Val
         -25               -20               -15

Thr Ile Gln Gly  Thr Asp Ala Thr Val  Ser Thr Gln Ala Asn  Val Tyr
         -10                -5                -1  1

Gly Gly Gln Gln  Ile Glu Phe Ser Gly  Tyr Val Cys Ser Leu  Gly Phe
5                 10                 15                  20

Asn Ala Thr Lys  Ser Gly Thr Pro Val  Phe Ile Thr Ala Gly  His Cys
         25                30                 35

Ala Glu Gly Asn  Gln Thr Phe Thr Arg  Asn Gly Thr Thr Leu  Gly Thr
         40                45                 50

Thr Arg Gly Trp  Ser Phe Pro Gly Asn  Asp Tyr Ala Tyr Ser  Ser Leu
         55                60                 65

Thr Ser Ser Trp  Thr Gly Ile Gly Ala  Val Asp Leu Trp Asn  Gly Thr
         70                75                 80

Ser Ala Arg Ser  Val Thr Gly Ser Ser  Asn Ala Ala Val Gly Thr Ala
85                90                 95                  100

Ile Cys Lys Ser  Gly Arg Thr Thr Gly  Trp Thr Cys Gly Ser  Val Gln
         105               110                115

Thr Lys Asn Val  Thr Val Asn Tyr Asn  Asn Gly Asp Gly Thr  Tyr Ser
         120               125                130

Thr Val Ser Gly  Leu Thr Lys Ser Asn  Thr Cys Thr Glu Gly  Gly Asp
         135               140                145

Ser Gly Gly Ser  Trp Met Ala Gly Asn  Leu Ala Gln Gly Val  Thr Ser
         150               155                160

Gly Gly Ala Gly  Tyr Gly Ser Asn Gly  Val Cys Gly Gln Lys  Val Gly
165               170                175                 180

Gln Pro Asn Ile  Ala Tyr Phe Gln Pro  Ile Gly Glu Ile Leu  Ser Val
         185               190                195

Tyr Gly Leu Thr  Leu Lys Thr Ala
         200
```

<210> SEQ ID NO 18
<211> LENGTH: 1200
<212> TYPE: DNA

```
<213> ORGANISM: Artificial Sequence
<220> FEATURE:
<223> OTHER INFORMATION: Codon optimized synthetic gene
<220> FEATURE:
<221> NAME/KEY: CDS
<222> LOCATION: (1)..(1200)
<220> FEATURE:
<221> NAME/KEY: sig_peptide
<222> LOCATION: (1)..(81)
<220> FEATURE:
<221> NAME/KEY: mat_peptide
<222> LOCATION: (589)..(1200)

<400> SEQUENCE: 18 atg aag aaa ccg ttg ggg aaa att gtc gca agc acc gca cta ctc      45
Met Lys Lys Pro Leu Gly Lys Ile Val Ala Ser Thr Ala Leu Leu
    -195                -190                -185 att tct gtt gct ttt agt tca tcg atc gca tcg gct gct aca tct      90
Ile Ser Val Ala Phe Ser Ser Ser Ile Ala Ser Ala Ala Thr Ser
    -180                -175                -170 gca gct ggt ggc cca gaa cca tca act ggc cca ctt gct aca gat     135
Ala Ala Gly Gly Pro Glu Pro Ser Thr Gly Pro Leu Ala Thr Asp
    -165                -160                -155 tct ggc gct tca gtt gcc gag atg tca gca cgc tgg ctt gcg aaa     180
Ser Gly Ala Ser Val Ala Glu Met Ser Ala Arg Trp Leu Ala Lys
    -150                -145                -140 gaa cac gat ctt tca att gag act gca cgt gag cgc atc gct agc     225
Glu His Asp Leu Ser Ile Glu Thr Ala Arg Glu Arg Ile Ala Ser
    -135                -130                -125 cag gaa gac aaa tct cgc aag gct gaa gct ctt gaa cgc tca ctt     270
Gln Glu Asp Lys Ser Arg Lys Ala Glu Ala Leu Glu Arg Ser Leu
    -120                -115                -110 ggc gct cgt gct gtt ggc agc ttt atc gac caa act ggc ggt gta ttg  318
Gly Ala Arg Ala Val Gly Ser Phe Ile Asp Gln Thr Gly Gly Val Leu
    -105                -100                 -95 gta gta aac gtt act gat gcg gat gca gca gct cgc gtt caa aag gca  366
Val Val Asn Val Thr Asp Ala Asp Ala Ala Ala Arg Val Gln Lys Ala
     -90                 -85                 -80                -75 gga gct aca gct cgt gtt gtt act gag gat aag gct gaa ctt ggc gct  414
Gly Ala Thr Ala Arg Val Val Thr Glu Asp Lys Ala Glu Leu Gly Ala
                 -70                 -65                 -60 tct caa gct cgt gct gtt aag gct ctt ggt gcc act gta att gat agc  462
Ser Gln Ala Arg Ala Val Lys Ala Leu Gly Ala Thr Val Ile Asp Ser
                 -55                 -50                 -45 tca gtt gac cct gta acg aac aaa gtt gta gtt aca gta cct act gct  510
Ser Val Asp Pro Val Thr Asn Lys Val Val Val Thr Val Pro Thr Ala
             -40                 -35                 -30 gat gtt gcg gca gca cgt gca cgt aca agc gac cca tct gta act att  558
Asp Val Ala Ala Ala Arg Ala Arg Thr Ser Asp Pro Ser Val Thr Ile
         -25                 -20                 -15 caa gga aca gac gca acg gtt tct aca cag gct aac gtt tat ggt ggc  606
Gln Gly Thr Asp Ala Thr Val Ser Thr Gln Ala Asn Val Tyr Gly Gly
-10                  -5                  -1   1                5 cag cag atc gag ttc tct gga tac gta tgt tca tta ggt ttc aac gca  654
Gln Gln Ile Glu Phe Ser Gly Tyr Val Cys Ser Leu Gly Phe Asn Ala
                 10                  15                  20 act aaa tct gga act cct gtt ttc atc aca gct ggc cat tgt gcg gaa  702
Thr Lys Ser Gly Thr Pro Val Phe Ile Thr Ala Gly His Cys Ala Glu
             25                  30                  35 ggt aac cag act ttc act cgt aat ggt aca aca ttg ggt aca aca cgc  750
Gly Asn Gln Thr Phe Thr Arg Asn Gly Thr Thr Leu Gly Thr Thr Arg
         40                  45                  50
```

-continued

```
ggt tgg tct ttt cca ggt aac gat tat gcg tac tca tct ctt act tct    798
Gly Trp Ser Phe Pro Gly Asn Asp Tyr Ala Tyr Ser Ser Leu Thr Ser
 55                  60                  65                  70 tct tgg act ggt att gga gct gtt gac tta tgg aat gga aca tca gct    846
Ser Trp Thr Gly Ile Gly Ala Val Asp Leu Trp Asn Gly Thr Ser Ala
                 75                  80                  85 cgc tct gta act ggc tca tca aac gct gct gtt gga act gca att tgc    894
Arg Ser Val Thr Gly Ser Ser Asn Ala Ala Val Gly Thr Ala Ile Cys
             90                  95                 100 aaa tct ggt cgt aca acg gga tgg aca tgt ggt tct gta caa acg aaa    942
Lys Ser Gly Arg Thr Thr Gly Trp Thr Cys Gly Ser Val Gln Thr Lys
         105                 110                 115 aac gta act gta aac tat aac aac gga gat ggt aca tat tct act gta    990
Asn Val Thr Val Asn Tyr Asn Asn Gly Asp Gly Thr Tyr Ser Thr Val
     120                 125                 130 tct ggt ctt aca aaa agc aat act tgc act gaa ggt gga gat tca ggc   1038
Ser Gly Leu Thr Lys Ser Asn Thr Cys Thr Glu Gly Gly Asp Ser Gly
 135                 140                 145                 150 ggt tct tgg atg gct ggc aac tta gca caa ggt gta act agc ggt ggt   1086
Gly Ser Trp Met Ala Gly Asn Leu Ala Gln Gly Val Thr Ser Gly Gly
                 155                 160                 165 gct ggc tat ggt agc aat gga gta tgt ggc cag aaa gta ggt caa ccg   1134
Ala Gly Tyr Gly Ser Asn Gly Val Cys Gly Gln Lys Val Gly Gln Pro
             170                 175                 180 aac att gct tac ttt cag cct atc ggt gaa atc ttg tct gtt tat ggt   1182
Asn Ile Ala Tyr Phe Gln Pro Ile Gly Glu Ile Leu Ser Val Tyr Gly
         185                 190                 195 ctt aca ttg aaa aca gct                                           1200
Leu Thr Leu Lys Thr Ala
     200

<210> SEQ ID NO 19
<211> LENGTH: 400
<212> TYPE: PRT
<213> ORGANISM: Artificial Sequence
<220> FEATURE:
<223> OTHER INFORMATION: Synthetic Construct

<400> SEQUENCE: 19

Met Lys  Lys Pro Leu Gly  Lys Ile Val Ala Ser Thr  Ala Leu Leu
    -195              -190              -185

Ile Ser  Val Ala Phe Ser  Ser Ile Ala Ser Ala  Ala Thr Ser
    -180              -175              -170

Ala Ala  Gly Gly Pro Glu  Pro Ser Thr Gly Pro  Leu Ala Thr Asp
    -165              -160              -155

Ser Gly  Ala Ser Val Ala Glu  Met Ser Ala Arg Trp  Leu Ala Lys
    -150              -145              -140

Glu His  Asp Leu Ser Ile Glu  Thr Ala Arg Glu Arg  Ile Ala Ser
    -135              -130              -125

Gln Glu  Asp Lys Ser Arg Lys  Ala Glu Ala Leu Glu  Arg Ser Leu
    -120              -115              -110

Gly Ala  Arg Ala Val Gly Ser  Phe Ile Asp Gln Thr  Gly Gly Val Leu
    -105              -100              -95

Val Val Asn Val Thr Asp Ala Asp Ala Ala Arg Val Gln Lys Ala
-90               -85              -80                   -75

Gly Ala Thr Ala Arg Val Val Thr Glu Asp Lys Ala Glu Leu Gly Ala
                 -70              -65                   -60

Ser Gln Ala Arg Ala Val Lys Ala Leu Gly Ala Thr Val Ile Asp Ser
         -55              -50                   -45
```

Ser Val Asp Pro Val Thr Asn Lys Val Val Thr Val Pro Thr Ala
    -40             -35                 -30

Asp Val Ala Ala Arg Ala Arg Thr Ser Asp Pro Ser Val Thr Ile
    -25             -20                 -15

Gln Gly Thr Asp Ala Thr Val Ser Thr Gln Ala Asn Val Tyr Gly Gly
-10              -5                  -1   1                 5

Gln Gln Ile Glu Phe Ser Gly Tyr Val Cys Ser Leu Gly Phe Asn Ala
            10                  15                  20

Thr Lys Ser Gly Thr Pro Val Phe Ile Thr Ala Gly His Cys Ala Glu
        25                  30                  35

Gly Asn Gln Thr Phe Thr Arg Asn Gly Thr Thr Leu Gly Thr Thr Arg
    40                  45                  50

Gly Trp Ser Phe Pro Gly Asn Asp Tyr Ala Tyr Ser Ser Leu Thr Ser
55                  60                  65                  70

Ser Trp Thr Gly Ile Gly Ala Val Asp Leu Trp Asn Gly Thr Ser Ala
            75                  80                  85

Arg Ser Val Thr Gly Ser Ser Asn Ala Ala Val Gly Thr Ala Ile Cys
            90                  95                  100

Lys Ser Gly Arg Thr Thr Gly Trp Thr Cys Gly Ser Val Gln Thr Lys
            105                 110                 115

Asn Val Thr Val Asn Tyr Asn Asn Gly Asp Gly Thr Tyr Ser Thr Val
    120                 125                 130

Ser Gly Leu Thr Lys Ser Asn Thr Cys Thr Glu Gly Gly Asp Ser Gly
135             140                 145                 150

Gly Ser Trp Met Ala Gly Asn Leu Ala Gln Gly Val Thr Ser Gly Gly
            155                 160                 165

Ala Gly Tyr Gly Ser Asn Gly Val Cys Gly Gln Lys Val Gly Gln Pro
            170                 175                 180

Asn Ile Ala Tyr Phe Gln Pro Ile Gly Glu Ile Leu Ser Val Tyr Gly
            185                 190                 195

Leu Thr Leu Lys Thr Ala
    200

<210> SEQ ID NO 20
<211> LENGTH: 204
<212> TYPE: PRT
<213> ORGANISM: Knoellia flava
<220> FEATURE:
<221> NAME/KEY: mat_peptide
<222> LOCATION: (1)..(204)

<400> SEQUENCE: 20

Ala Asn Val Tyr Gly Gly Gln Gln Ile Glu Phe Ser Gly Tyr Val Cys
1               5                   10                  15

Ser Leu Gly Phe Asn Ala Thr Lys Ser Gly Thr Pro Val Phe Ile Thr
            20                  25                  30

Ala Gly His Cys Ala Glu Gly Asn Gln Thr Phe Thr Arg Asn Gly Thr
        35                  40                  45

Thr Leu Gly Thr Thr Arg Gly Trp Ser Phe Pro Gly Asn Asp Tyr Ala
    50                  55                  60

Tyr Ser Ser Leu Thr Ser Ser Trp Thr Gly Ile Gly Ala Val Asp Leu
65                  70                  75                  80

Trp Asn Gly Thr Ser Ala Arg Ser Val Thr Gly Ser Ser Asn Ala Ala
            85                  90                  95

Val Gly Thr Ala Ile Cys Lys Ser Gly Arg Thr Thr Gly Trp Thr Cys

```
                     100                 105                 110
Gly Ser Val Gln Thr Lys Asn Val Thr Val Asn Tyr Asn Asn Gly Asp
            115                 120                 125

Gly Thr Tyr Ser Thr Val Ser Gly Leu Thr Lys Ser Asn Thr Cys Thr
            130                 135                 140

Glu Gly Gly Asp Ser Gly Gly Ser Trp Met Ala Gly Asn Leu Ala Gln
145                 150                 155                 160

Gly Val Thr Ser Gly Gly Ala Gly Tyr Gly Ser Asn Gly Val Cys Gly
            165                 170                 175

Gln Lys Val Gly Gln Pro Asn Ile Ala Tyr Phe Gln Pro Ile Gly Glu
            180                 185                 190

Ile Leu Ser Val Tyr Gly Leu Thr Leu Lys Thr Ala
            195                 200
```